US012605251B1

(12) United States Patent (10) Patent No.: US 12,605,251 B1

Wesorick et al. (45) Date of Patent: Apr. 21, 2026

(54) PATIENT-SPECIFIC SHOULDER IMPLANTS AND PROCESSES FOR PRODUCING AND USING THE SAME

(71) Applicant: restor3d, Inc., Durham, NC (US)

(72) Inventors: Benjamin Robert Wesorick, New York, NY (US); Conner James Helbling, Phoenix, AZ (US); Christopher James Robinson, Durham, NC (US); Alexandra Falis, Durham, NC (US); George Samuel Koser, Morrisville, NC (US); Nathan Timothy Evans, Durham, NC (US)

(73) Assignee: restor3d, Inc., Durham, NC (US)

( * ) Notice: Subject to any disclaimer, the term of this patent is extended or adjusted under 35 U.S.C. 154(b) by 0 days.

(21) Appl. No.: 19/094,414

(22) Filed: Mar. 28, 2025

(51) Int. Cl.
| | |
|---|---|
| *A61F 2/30* | (2006.01) |
| *A61B 17/17* | (2006.01) |
| *A61B 17/80* | (2006.01) |
| *A61B 17/86* | (2006.01) |
| *A61F 2/40* | (2006.01) |
| *A61F 2/46* | (2006.01) |

(52) U.S. Cl.
CPC .......... *A61F 2/4081* (2013.01); *A61F 2/4684* (2013.01); *A61F 2002/3069* (2013.01)

(58) Field of Classification Search
None
See application file for complete search history.

(56) References Cited

U.S. PATENT DOCUMENTS

| | | | |
|---|---|---|---|
| 1,428,247 | A | 9/1922 | Morris |
| D220,184 | S | 3/1971 | Boone |
| 3,872,519 | A | 3/1975 | Giannestras et al. |
| D265,288 | S | 7/1982 | McLean |
| 4,440,835 | A | 4/1984 | Vignaud |
| 4,588,574 | A | 5/1986 | Felder et al. |
| 4,829,152 | A | 5/1989 | Rostoker et al. |

(Continued)

FOREIGN PATENT DOCUMENTS

| | | | | |
|---|---|---|---|---|
| CA | 2597617 | A1 * | 8/2006 | ............... A61F 2/40 |
| CA | 2646995 | A1 * | 9/2007 | ............... A61F 2/40 |

(Continued)

OTHER PUBLICATIONS

Disclosure by Applicant re: surgical plan dated Mar. 27, 2024, 12 pages.

(Continued)

*Primary Examiner* — Ann Hu

(74) *Attorney, Agent, or Firm* — Husch Blackwell LLP; Bryan D. Stewart; Andrew C. Landsman

(57) ABSTRACT

This disclosure relates to systems, devices, and processes for performing a reverse shoulder arthroplasty using one or more patient-specific shoulder implants and can include a baseplate implant and a humeral stem implant, both of which can be designed and 3D-printed. In various embodiments, the baseplate includes a fixation member (e.g., a post) and a taper. In at least one embodiment, the fixation member and the taper can each be at any location and protrude from the baseplate at any angle. In at least one embodiment, the system includes a patient-specific pin guide and trial, which have features corresponding to those of the baseplate.

20 Claims, 59 Drawing Sheets

(56) References Cited

U.S. PATENT DOCUMENTS

| D309,185 | S | 7/1990 | Lockawich |
| D336,517 | S | 6/1993 | McKeown |
| 5,248,456 | A | 9/1993 | Evans, Jr. et al. |
| D358,211 | S | 5/1995 | Cohen |
| D358,647 | S | 5/1995 | Cohen et al. |
| 5,497,785 | A | 3/1996 | Viera |
| 5,497,786 | A | 3/1996 | Urick |
| 5,591,191 | A | 1/1997 | Kieturakis |
| 5,766,259 | A | 6/1998 | Sammarco |
| 5,947,965 | A | 9/1999 | Bryan |
| 6,183,519 | B1 | 2/2001 | Bonnin et al. |
| 6,419,491 | B1 | 7/2002 | Ricci et al. |
| 6,461,358 | B1 | 10/2002 | Faccioli et al. |
| D490,901 | S | 6/2004 | Schulter et al. |
| D493,890 | S | 8/2004 | Schulter et al. |
| 6,989,003 | B2 | 1/2006 | Wing et al. |
| D521,642 | S | 5/2006 | Dorahy |
| 7,048,741 | B2 | 5/2006 | Swanson |
| 7,125,423 | B2 | 10/2006 | Hazebrouck |
| D539,426 | S | 3/2007 | Callaghan |
| D593,202 | S | 5/2009 | Petersen |
| 7,534,270 | B2 | 5/2009 | Ball |
| D595,853 | S | 7/2009 | Hanson et al. |
| D598,094 | S | 8/2009 | Alber |
| D604,153 | S | 11/2009 | Wantz |
| 7,632,575 | B2 | 12/2009 | Justin et al. |
| 7,666,522 | B2 | 2/2010 | Justin et al. |
| D611,147 | S | 3/2010 | Hanson et al. |
| D618,800 | S | 6/2010 | Mayon et al. |
| D620,111 | S | 7/2010 | Courtney et al. |
| D623,749 | S | 9/2010 | Horton et al. |
| 7,819,614 | B2 | 10/2010 | Versino et al. |
| D628,344 | S | 11/2010 | Raviv |
| D653,756 | S | 2/2012 | Courtney et al. |
| 8,128,580 | B2 | 3/2012 | Fujimagari et al. |
| 8,142,886 | B2 | 3/2012 | Noble et al. |
| 8,157,866 | B2 * | 4/2012 | Winslow ............ A61B 17/1778 |
| | | | 623/19.12 |
| D660,432 | S | 5/2012 | Braido |
| D660,966 | S | 5/2012 | Sheild |
| D666,298 | S | 8/2012 | Sibhatu et al. |
| 8,262,589 | B2 | 9/2012 | Lupton |
| 8,382,755 | B2 | 2/2013 | Austin et al. |
| D681,204 | S | 4/2013 | Farris et al. |
| D683,856 | S | 6/2013 | Chin et al. |
| 8,529,568 | B2 | 9/2013 | Bouadi |
| 8,532,806 | B1 | 9/2013 | Masson |
| D692,136 | S | 10/2013 | Tyber |
| 8,556,971 | B2 | 10/2013 | Lang |
| 8,632,597 | B2 | 1/2014 | Lappin |
| D700,700 | S | 3/2014 | Efinger |
| 8,715,362 | B2 | 5/2014 | Reiley et al. |
| D708,747 | S | 7/2014 | Curran et al. |
| 8,771,365 | B2 | 7/2014 | Bojarski et al. |
| 8,781,557 | B2 | 7/2014 | Dean et al. |
| 8,845,743 | B2 * | 9/2014 | Termanini ................. A61F 2/32 |
| | | | 623/908 |
| 8,870,889 | B2 | 10/2014 | Frey |
| D722,693 | S | 2/2015 | Kaufmann et al. |
| 8,945,229 | B2 | 2/2015 | Lappin |
| 8,945,230 | B2 | 2/2015 | Lang et al. |
| 8,951,260 | B2 | 2/2015 | Lang et al. |
| 8,965,088 | B2 | 2/2015 | Tsougarakis et al. |
| 9,020,788 | B2 | 4/2015 | Lang et al. |
| 9,034,237 | B2 | 5/2015 | Sperry et al. |
| 9,044,330 | B2 | 6/2015 | Chavarria et al. |
| 9,055,953 | B2 | 6/2015 | Lang et al. |
| D734,460 | S | 7/2015 | Froidevaux |
| D735,860 | S | 8/2015 | Palinchik et al. |
| D736,384 | S | 8/2015 | Palinchik et al. |
| 9,095,353 | B2 | 8/2015 | Burdulis, Jr. et al. |
| 9,095,439 | B2 | 8/2015 | Lian |
| 9,144,500 | B2 | 9/2015 | Harding, Jr. |
| 9,180,029 | B2 | 11/2015 | Hollister et al. |
| 9,186,257 | B2 | 11/2015 | Geisler et al. |
| D747,485 | S | 1/2016 | Oi |
| 9,233,003 | B2 | 1/2016 | Roche et al. |
| 9,295,482 | B2 | 3/2016 | Fitz et al. |
| 9,308,053 | B2 | 4/2016 | Bojarski et al. |
| 9,308,091 | B2 | 4/2016 | Lang |
| 9,326,780 | B2 | 5/2016 | Wong et al. |
| 9,333,058 | B1 | 5/2016 | Krastev |
| 9,351,743 | B2 | 5/2016 | Kehres et al. |
| 9,358,018 | B2 | 6/2016 | Fitz et al. |
| 9,364,896 | B2 | 6/2016 | Christensen et al. |
| 9,370,426 | B2 | 6/2016 | Gabbrielli et al. |
| 9,402,726 | B2 | 8/2016 | Linderman et al. |
| 9,408,615 | B2 | 8/2016 | Fitz et al. |
| 9,408,686 | B1 | 8/2016 | Miller et al. |
| 9,414,927 | B2 | 8/2016 | Lannotti et al. |
| 9,415,137 | B2 | 8/2016 | Meridew et al. |
| D767,137 | S | 9/2016 | Lin |
| 9,433,707 | B2 | 9/2016 | Swords et al. |
| 9,439,767 | B2 | 9/2016 | Bojarski et al. |
| 9,486,226 | B2 | 11/2016 | Chao |
| 9,495,483 | B2 | 11/2016 | Steines et al. |
| 9,498,344 | B2 * | 11/2016 | Hodorek ............... A61F 2/4637 |
| 9,510,952 | B2 | 12/2016 | Muir et al. |
| 9,517,134 | B2 | 12/2016 | Lang |
| 9,522,067 | B2 * | 12/2016 | Frankle ................. A61F 2/4081 |
| 9,532,880 | B2 | 1/2017 | Lappin |
| 9,561,115 | B2 | 2/2017 | Elahinia et al. |
| 9,579,106 | B2 * | 2/2017 | Lo .......................... A61B 17/15 |
| 9,579,110 | B2 | 2/2017 | Bojarski et al. |
| 9,597,130 | B2 | 3/2017 | Pappalardo et al. |
| 9,597,191 | B2 * | 3/2017 | Muir ..................... A61F 2/4014 |
| 9,603,711 | B2 | 3/2017 | Bojarski et al. |
| 9,610,168 | B2 | 4/2017 | Terrill et al. |
| 9,636,226 | B2 | 5/2017 | Hunt |
| 9,636,229 | B2 | 5/2017 | Lang et al. |
| 9,649,178 | B2 | 5/2017 | Ali |
| 9,662,226 | B2 | 5/2017 | Wickham |
| 9,668,873 | B2 | 6/2017 | Winslow et al. |
| 9,675,471 | B2 | 6/2017 | Bojarski et al. |
| 9,681,956 | B2 | 6/2017 | Al Hares et al. |
| 9,687,945 | B2 | 6/2017 | Steines et al. |
| 9,688,026 | B2 | 6/2017 | Ho et al. |
| 9,694,541 | B2 | 7/2017 | Pruett et al. |
| 9,700,420 | B2 | 7/2017 | Fitz et al. |
| 9,700,424 | B2 | 7/2017 | Sanders et al. |
| 9,700,971 | B2 | 7/2017 | Lang |
| 9,737,367 | B2 | 8/2017 | Steines et al. |
| 9,750,613 | B2 | 9/2017 | Petteys |
| 9,782,270 | B2 | 10/2017 | Wickham |
| 9,788,972 | B2 | 10/2017 | Flickinger et al. |
| 9,839,438 | B2 * | 12/2017 | Eash .................. A61B 17/1778 |
| 9,849,019 | B2 | 12/2017 | Miller et al. |
| 9,872,773 | B2 | 1/2018 | Lang et al. |
| D809,661 | S | 2/2018 | Mueller et al. |
| D813,394 | S | 3/2018 | DaCosta et al. |
| 9,907,670 | B2 | 3/2018 | DeRidder et al. |
| 9,910,935 | B2 | 3/2018 | Golway et al. |
| 9,913,723 | B2 | 3/2018 | Fitz et al. |
| 9,918,849 | B2 | 3/2018 | Morris et al. |
| 9,925,054 | B2 | 3/2018 | Siegler et al. |
| 9,943,370 | B2 | 4/2018 | Asseln et al. |
| 9,943,627 | B2 | 4/2018 | Zhou et al. |
| 9,949,839 | B2 | 4/2018 | Sander |
| 9,956,048 | B2 | 5/2018 | Bojarski et al. |
| 9,956,083 | B2 * | 5/2018 | Humphrey ............ A61F 2/4003 |
| 9,962,209 | B2 | 5/2018 | Dacosta et al. |
| 9,999,513 | B2 * | 6/2018 | Overes ..................... A61F 2/32 |
| 10,034,757 | B2 | 7/2018 | Kovacs et al. |
| D829,909 | S | 10/2018 | Horton |
| D832,441 | S | 10/2018 | DaCosta et al. |
| 10,085,839 | B2 | 10/2018 | Wong et al. |
| D835,276 | S | 12/2018 | Humphrey |
| D835,277 | S | 12/2018 | Gottlieb |
| D835,278 | S | 12/2018 | Gottlieb |
| D835,788 | S | 12/2018 | Jones et al. |
| D835,977 | S | 12/2018 | Pastorino et al. |
| 10,183,442 | B1 | 1/2019 | Miller |
| 10,245,152 | B2 | 4/2019 | Kloss |
| 10,245,164 | B2 * | 4/2019 | Muir ..................... A61F 2/4684 |

(56) References Cited

U.S. PATENT DOCUMENTS

| | | | |
|---|---|---|---|
| D849,944 S | 5/2019 | Dacosta |
| 10,278,823 B1 | 5/2019 | Xue et al. |
| D850,620 S | 6/2019 | Tyber |
| D855,184 S | 7/2019 | Predick |
| 10,357,377 B2 | 7/2019 | Nyahay et al. |
| D857,201 S | 8/2019 | Predick et al. |
| D858,769 S | 9/2019 | Barela et al. |
| 10,405,993 B2 * | 9/2019 | Deransart .......... A61B 17/1739 |
| 10,426,549 B2 | 10/2019 | Kehres et al. |
| 10,449,051 B2 | 10/2019 | Hamzey et al. |
| 10,485,670 B2 * | 11/2019 | Maale ................... A61F 2/4612 |
| D870,288 S | 12/2019 | Dang et al. |
| 10,492,686 B2 | 12/2019 | Hunter et al. |
| D873,031 S | 1/2020 | Martensson |
| D875,939 S | 2/2020 | DaCosta et al. |
| D877,907 S | 3/2020 | Linder et al. |
| D878,589 S | 3/2020 | Linder et al. |
| D878,590 S | 3/2020 | Linder et al. |
| D879,295 S | 3/2020 | Abbasi |
| D879,961 S | 3/2020 | Linder et al. |
| 10,583,012 B1 * | 3/2020 | Longobardi .......... A61F 2/4014 |
| D881,665 S | 4/2020 | Zemel et al. |
| 10,624,746 B2 | 4/2020 | Jones et al. |
| 10,667,924 B2 | 6/2020 | Nyahay et al. |
| 10,736,751 B2 | 8/2020 | Hodorek et al. |
| 10,744,001 B2 | 8/2020 | Sack |
| D899,900 S | 10/2020 | Blanco |
| 10,806,597 B2 | 10/2020 | Sournac et al. |
| 10,898,206 B2 | 1/2021 | Dacosta et al. |
| 10,937,542 B1 | 3/2021 | Mldirim |
| 10,940,015 B2 | 3/2021 | Sack |
| D917,697 S | 4/2021 | Reed et al. |
| 11,033,394 B2 | 6/2021 | Hamzey et al. |
| 11,090,161 B2 | 8/2021 | Hodorek |
| 11,135,771 B1 | 10/2021 | Reith et al. |
| D938,033 S | 12/2021 | Dang et al. |
| D942,623 S | 2/2022 | Cain |
| D942,624 S | 2/2022 | Cain |
| D944,400 S | 2/2022 | Cain |
| 11,273,048 B2 | 3/2022 | Cain et al. |
| 11,324,525 B1 | 5/2022 | Garvey et al. |
| 11,353,277 B2 | 6/2022 | Muceus et al. |
| 11,432,934 B2 | 9/2022 | Couture et al. |
| 11,439,726 B2 | 9/2022 | Spence et al. |
| D967,960 S | 10/2022 | Wang et al. |
| 11,471,203 B2 | 10/2022 | Sutika |
| D968,614 S | 11/2022 | Cain |
| 11,484,413 B1 * | 11/2022 | Miller ........................ A61F 2/28 |
| 11,490,907 B2 | 11/2022 | Mulqueen et al. |
| 11,564,802 B2 | 1/2023 | Ball et al. |
| D986,728 S | 5/2023 | Jou et al. |
| 11,648,125 B2 | 5/2023 | Ng |
| 11,666,367 B2 | 6/2023 | Goradia |
| 11,666,452 B2 | 6/2023 | Melkent et al. |
| D992,116 S | 7/2023 | Miller et al. |
| 11,744,716 B2 | 9/2023 | Jebsen et al. |
| 11,771,561 B2 * | 10/2023 | Running ............... A61F 2/4081 623/19.13 |
| 11,819,415 B2 | 11/2023 | Metcalfe et al. |
| 11,833,055 B2 * | 12/2023 | Hatzidakis ................. A61F 2/28 |
| 11,839,389 B2 * | 12/2023 | Termanini .............. A61B 17/15 |
| 11,850,144 B1 | 12/2023 | Garrigues |
| 11,850,158 B2 | 12/2023 | Simoes et al. |
| 11,883,040 B2 | 1/2024 | Bonin, Jr et al. |
| D1,013,875 S | 2/2024 | Miller et al. |
| D1,013,876 S | 2/2024 | Miller et al. |
| 11,950,822 B2 | 4/2024 | Champagne et al. |
| 11,960,266 B1 | 4/2024 | Kelly et al. |
| D1,030,046 S | 6/2024 | Boey et al. |
| 12,023,102 B2 | 7/2024 | Gutierrez et al. |
| 12,048,626 B2 * | 7/2024 | Winslow ............... A61F 2/4081 |
| 12,053,389 B2 * | 8/2024 | Frankle ................. A61F 2/4014 |
| 12,178,455 B2 * | 12/2024 | Neichel ............. A61B 17/1778 |
| 2001/0031966 A1 | 10/2001 | Tormala et al. |
| 2004/0049284 A1 | 3/2004 | German et al. |
| 2004/0049285 A1 | 3/2004 | Haas |
| 2004/0064187 A1 * | 4/2004 | Ball ....................... A61F 2/4637 623/19.11 |
| 2004/0148032 A1 | 7/2004 | Rutter et al. |
| 2004/0230313 A1 | 11/2004 | Saunders |
| 2005/0010302 A1 | 1/2005 | Dietz et al. |
| 2006/0063135 A1 | 3/2006 | Mehl |
| 2006/0074492 A1 | 4/2006 | Frey |
| 2006/0249875 A1 | 11/2006 | Robb et al. |
| 2007/0055251 A1 | 3/2007 | Huebner et al. |
| 2007/0100346 A1 | 5/2007 | Wyss et al. |
| 2007/0118243 A1 | 5/2007 | Schroeder et al. |
| 2008/0091271 A1 | 4/2008 | Bonitati et al. |
| 2008/0319448 A1 | 12/2008 | Lavallee et al. |
| 2009/0093668 A1 | 4/2009 | Marten et al. |
| 2009/0182430 A1 | 7/2009 | Tyber et al. |
| 2010/0055644 A1 | 3/2010 | Arni |
| 2010/0137990 A1 | 6/2010 | Apatsidis et al. |
| 2010/0168798 A1 | 7/2010 | Clineff et al. |
| 2010/0286791 A1 | 11/2010 | Goldsmith |
| 2011/0054611 A1 | 3/2011 | Wu et al. |
| 2011/0190898 A1 | 8/2011 | Lenz et al. |
| 2011/0224796 A1 | 9/2011 | Weiland et al. |
| 2011/0230974 A1 | 9/2011 | Musani |
| 2012/0064288 A1 | 3/2012 | Nakano et al. |
| 2012/0209392 A1 * | 8/2012 | Angibaud ............. A61F 2/4081 623/19.11 |
| 2012/0239152 A1 | 9/2012 | Ullrich, Jr. et al. |
| 2012/0257507 A1 | 10/2012 | Sato et al. |
| 2012/0259419 A1 | 10/2012 | Brown et al. |
| 2013/0046313 A1 | 2/2013 | Lian |
| 2013/0068968 A1 | 3/2013 | Daniel |
| 2013/0123935 A1 | 5/2013 | Hunt et al. |
| 2013/0184820 A1 | 7/2013 | Schwartz et al. |
| 2013/0197657 A1 | 8/2013 | Anca et al. |
| 2013/0274890 A1 | 10/2013 | Mckay |
| 2014/0039633 A1 * | 2/2014 | Roche ................... A61F 2/4081 623/19.13 |
| 2014/0100779 A1 | 4/2014 | Horvitz et al. |
| 2014/0107786 A1 | 4/2014 | Geisler et al. |
| 2014/0236299 A1 | 8/2014 | Roeder et al. |
| 2014/0277443 A1 | 9/2014 | Fleury et al. |
| 2014/0277452 A1 | 9/2014 | Skaer |
| 2014/0336680 A1 | 11/2014 | Medina et al. |
| 2014/0350688 A1 | 11/2014 | Michel et al. |
| 2014/0371863 A1 | 12/2014 | Vanasse et al. |
| 2015/0025666 A1 | 1/2015 | Olivieri et al. |
| 2015/0105858 A1 | 4/2015 | Papay et al. |
| 2015/0328004 A1 | 11/2015 | Mafhouz |
| 2015/0335434 A1 | 11/2015 | Patterson et al. |
| 2015/0343709 A1 | 12/2015 | Gerstle et al. |
| 2015/0351915 A1 | 12/2015 | DeFelice et al. |
| 2015/0374411 A1 | 12/2015 | Ehmke et al. |
| 2016/0051371 A1 | 2/2016 | DeFelice et al. |
| 2016/0089138 A1 | 3/2016 | Early et al. |
| 2016/0143749 A1 | 5/2016 | Holovacs et al. |
| 2016/0151833 A1 | 6/2016 | Tsao |
| 2016/0193055 A1 | 7/2016 | Ries |
| 2016/0199193 A1 | 7/2016 | Willis et al. |
| 2016/0213487 A1 | 7/2016 | Wilson et al. |
| 2016/0213488 A1 | 7/2016 | Moore et al. |
| 2016/0220288 A1 | 8/2016 | Dubois et al. |
| 2016/0228255 A1 | 8/2016 | Samuelson et al. |
| 2016/0256279 A1 | 9/2016 | Sanders et al. |
| 2016/0270931 A1 | 9/2016 | Trieu |
| 2016/0296285 A1 | 10/2016 | Chaoui et al. |
| 2016/0303793 A1 | 10/2016 | Ermoshkin et al. |
| 2016/0333152 A1 | 11/2016 | Cook et al. |
| 2016/0374829 A1 | 12/2016 | Vogt et al. |
| 2017/0014169 A1 | 1/2017 | Dean et al. |
| 2017/0018919 A1 | 1/2017 | Chen et al. |
| 2017/0020685 A1 | 1/2017 | Geisler et al. |
| 2017/0036403 A1 | 2/2017 | Ruff et al. |
| 2017/0042697 A1 | 2/2017 | McShane, III et al. |
| 2017/0056179 A1 | 3/2017 | Lorio |
| 2017/0066873 A1 | 3/2017 | Gardet |
| 2017/0105844 A1 | 4/2017 | Kuyler et al. |
| 2017/0143494 A1 | 5/2017 | Mahfouz |
| 2017/0156880 A1 | 6/2017 | Halverson et al. |

(56) References Cited

U.S. PATENT DOCUMENTS

| | | |
|---|---|---|
| 2017/0165085 A1 | 6/2017 | Lechmann et al. |
| 2017/0165790 A1 | 6/2017 | McCarthy et al. |
| 2017/0172758 A1 | 6/2017 | Field et al. |
| 2017/0182222 A1 | 6/2017 | Paddock et al. |
| 2017/0209274 A1 | 7/2017 | Beerens et al. |
| 2017/0239054 A1 | 8/2017 | Engstrand et al. |
| 2017/0239064 A1 | 8/2017 | Cordaro |
| 2017/0245998 A1 | 8/2017 | Padovani et al. |
| 2017/0252165 A1 | 9/2017 | Sharp et al. |
| 2017/0258606 A1 | 9/2017 | Afzal |
| 2017/0282455 A1 | 10/2017 | DeFelice et al. |
| 2017/0296244 A1 | 10/2017 | Schneider et al. |
| 2017/0304063 A1 | 10/2017 | Hatzidakis et al. |
| 2017/0319344 A1 | 11/2017 | Hunt |
| 2017/0323037 A1 | 11/2017 | Schroeder |
| 2017/0333205 A1 | 11/2017 | Joly et al. |
| 2017/0354510 A1 | 12/2017 | O'Neil et al. |
| 2017/0354513 A1 | 12/2017 | Maglaras et al. |
| 2017/0355815 A1 | 12/2017 | Becker et al. |
| 2017/0360488 A1 | 12/2017 | Kowalczyk et al. |
| 2017/0360563 A1 | 12/2017 | Hunt et al. |
| 2017/0360578 A1 | 12/2017 | Shin et al. |
| 2017/0367843 A1 | 12/2017 | Eisen et al. |
| 2017/0367845 A1 | 12/2017 | Eisen et al. |
| 2018/0008419 A1 | 1/2018 | Tyber et al. |
| 2018/0012517 A1 | 1/2018 | Ropelato et al. |
| 2018/0022017 A1 | 1/2018 | Fukumoto et al. |
| 2018/0064540 A1 | 3/2018 | Hunt et al. |
| 2018/0085230 A1 | 3/2018 | Hunt |
| 2018/0098858 A1 | 4/2018 | Valderrabano et al. |
| 2018/0104063 A1 | 4/2018 | Asaad |
| 2018/0110593 A1 | 4/2018 | Khalil |
| 2018/0110626 A1 | 4/2018 | McShane, III et al. |
| 2018/0110627 A1 | 4/2018 | Sack |
| 2018/0113992 A1 | 4/2018 | Eltorai et al. |
| 2018/0117219 A1 | 5/2018 | Yang et al. |
| 2018/0147319 A1 | 5/2018 | Colucci-Mizenko et al. |
| 2018/0196920 A1 | 7/2018 | Liang et al. |
| 2018/0256336 A1 | 9/2018 | Mueller et al. |
| 2018/0263782 A1 | 9/2018 | Lang et al. |
| 2018/0280140 A1 | 10/2018 | Jones et al. |
| 2018/0289380 A1 | 10/2018 | Mauldin et al. |
| 2018/0289515 A1 | 10/2018 | Nemes et al. |
| 2019/0159907 A1 | 5/2019 | Roche et al. |
| 2019/0167433 A1 | 6/2019 | Allen et al. |
| 2019/0262101 A1 | 8/2019 | Shanjani et al. |
| 2019/0269527 A1 | 9/2019 | Moore |
| 2019/0302736 A1 | 10/2019 | Chanin |
| 2019/0343652 A1 | 11/2019 | Petersheim et al. |
| 2020/0000595 A1 | 1/2020 | Jones et al. |
| 2020/0030102 A1 | 1/2020 | Mullens et al. |
| 2020/0030108 A1 | 1/2020 | Orphanos et al. |
| 2020/0046512 A1 | 2/2020 | Newman et al. |
| 2020/0085452 A1 | 3/2020 | Siegler |
| 2020/0085585 A1 | 3/2020 | Siegler |
| 2020/0113656 A1 | 4/2020 | Jo |
| 2020/0155321 A1 | 5/2020 | Dikovsky et al. |
| 2020/0171752 A1 | 6/2020 | Rogren |
| 2020/0171753 A1 | 6/2020 | Satko et al. |
| 2020/0188121 A1* | 6/2020 | Boux de Casson ......................... A61F 2/30734 |
| 2020/0253649 A1 | 8/2020 | Langdale et al. |
| 2020/0367910 A1 | 11/2020 | Hafez et al. |
| 2021/0000588 A1 | 1/2021 | Cain |
| 2021/0038401 A1* | 2/2021 | Ball ...................... A61F 2/4059 |
| 2021/0059822 A1 | 3/2021 | Casey et al. |
| 2021/0077276 A1 | 3/2021 | Garvey et al. |
| 2021/0110605 A1 | 4/2021 | Haslam et al. |
| 2021/0113222 A1 | 4/2021 | Khatibi et al. |
| 2021/0121298 A1 | 4/2021 | Walker et al. |
| 2021/0196288 A1 | 7/2021 | Hodorek et al. |
| 2021/0216683 A1 | 7/2021 | Rai et al. |
| 2021/0298908 A1 | 9/2021 | Holmes et al. |
| 2021/0307765 A1 | 10/2021 | Dumpe et al. |
| 2021/0340334 A1 | 11/2021 | Portela et al. |
| 2022/0023048 A1 | 1/2022 | Nolens et al. |
| 2022/0087670 A1 | 3/2022 | Selmoune |
| 2022/0110757 A1* | 4/2022 | Paterson ............... A61F 2/4081 |
| 2022/0134639 A1 | 5/2022 | Allen et al. |
| 2022/0142783 A1 | 5/2022 | Ahmadi |
| 2022/0168109 A1 | 6/2022 | Giordano et al. |
| 2022/0226094 A1 | 7/2022 | Chotkowski et al. |
| 2022/0249241 A1* | 8/2022 | Orbay ................... A61F 2/4081 |
| 2022/0296386 A1 | 9/2022 | Fang et al. |
| 2022/0401138 A1 | 12/2022 | Finley et al. |
| 2022/0409140 A1 | 12/2022 | Cordonnier et al. |
| 2023/0096120 A1* | 3/2023 | Longobardi .............. A61F 2/40 623/19.13 |
| 2023/0111847 A1 | 4/2023 | Leclercq et al. |
| 2023/0122922 A1 | 4/2023 | Daudet |
| 2023/0137504 A1* | 5/2023 | Gilotra .................. A61F 2/4081 623/19.13 |
| 2023/0138162 A1 | 5/2023 | Winston et al. |
| 2023/0190492 A1 | 6/2023 | Marks et al. |
| 2023/0233329 A1 | 7/2023 | Radermacher et al. |
| 2024/0033092 A1 | 2/2024 | Parthasarathy et al. |
| 2024/0065767 A1 | 2/2024 | Cordonnier et al. |
| 2024/0346768 A1 | 10/2024 | Crawford et al. |
| 2025/0213365 A1* | 7/2025 | Varadarajan .......... A61F 2/4081 |

FOREIGN PATENT DOCUMENTS

| | | | | |
|---|---|---|---|---|
| CA | 2903390 A1 * | 9/2014 | ........... | A61F 2/4684 |
| CN | 109567913 A | 4/2019 | | |
| CN | 110090096 A | 8/2019 | | |
| EP | 1180989 B1 | 4/2006 | | |
| EP | 2832321 A1 | 2/2015 | | |
| EP | 2635239 B1 | 7/2017 | | |
| EP | 2913030 B1 | 3/2018 | | |
| EP | 3586800 A1 | 1/2020 | | |
| EP | 4434496 A1 * | 9/2024 | ........... | A61F 2/4059 |
| FR | 3071400 A1 | 3/2019 | | |
| KR | 301007894 S | 5/2019 | | |
| WO | 2014020562 A1 | 2/2014 | | |
| WO | 2015054070 A1 | 4/2015 | | |
| WO | 2015191361 A1 | 12/2015 | | |
| WO | 2020123295 A1 | 6/2020 | | |
| WO | 2020231657 A1 | 11/2020 | | |
| WO | WO-2020252308 A1 * | 12/2020 | ........... | A61F 2/4612 |
| WO | 2023183793 A2 | 9/2023 | | |
| WO | WO-2024015899 A2 * | 1/2024 | ........... | A61F 2/4081 |
| WO | WO-2024020216 A1 * | 1/2024 | ........... | A61F 2/4081 |
| WO | WO-2024137512 A1 * | 6/2024 | ........... | A61F 2/4657 |
| WO | WO2025067730 A1 * | 4/2025 | | |

OTHER PUBLICATIONS

3D Printing for Orthopedic Implant, E-Plus-3D, https://www.eplus3d.com/3d-printing-for-orthopedic-implant.html, 2021, 7 pages.

Ntop, "3D printing implants: A complete guide", Retrieved from: https://www.ntop.com/resources/blog/3d-printing-implants-a-complete-guide/, Feb. 1, 2023, 21 pages.

Additive Orthopaedics, "Additive Orthopaedics 3d Printed Cotton Bone Segment", retrieved from: https://web.archive.org/web/20200919145251/https:/www.additiveorthopaedics.com/our-products/cotton/, 2019, 3 pages.

Alt, Sami. "Design for Sterilization Part 1: Steam Sterilization." Material, Material Technology Blog, Jun. 3, 2016, 3 pages.

Cera-Metal Orthopedic Implant Coating, ifdesign.com, Accessed Jul. 24, 2024, https://ifdesign.com/en/winner-ranking/projecUcera-metal/27188., 5 pages.

Cotton Wedge Portfolio with TIDAL Technology™, restor3d, retrieved from: https://assets-global.website-files.com/65d612f03cc5c490660ab482/65d612f03cc5c490660ab7b9_MKG-002%20Rev02%20Jun2023_Cotton%20Osteotomy%20Wedges%20Sales%20Sheet-2.pdf, 2023, 2 pages.

Yakacki et al., "Does 3D Printing Add Value In Orthopedics?", ODT, retrieved from: https://www.odtmag.com/does-3d-printing-add-value-in-orthopedics/, Mar. 29, 2019, 16 pages.

Ducheyne, Paul. "Comprehensive Biomaterials" Comprehensive Biomaterials, vol. 1, Elsevier, 2011, pp. 135-135.

(56) References Cited

OTHER PUBLICATIONS

Extended European Search Report dated Feb. 12, 2021 for European Patent Application No. EP20196410.3.

Indiamart, "Anterior Cervical Fusion Cage for Spine Surgery", accessed Dec. 9, 2020 on https://www.indiamart.com/proddetail/anterior-cervical-fusion-cage-12402896897.html, 8 pages.

Instagram, "restor3d", first available Jul. 21, 2020 on https://www.instagram.com/p/CC6dzt0AKcM/?utm_source=ig_web_copy_link, 2 pages.

Larraona et al., "Radiopaque material for 3D printing scaffolds", XXXV Congreso Anual de la Sociedad Espanola de Ingenieria Biomedica. Bilbao, 29 Nov.-Dec. 1, 2017, pp. 451-454.

Miller et al., "Fatigue of Injection Molded and 3D Printed Polycarbonate Urethane in Solution", Polymer, vol. 108, 2017, pp. 121-134.

Miller et al., Deformation and Fatigue of Tough 3D Printed Elastomer Scaffolds Processed by Fused Deposition Modeling and Continuous Liquid Interface Production, Journal of Mechanical Behavior Of Biomedical Materials, vol. 75, 2017, pp. 1-13.

MTP Hemiarthroplasty Implant Featuring TIDAL Technology™, resto3d, retrieved from: https://cdn.prod.website-files.com/65d612f03cc5c490660ab482/65d612f03cc5c490660ab7aa_restor3d-MTP-Sales-Sheet.pdf, 2023, 2 pages.

Ratnovsky et al., Mechanical Properties of Different Airway Stents, Medical Engineering and Physics, vol. 37, 2015, pp. 408-415.

Restor3d, "Products—Designed with surgeons for tailored clinical solutions", Retrieved from . https://web.archive.org/web/20200928123335/https:/restor3d.com/products, 2020, 5 pages.

Rozema et al., The Effects of Different Steam-Sterilization Programs on Material Properties of Poly(L-lactide), Journal of Applied Biomaterials, vol. 2, 1991, pp. 23-28.

Sandberg, "Nvision Biomedical Technologies: First FDA Clearance for Osteotomy Wedge System", Ortho Spine News, retrieved from: https://orthospinenews.com/2020/10/28/nvision-biomedical-technologies-first-fda-clearance-for-osteotomy-wedge-system-made-of-peek-optima-ha-enhanced/, 2020, 9 pages.

Sandberg, "SeaSpine Announces 25,000th NanoMetalene Implantation", Ortho Spine News, Retrieved from: https://orthospinenews.com/2019/12/18/seaspine-announces-25000th-nanometalene-implantation/, Dec. 18, 2019, 10 pages.

Sina, "Application logic of triple periodic minimum surface", retrieved from: https://k.sina.com.cn/article_2422410454_90630cd600100tlbm.html?from=science, Oct. 24, 2020, 6 pages.

Yan et al., "Microstructure and mechanical properties of aluminum alloy cellular lattice structures manufactured by direct metal laser sintering", Materials Science and Engineering A vol. 628, 2015, pp. 238-246.

Yan et al., "Ti-6AI-4V Triply Periodic Minimal Surface Structures for Bone Implants Fabricated Via Selective Laser Melting", Journal of the Mechanical Behavior of Biomedical Materials , vol. 51, 2015 , pp. 61-73.

Yosra K., "Johnson & Johnson Medical has acquired 3D-printed spinal implants specialist, Emerging Implant Technologies (EIT)", 3D Adept Media Retrieved from: https://3dadept.com/johnson-johnson-medical-has-acquired-3d-printed-spmplants-specialist-emerging-implant-technologies/, Sep. 17, 2018, 4 pages.

Disclosure by Applicant re:surgical plan dated Dec. 21, 2023, 12 pages.

Disclosure by Applicant re:surgical plan dated Feb. 24, 2022, 11 pages.

Disclosure by Applicant re:surgical plan dated Mar. 27, 2024, 11 pages.

Disclosure by Applicant re:surgical plan dated Mar. 20, 2024, 18 pages.

Disclosure by Applicant re:surgical plan dated Mar. 13, 2024, 14 pages.

Disclosure by Applicant re:surgical plan dated Feb. 27, 2024, 13 pages.

Disclosure by Applicant re:surgical plan dated Feb. 26, 2024, 12 pages.

Disclosure by Applicant re:surgical plan dated Dec. 11, 2024, 11 pages.

Disclosure by Applicant re:surgical plan dated Nov. 21, 2023, 24 pages.

Disclosure by Applicant re:surgical plan dated Sep. 26, 2023, 22 pages.

Disclosure by Applicant re:surgical plan dated Sep. 18, 2023, 21 pages.

Disclosure by Applicant re:surgical plan dated Sep. 7, 2023, 24 pages.

Disclosure by Applicant re:surgical plan dated Jan. 25, 2023, 11 pages.

Disclosure by Applicant re:surgical plan dated Nov. 8, 2023, 13 pages.

* cited by examiner

PATIENT-SPECIFIC SHOULDER IMPLANTS AND PROCESSES FOR PRODUCING AND USING THE SAME

BACKGROUND

The shoulder is a ball-and-socket joint wherein the round head of the humerus bone (ball) fits into the shallow glenoid fossa (socket) of the scapula. Damage or disease to the joint can cause pain, weakness, and stiffness. In some cases, a shoulder replacement procedure may be recommended for relief. One such procedure is a reverse shoulder arthroplasty (RSA) wherein damaged or diseased areas of bone around the patient shoulder joint are removed and replaced with metal or plastic implants. Specifically, the "ball" portion of the implant, or glenosphere, is placed on the scapular side of the joint, supported by a baseplate containing a central post or screw, and the "socket" portion of the implant is placed on the humeral side, supported by a metal stem in the humerus. However, standard models of the humeral stems and baseplates may not be appropriate for every patient and may present problems with fixation in the scapula and humerus. Thus, there is a long-felt, but unsolved need for patient-specific devices that provide improved fixation for RSA and various other surgical procedures and methods of producing and installing the same.

BRIEF SUMMARY OF THE DISCLOSURE

Briefly described, aspects of the present disclosure generally relate to a 3D-printed, patient-specific reverse shoulder arthroplasty (RSA) system, as well as processes for making and using the same. Use of a central screw or a post for glenosphere fixation is common in procedures such as RSAs, for the screw or post allows for the baseplate and the glenospheres to be installed in the patient with reduced concern of dislocation over time. The present disclosure relates to patient-specific systems that include a post or other fixation element that may be inserted at a range of angles into the scapula of the patient and is disconnected or independent of a location and angle of a taper for the glenosphere. The present disclosure also relates to patient-specific surfaces utilized in the surgical method, namely a pin guide face, a baseplate trial, and the baseplate, which may advantageously provide for customized treatment of patients.

The following embodiments and aspects thereof are described and illustrated in conjunction with systems, devices, and processes that are meant to be exemplary and illustrative, not limiting in scope.

Briefly described, aspects of the present disclosure generally relate to reverse shoulder arthroplasty systems and techniques. According to a first aspect, the present disclosure relates to a reverse shoulder arthroplasty implant system comprising: a glenoid system for interfacing with anatomy of a patient, wherein the anatomy defines a Friedman's Line extending from a center of the patient's glenoid cavity to a medial end of the patient's scapula, the glenoid system comprising: a baseplate comprising a baseplate body, the baseplate body comprising: a patient-specific baseplate face comprising a periphery and positioned opposite a second baseplate face, the patient-specific baseplate face arranged and shaped to conformally engage with a bony surface of the anatomy at a baseplate face angle, wherein a baseplate plane bisects the baseplate body at two representative points of the periphery, and the baseplate angle is between about 25° to 88° with respect to the baseplate plane and the Friedman's Line; a central post extending from the patient-specific baseplate face at a post angle and a post position, the post angle between about 2° to 80° with respect to the Friedman's Line; a taper extending from the second baseplate face at a taper angle and a taper position, the taper angle between about 2° to 80° with respect to the Friedman's Line; and one or more patient-specific regions comprising a textured surface; and a guide instrument comprising: a guide body comprising: a patient-specific guide face arranged and shaped to conformally engage with the bony surface at a guide face angle; and a guide opening positioned on the patient-specific guide face at a guide opening position and a guide opening angle; and a handle connected to the guide face by a shaft, wherein a guide element is inserted through the handle to the guide opening; and a trial instrument comprising: a trial body comprising a patient-specific trial face and a second trial face positioned opposite the patient-specific trial face, the patient-specific trial face arranged and shaped to conformally engage with the bony surface at a trial face angle; and a trial opening extending between the patient-specific trial face and the second trial face, the trial opening oriented at a trial opening position and a trial opening angle, wherein: the baseplate face angle, the guide face angle, and the trial face angle are substantially similar angles with respect to the Friedman's Line; the post angle, the guide opening angle, and the trial opening angle are substantially similar and are each measured with respect to the Friedman's Line; the post position, the guide opening position, and the trial opening position are substantially similar in relation to the bony surface; the post angle and the taper angle are different with respect to the Friedman's Line; and the post position and the taper position are offset by at least 1 mm.

According to a second aspect, the reverse shoulder arthroplasty implant system of the first aspect, wherein the Friedman's Line represents an x-axis; a y-axis extends 90° from the Friedman's Line in a vertical direction; and a z-axis extends 90° degrees from the Friedman's Line in a horizontal direction.

According to a third aspect, the reverse shoulder arthroplasty implant system of the second aspect or any other aspect, wherein the two representative points comprise a first point on the periphery furthest from a center of the patient-specific baseplate face and a second point on the periphery closest to the center of the patient-specific baseplate face.

According to a fourth aspect, the reverse shoulder arthroplasty implant system of the third aspect or any other aspect, wherein the baseplate face angle is not parallel to the x-axis.

According to a fifth aspect, the reverse shoulder arthroplasty implant system of the fourth aspect or any other aspect, wherein the baseplate face angle is not perpendicular to the x-axis.

According to a sixth aspect, the reverse shoulder arthroplasty implant system of the third aspect or any other aspect, wherein the baseplate face angle is between about 30° and 80°.

According to a seventh aspect, the reverse shoulder arthroplasty implant system of the sixth aspect or any other aspect, wherein the post angle is not parallel and not perpendicular to the x-axis.

According to an eighth aspect, the reverse shoulder arthroplasty implant system of the sixth aspect or any other aspect, wherein the post angle is between about 10° and 45°.

According to a ninth aspect, the reverse shoulder arthroplasty implant system of the eighth aspect or any other aspect, wherein the taper angle is not parallel and not perpendicular to the x-axis.

According to a tenth aspect, the reverse shoulder arthroplasty implant system of the eighth aspect or any other aspect, wherein the taper angle is between about 10° and 45°.

According to an eleventh aspect, the reverse shoulder arthroplasty implant system of the first aspect or any other aspect, wherein the baseplate body comprises a patient-specific thickness that varies between 3-100 mm.

According to a twelfth aspect, the reverse shoulder arthroplasty implant system of the first aspect or any other aspect, wherein at least one peripheral fixation through-hole extends between the patient-specific baseplate face and the second baseplate face.

According to a thirteenth aspect, the reverse shoulder arthroplasty implant system of the twelfth aspect or any other aspect, wherein the at least one peripheral fixation through-hole is designed to receive a peripheral fixation element.

Additionally, aspects of the present disclosure generally relate to reverse shoulder arthroplasty systems. According to a fourteenth aspect, the present disclosure relates to a reverse shoulder arthroplasty implant system comprising: a glenoid system for interfacing with anatomy of a patient, wherein the anatomy defines a Friedman's Line extending from a center of the patient's glenoid cavity to a medial end of the patient's scapula, the glenoid system comprising: a baseplate comprising a baseplate body, the baseplate body comprising: a patient-specific baseplate face comprising a periphery and positioned opposite a second baseplate face, the patient-specific baseplate face arranged and shaped to conformally engage with a bony surface of the anatomy; a patient-specific thickness that varies between 3-100 mm; a central post extending from the patient-specific baseplate face at a post angle and a post position, the post angle between about 2° to 80° with respect to the Friedman's Line; a taper extending from the second baseplate face at a taper angle and a taper position, the taper angle between about 2° to 80° with respect to the Friedman's Line; and one or more patient-specific regions comprising a textured surface; and a guide instrument comprising: a guide body comprising: a patient-specific guide face arranged and shaped to conformally engage with the bony surface; and a guide opening positioned on the patient-specific guide face at a guide opening position and a guide opening angle; and a handle connected to the guide face by a shaft, wherein a guide element is inserted through the handle to the guide opening; and a trial instrument comprising: a trial body comprising a patient-specific trial face and a second trial face positioned opposite the patient-specific trial face, the patient-specific trial face arranged and shaped to conformally engage with the bony surface; and a trial opening extending between the patient-specific trial face and the second trial face, the trial opening oriented at a trial opening position and a trial opening angle, wherein: the post angle, the guide opening angle, and the trial opening angle are substantially similar and are each measured with respect to the Friedman's Line; the post position, the guide opening position, and the trial opening position are substantially similar in relation to the bony surface; the post angle and the taper angle are different with respect to the Friedman's Line; and the post position and the taper position are offset by at least 1 mm.

According to a fifteenth aspect, the reverse shoulder arthroplasty implant system of the fourteenth aspect, or any other aspect, wherein the Friedman's Line represents an x-axis; a y-axis extends 90° from the Friedman's Line in a vertical direction; and a z-axis extends 90° degrees from the Friedman's Line in a horizontal direction.

According to a sixteenth aspect, the reverse shoulder arthroplasty implant system of the fifteenth aspect, or any other aspect, wherein the post angle is not parallel and not perpendicular to the x-axis.

According to a seventeenth aspect, the reverse shoulder arthroplasty implant system of the fifteenth aspect, or any other aspect, wherein the post angle is between about 10° and 45°.

According to an eighteenth aspect, the reverse shoulder arthroplasty implant system of the seventeenth aspect, or any other aspect, wherein the taper angle is not parallel and not perpendicular to the x-axis.

According to a nineteenth aspect, the reverse shoulder arthroplasty implant system of the seventeenth aspect, or any other aspect, wherein the taper angle is between about 10° and 45°.

Additionally, aspects of the present disclosure generally relate to reverse shoulder arthroplasty systems. According to a twentieth aspect, the present disclosure relates to a reverse shoulder arthroplasty implant system comprising: a glenoid system for interfacing with anatomy of a patient, wherein the anatomy defines a Friedman's Line extending from a center of the patient's glenoid cavity to a medial end of the patient's scapula, the glenoid system comprising: a baseplate comprising a baseplate body, the baseplate body comprising: a patient-specific baseplate face comprising a periphery and positioned opposite a second baseplate face, the patient-specific baseplate face arranged and shaped to conformally engage with a bony surface of the anatomy; a central post extending from the patient-specific baseplate face at a post angle and a post position, the post angle between about 2° to 80° with respect to the Friedman's Line; a taper extending from the second baseplate face at a taper angle and a taper position, the taper angle between about 2° to 80° with respect to the Friedman's Line; and one or more patient-specific regions comprising a textured surface; and a guide instrument comprising: a guide body comprising: a patient-specific guide face arranged and shaped to conformally engage with the bony surface; and a guide opening positioned on the patient-specific guide face at a guide opening position and a guide opening angle; and a handle connected to the guide face by a shaft, wherein a guide element is inserted through the handle to the guide opening; and a trial instrument comprising: a trial body comprising a patient-specific trial face and a second trial face positioned opposite the patient-specific trial face, the patient-specific trial face arranged and shaped to conformally engage with the bony surface; and a trial opening extending between the patient-specific trial face and the second trial face, the trial opening oriented at a trial opening position and a trial opening angle, wherein: the post angle, the guide opening angle, and the trial opening angle are substantially similar and are each measured with respect to the Friedman's Line; the post position, the guide opening position, and the trial opening position are substantially similar in relation to the bony surface; the post angle and the taper angle are different with respect to the Friedman's Line; and the post position and the taper position are offset by at least 1 mm.

Additionally, aspects of the present disclosure generally relate to reverse shoulder arthroplasty systems. According to a twenty-first aspect, the present disclosure relates to a guide instrument for use during a reverse arthroplasty procedure, the guide instrument comprising: a body for interfacing with anatomy of a patient, wherein the anatomy defines a Friedman's Line extending from a center of the patient's glenoid cavity to a medial end of the patient's scapula, the body comprising: a patient-specific guide face having a periphery, the patient-specific guide face arranged and shaped to conformally engage with a bony surface of the anatomy at a guide face angle, wherein a guide plane bisects the body at two representative points of the periphery, and the guide angle is between about 25° to 88° with respect to the guide plane and the Friedman's Line; a guide opening positioned on the patient-specific guide face at a guide opening position and a guide opening angle, the guide opening angle between about 2° to 80° with respect to the Friedman's Line; and an anti-rotation opening positioned on the body, the anti-rotation opening spaced away from the guide opening; a handle comprising a third opening, the third opening positioned at a distal end of the guide instrument; and a shaft extending between the body and a handle, the shaft defining a through-hole extending between the first opening and the third opening, wherein: a first guide element is inserted through the third opening to the guide opening, the first guide element colinear to a central axis of the shaft, and a second guide element is inserted through the anti-rotation opening.

According to a twenty-second aspect, the guide instrument of the twenty-first aspect, or any other aspect, wherein: the Friedman's Line represents an x-axis; a y-axis extends 90° from the Friedman's Line in a vertical direction; and a z-axis extends 90° degrees from the Friedman's Line in a horizontal direction.

According to a twenty-third aspect, the guide instrument of the twenty-second aspect, or any other aspect, wherein the two representative points comprise a first point on the periphery furthest from a center of the patient-specific guide face and a second point on the periphery closest to the center of the patient-specific guide face.

According to a twenty-fourth aspect, the guide instrument of the twenty-third aspect, or any other aspect, wherein the guide face angle is not parallel with respect to the x-axis.

According to a twenty-fifth aspect, the guide instrument of the twenty-fourth aspect, or any other aspect, wherein the guide face angle is not perpendicular with respect to the x-axis.

According to a twenty-sixth aspect, the guide instrument of the twenty-third aspect, or any other aspect, wherein the guide face angle is between about 30° and 80°.

According to a twenty-seventh aspect, the guide instrument of the twenty-sixth aspect, or any other aspect, wherein the body includes a patient-specific and varying thickness.

According to a twenty-eighth aspect, the guide instrument of the twenty-seventh aspect, or any other aspect, wherein the guide opening angle is not parallel and not perpendicular to the x-axis.

According to a twenty-ninth aspect, the guide instrument of the twenty-seventh aspect, or any other aspect, wherein the guide opening angle is between about 10° and 45°.

According to a thirtieth aspect, the guide instrument of the twenty-ninth aspect, or any other aspect, wherein the guide opening position is located to optimize placement of the first guide element into the bony surface, the guide opening position determined by the guide face angle and the guide opening angle.

According to a thirty-first aspect, the guide instrument of the thirtieth aspect, or any other aspect, wherein the handle comprises a fourth opening.

According to a thirty-second aspect, the guide instrument of the thirty-first aspect, or any other aspect, wherein the second guide element is inserted through the fourth opening.

According to a thirty-third aspect, the guide instrument of the thirtieth aspect, or any other aspect, wherein the body includes one or more apertures.

According to a thirty-fourth aspect, the guide instrument of the thirty-third aspect, or any other aspect, wherein the body includes one or more tabs disposed around the periphery.

According to a thirty-fifth aspect, the guide instrument of the thirtieth aspect, or any other aspect, wherein the patient-specific guide face comprises a textured surface.

According to a thirty-sixth aspect, the guide instrument of the thirty-fifth aspect, or any other aspect, wherein the textured surface comprises a porous structure.

According to a thirty-seventh aspect, the guide instrument of the thirty-sixth aspect, or any other aspect, wherein the porous structure is a gyroid structure.

Additionally, aspects of the present disclosure generally relate to reverse shoulder arthroplasty systems. According to a thirty-eighth aspect, the present disclosure relates to a trial for use during a reverse arthroplasty procedure, the trial comprising: a trial body for interfacing with anatomy of a patient, wherein the anatomy defines a Friedman's Line extending from a center of the patient's glenoid cavity to a medial end of the patient's scapula, the trial body comprising: a patient-specific trial face comprising a periphery and positioned opposite a second trial face, the patient-specific trial face arranged and shaped to conformally engage with a bony surface of the anatomy at a trial face angle, wherein a trial plane bisects the trial body at two representative points of the periphery, and the trial face angle is between about 25° to 88° with respect to the trial plane and the Friedman's Line; a third trial face extending between the patient-specific trial face and the second trial face along the periphery; a trial opening positioned on the patient-specific trial face at a trial opening position and a trial opening angle, the trial opening angle between about 2° to 80° with respect to the Friedman's Line; and a second opening positioned on the patient-specific trial face, the second opening spaced away from the trial opening, wherein the trial body is inserted over a first guide element using the trial opening and a second guide element using a second guide element.

According to a thirty-ninth aspect, the trial of the thirty-eighth aspect, or any other aspect, wherein the Friedman's Line represents an x-axis; a y-axis extends 90° from the Friedman's Line in a vertical direction; and a z-axis extends 90° degrees from the Friedman's Line in a horizontal direction.

According to a fortieth aspect, the trial of the thirty-ninth aspect, or any other aspect, wherein the two representative points comprise a first point on the periphery furthest from a center of the patient-specific trial face and a second point on the periphery closest to the center of the patient-specific trial face.

According to a forty-first aspect, the trial of the fortieth aspect, or any other aspect, wherein the trial face angle is not parallel with respect to the x-axis.

According to a forty-second aspect, the trial of the forty-first aspect, or any other aspect, wherein the trial face angle is not perpendicular with respect to the x-axis.

According to a forty-third aspect, the trial of the fortieth aspect, or any other aspect, wherein the trial face angle is between about 30° and 80°.

According to a forty-fourth aspect, the trial of the forty-third aspect, or any other aspect, wherein the trial body includes a patient-specific and varying thickness.

According to a forty-fifth aspect, the trial of the forty-third aspect, or any other aspect, wherein the trial opening angle measures is not parallel and not perpendicular to the x-axis.

According to a forty-sixth aspect, the trial of the forty-fourth aspect, or any other aspect, wherein the trial opening angle is between about 10° and 45°.

According to a forty-seventh aspect, the trial of the forty-sixth aspect, or any other aspect, wherein the trial opening position is located to optimize placement of the trial body over the first guide element and against the bony surface, the trial opening position determined by the trial face angle and the trial opening angle.

According to a forty-eighth aspect, the trial of the forty-seventh aspect, or any other aspect, wherein the third trial face is shaped to conformally engage with a portion of the bony surface.

According to a forty-ninth aspect, the trial of the forty-seventh aspect, or any other aspect, wherein a projection extends from the second face.

According to a fiftieth aspect, the trial of the forty-seventh aspect, or any other aspect, wherein the patient-specific trial face comprises a textured surface.

According to a fifty-first aspect, the trial of the fiftieth aspect, or any other aspect, wherein the textured surface comprises a porous structure.

According to a fifty-second aspect, the trial of the fifty-first aspect, or any other aspect, wherein the porous structure is a gyroid structure.

Additionally, aspects of the present disclosure generally relate to reverse shoulder arthroplasty systems. According to a fifty-third aspect, the present disclosure relates to a reverse shoulder arthroplasty implant system comprising: a glenoid system for interfacing with anatomy of a patient, wherein the anatomy defines a Friedman's Line extending from a center of the patient's glenoid cavity to a medial end of the patient's scapula, the glenoid system comprising: a baseplate comprising a baseplate body, the baseplate body comprising: a patient-specific baseplate face comprising a periphery and positioned opposite a second baseplate face, the patient-specific baseplate face arranged and shaped to conformally engage with a bony surface of the anatomy at a baseplate face angle, wherein a baseplate plane bisects the baseplate body at two representative points of the periphery, and the baseplate angle is measured between the baseplate plane and the Friedman's Line; a primary fixation element extending from the patient-specific baseplate face at a fixation angle and a fixation position; a protrusion extending from the second baseplate face at a protrusion orientation; and one or more patient-specific regions comprising a porous texture; and a guide instrument comprising: a guide body comprising: a patient-specific guide face arranged and shaped to conformally engage with the bony surface at a guide face angle; and a guide opening positioned on the patient-specific guide face at a guide opening position and a guide opening angle; a second opening positioned on the face and at the proximal end of the guide instrument, the second opening spaced away from the guide opening; and a handle connected to the guide body by a shaft; wherein: the baseplate face angle and the guide face angle are substantially similar and are each measured with respect to the baseplate plane and the Friedman's Line; the fixation angle and the guide opening angle are substantially similar and are each measured with respect to the Friedman's Line; the fixation position and the guide opening position are substantially similar in relation to the bony surface; a first guide element is inserted through the handle to the guide opening, the first guide element colinear to a central axis of the shaft; and a second guide element is inserted through the second opening.

According to a fifty-fourth aspect, the reverse shoulder arthroplasty implant system of the fifty-third aspect, or any other aspect, wherein: the Friedman's Line represents an x-axis; a y-axis extends 90° from the Friedman's Line in a vertical direction; and a z-axis extends 90° degrees from the Friedman's Line in a horizontal direction.

According to a fifty-fifth aspect, the reverse shoulder arthroplasty implant system of the fifty-fourth aspect, or any other aspect, wherein the two representative points comprise a first point on the periphery furthest from the center of the patient's glenoid cavity and a second point on the periphery closest to the center of the patient's glenoid cavity.

According to a fifty-sixth aspect, the reverse shoulder arthroplasty implant system of the fifty-fifth aspect, or any other aspect, wherein the baseplate face angle and the guide face angle each measure about between 30° and 80°.

According to a fifty-seventh aspect, the reverse shoulder arthroplasty implant system of the fifty-sixth aspect, or any other aspect, wherein the fixation angle and the guide opening angle each measure about between 10° and 45°.

According to a fifty-eighth aspect, the reverse shoulder arthroplasty implant system of the fifty-seventh aspect, or any other aspect, wherein the fixation position is located to optimize fixation of the primary fixation element into the bony surface, the fixation position determined by the baseplate face angle and the fixation angle.

According to a fifty-ninth aspect, the reverse shoulder arthroplasty implant system of the fifty-eighth aspect, or any other aspect, wherein the guide opening position is determined by the guide face angle and the guide opening angle.

According to a sixtieth aspect, the reverse shoulder arthroplasty implant system of the fifty-ninth aspect, or any other aspect, wherein the protrusion orientation comprises a protrusion angle and a protrusion position, the protrusion angle measured with respect to the Friedman's Line.

According to a sixty-first aspect, the reverse shoulder arthroplasty implant system of the sixtieth aspect, or any other aspect, wherein the protrusion angle measures about between 10° and 45°.

According to a sixty-second aspect, the reverse shoulder arthroplasty implant system of the sixty-first aspect, or any other aspect, wherein the protrusion position is defined by an offset distance from the fixation position.

According to a sixty-third aspect, the reverse shoulder arthroplasty implant system of the sixty-second aspect, or any other aspect, wherein the protrusion position is further defined by a minimum height and a minimum width of the second baseplate face.

Additionally, aspects of the present disclosure generally relate to reverse shoulder arthroplasty systems. According to a sixty-fourth aspect, the present disclosure relates to a reverse shoulder arthroplasty implant system comprising: a glenoid system for interfacing with anatomy of a patient, wherein the anatomy defines a Friedman's Line extending from a center of the patient's glenoid cavity to a medial end of the patient's scapula, the glenoid system comprising: a baseplate comprising a baseplate body, the baseplate body comprising: a patient-specific baseplate face comprising a periphery and positioned opposite a second baseplate face, the patient-specific baseplate face arranged and shaped to conformally engage with a bony surface of the anatomy at a baseplate face angle, wherein a baseplate plane bisects the baseplate body at two representative points of the periphery, and the baseplate angle is measured between the baseplate plane and the Friedman's Line; a primary fixation element extending from the patient-specific baseplate face at a fixation orientation, the fixation orientation comprising a fixation angle and a fixation position; a protrusion extending from the second baseplate face at a protrusion orientation; and one or more patient-specific regions comprising a porous texture; and a trial instrument comprising: a trial body comprising a patient-specific trial face and a second trial face positioned opposite the patient-specific trial face, the patient-specific trial face arranged and shaped to conformally engage with the bony surface at a trial face angle; a third trial face extending between the patient-specific trial face and the second trial face along an edge of the trial body; a trial opening extending between the patient-specific trial face and the second trial face, the trial opening oriented at a trial opening angle; and a second opening positioned on the patient-specific trial face, the second opening spaced away from the trial opening, wherein: the baseplate face angle and the trial face angle are substantially similar and are each measured with respect to the baseplate plane and the Friedman's Line; the fixation angle and the trial opening angle are substantially similar and are each measured with respect to the Friedman's Line; the fixation position and the trial opening position are substantially similar in relation to the bony surface; and the trial body is inserted over a first guide element using the trial opening and a second guide element using a second guide element.

According to a sixty-fifth aspect, the reverse shoulder arthroplasty implant system of the sixty-fourth aspect, or any other aspect, wherein the Friedman's Line represents an x-axis; a y-axis extends 90° from the Friedman's Line in a vertical direction; and a z-axis extends 90° degrees from the Friedman's Line in a horizontal direction.

According to a sixty-sixth aspect, the reverse shoulder arthroplasty implant system of the sixty-fifth aspect, or any other aspect, wherein the two representative points comprise a first point on the periphery furthest from the center of a patient-specific baseplate face and a second point on the periphery closest to the center of the patient-specific baseplate face.

According to a sixty-seventh aspect, the reverse shoulder arthroplasty implant system of the sixty-sixth aspect, or any other aspect, wherein the baseplate face angle and the trial face angle each measure about between 30° and 80°.

According to a sixty-eighth aspect, the reverse shoulder arthroplasty implant system of the sixty-seventh aspect, or any other aspect, wherein the fixation angle and the trial opening angle each measure about between 10° and 45°.

According to a sixty-ninth aspect, the reverse shoulder arthroplasty implant system of the sixty-eighth aspect, or any other aspect, wherein the fixation position is located to optimize fixation of the primary fixation element into the bony surface, the fixation position determined by the baseplate face angle and the fixation angle.

According to a seventieth aspect, the reverse shoulder arthroplasty implant system of the sixty-ninth aspect, or any other aspect, wherein the trial opening position is determined by the trial face angle and the trial opening angle.

According to a seventy-first aspect, the reverse shoulder arthroplasty implant system of the seventieth aspect, or any other aspect, wherein the protrusion orientation comprises a protrusion angle and a protrusion position, the protrusion angle measured with respect to the Friedman's Line.

According to a seventy-second aspect, the reverse shoulder arthroplasty implant system of the seventy-first aspect, or any other aspect, wherein the protrusion angle measures about 10° and 45°.

According to a seventy-third aspect, the reverse shoulder arthroplasty implant system of the seventy-second aspect, or any other aspect, wherein the protrusion position is defined by an offset distance from the fixation position.

According to a seventy-fourth aspect, the reverse shoulder arthroplasty implant system of the seventy-third aspect, or any other aspect, wherein the protrusion position is further defined by a minimum height and a minimum width of the second baseplate face.

Additionally, aspects of the present disclosure generally relate to reverse shoulder arthroplasty systems and techniques. According to a seventy-fifth aspect, the present disclosure relates to a process for installing a reverse shoulder arthroplasty system within anatomy of a patient, the process comprising: forming a bony surface of a glenoid of anatomy of a patient, wherein the anatomy defines a Friedman's Line extending from a center of the patient's glenoid cavity to a medial end of the patient's scapula; placing a guide onto the bony surface at a face angle, the face angle measured with respect to the Friedman's Line and an average plane of contact between the guide and the bony surface; inserting a primary pin into the bony surface at a fixation angle, wherein the fixation angle is measured with respect to the Friedman's Line and is not parallel and not perpendicular to the Friedman's Line; inserting an anti-rotation pin through the guide; placing a trial over the primary pin and the anti-rotation pin at the face angle; drilling over the primary pin to form an opening oriented along the fixation angle; placing a baseplate over the anti-rotation pin at the face angle, wherein a post of the baseplate extends into the opening at the fixation angle; drilling one or more peripheral holes into the bony surface; using one or more peripheral fixation screws to secure the baseplate to the bony surface; placing a glenosphere onto a taper of the baseplate, wherein an angle and a position of the taper are disconnected from the fixation angle and a position of the post; and inserting a humeral stem into a prepared humeral side of the patient.

Additionally, aspects of the present disclosure generally relate to reverse shoulder arthroplasty systems and techniques. According to a seventy-sixth aspect, the present disclosure relates to a surgical process comprising: exposing a patient's scapula according to a predetermined anatomical plan; connecting a pin guide to a scapula surface of the patient's scapula via one or more anchor components along a perimeter of the pin guide, the pin guide comprising: a pin guide body defining a first pin guide through hole and a second pin guide through hole; one or more patient-specific topographical features complementary to the scapula surface on a proximal surface of the pin guide body; and a handle extending distally from the pin guide body at a post angle other than 90 degrees with respect to a plane bisecting the pin guide body, wherein the first pin guide through hole extends through the handle; inserting a first pin through the handle via the first pin guide through hole and into the scapula surface; inserting a second pin through the second pin guide through hole and into the scapula surface; disconnecting the pin guide from the scapula surface by sliding the pin guide over the first pin and the second pin; connecting a trial to the scapula surface by sliding a trial over the first pin and second pin, the trial comprising a trial body: defining: a first trial through hole for receiving the first pin via the first trial through hole at the post angle; and a second trial through hole for receiving the second pin; comprising: the one or more patient-specific topographical features complementary to the scapula surface at a proximal end of the trial; and a trial body thickness between the proximal end and a distal end; disconnecting the trial from the scapula surface by sliding the trial over the first and second pin; creating a post hole in the scapula surface, the post hole at the post angle and based on the first pin; connecting a baseplate to the scapula surface by sliding the baseplate over the second pin and inserting a post into the post hole at the post angle, the baseplate: comprising: the post at the post angle; the one or more patient-specific topographical features complementary to the scapula surface at a proximal end of the baseplate; and a baseplate thickness between the proximal end and a distal end of the baseplate, the baseplate thickness substantially similar to the trial body thickness; defining a baseplate through hole for receiving the second pin; attaching the baseplate to the scapula surface via one or more fasteners.

According to a seventy-seventh aspect, the surgical process of the seventy-sixth aspect, or any other aspect, the process further comprises attaching a glenoid device to a mortise component extending from the distal end of the baseplate.

Additionally, aspects of the present disclosure generally relate to reverse shoulder arthroplasty systems and techniques. According to a seventy-eighth aspect, the present disclosure relates to a kit comprising: a pin guide comprising: a pin guide body defining a first pin guide through hole and a second pin guide through hole; one or more patient-specific topographical features complementary to a patient bony surface on a proximal surface of the pin guide body; and a handle extending distally from the pin guide body at a post angle other than 90 or 180 degrees relative to a reference line, wherein the first pin guide through hole extends through the handle; a trial comprising: a first trial through hole for receiving the first pin, the first trial through hole at the post angle; and a second trial through hole for receiving the second pin;

the one or more patient-specific topographical features complementary to the scapula surface at a proximal end of the trial; and a trial thickness between the proximal end and a distal end; and the baseplate comprising: a post at the post angle; the one or more patient-specific topographical features complementary to the scapula surface at a proximal end of the baseplate; a baseplate thickness between the proximal end and a distal end of the baseplate, the baseplate thickness substantially similar to the trial thickness; a baseplate through hole for receiving the second pin; and a taper on a distal end of the baseplate and at an angle other than the post angle.

Additionally, aspects of the present disclosure generally relate to reverse shoulder arthroplasty systems and techniques. According to a seventy-ninth aspect, the present disclosure relates to a reverse shoulder arthroplasty implant system comprising: a baseplate comprising a baseplate body, the baseplate body comprising: a patient-specific baseplate face comprising a periphery and positioned opposite a second baseplate face, the patient-specific baseplate face arranged and shaped to conformally engage with a bony surface of the anatomy at a baseplate face angle, wherein a baseplate plane bisects the baseplate body at two representative points of the periphery, and the baseplate angle is between about 25° to 88° with respect to the baseplate plane and the Friedman's Line; a central post extending from the patient-specific baseplate face at a post angle and a post position, the post angle between about 2° to 80° with respect to the Friedman's Line; a taper extending from the second baseplate face at a taper angle and a taper position, the taper angle between about 2° to 80° with respect to the Friedman's Line; and one or more patient-specific regions comprising a textured surface; and an opening extending from the patient-specific baseplate face to the second baseplate face and sized to accommodate both a peripheral fixation screw and a cannulated screw inserter, wherein: the post angle and the taper angle are different with respect to the Friedman's Line; and the post position and the taper position are offset by at least 1 mm.

Additionally, aspects of the present disclosure generally relate to reverse shoulder arthroplasty systems and techniques. According to an eightieth aspect, the present disclosure relates to a reverse shoulder arthroplasty implant system comprising: a glenoid system for interfacing with anatomy of a patient, wherein the anatomy defines a Friedman's Line extending from a center of the patient's glenoid cavity to a medial end of the patient's scapula, the glenoid system comprising: a baseplate comprising a baseplate body, the baseplate body comprising: a patient-specific baseplate face comprising a periphery and positioned opposite a second baseplate face, the patient-specific baseplate face arranged and shaped to conformally engage with a bony surface of the anatomy at a baseplate face angle, wherein a baseplate plane bisects the baseplate body at two representative points of the periphery, and the baseplate angle is between about 25° to 88° with respect to the baseplate plane and the Friedman's Line; a central post extending from the patient-specific baseplate face at a post angle and a post position, the post angle between about 2° to 80° with respect to the Friedman's Line; a taper extending from the second baseplate face at a taper angle and a taper position, the taper angle between about 2° to 80° with respect to the Friedman's Line; and one or more patient-specific regions comprising a textured surface; and a guide instrument comprising: a guide body comprising: a patient-specific guide face arranged and shaped to conformally engage with the bony surface at a guide face angle; and a guide opening positioned on the patient-specific guide face at a guide opening position and a guide opening angle; and a handle connected to the guide face by a shaft, wherein a guide element is inserted through the handle to the guide opening; and a trial instrument comprising: a trial body comprising a patient-specific trial face and a second trial face positioned opposite the patient-specific trial face, the patient-specific trial face arranged and shaped to conformally engage with the bony surface at a trial face angle; and a trial opening extending between the patient-specific trial face and the second trial face, the trial opening oriented at a trial opening angle, wherein: the baseplate face angle, the guide face angle, and the trial face angle are substantially similar angles with respect to the Friedman's Line; the post angle, the guide opening angle, and the trial opening angle are substantially similar and are each measured with respect to the Friedman's Line; the post position, the guide opening position, and the trial opening position are substantially similar in relation to the bony surface; the post angle and the taper angle are different with respect to the Friedman's Line; and the post position and the taper position are offset by at least 1 mm.

According to an eighty-first aspect, the reverse shoulder arthroplasty implant system of the eightieth aspect, or any other aspect, the Friedman's Line represents an x-axis; a y-axis extends 90° from the Friedman's Line in a vertical direction; and a z-axis extends 90° degrees from the Friedman's Line in a horizontal direction.

According to an eighty-second aspect, the reverse shoulder arthroplasty implant system of the eighty-first aspect, or any other aspect, wherein the two representative points comprise a first point on the periphery furthest from a center of the patient-specific baseplate face and a second point on the periphery closest to the center of the patient-specific baseplate face.

According to an eighty-third aspect, the reverse shoulder arthroplasty implant system of the eighty-second aspect, or any other aspect, wherein the baseplate face angle is not parallel to the x-axis.

According to an eighty-fourth aspect, the reverse shoulder arthroplasty implant system of the eighty-third aspect, or any other aspect, wherein the baseplate face angle is not perpendicular to the x-axis.

According to an eighty-fifth aspect, the reverse shoulder arthroplasty implant system of the eighty-second aspect, or any other aspect, wherein the baseplate face angle is between about 30° and 80°.

According to an eighty-sixth aspect, the reverse shoulder arthroplasty implant system of the eighty-fifth aspect, or any other aspect, wherein the post angle is not parallel and not perpendicular to the x-axis.

According to an eighty-seventh aspect, the reverse shoulder arthroplasty implant system of the eighty-fifth aspect, or any other aspect, wherein the post angle is between about 10° and 45°.

According to an eighty-eighth aspect, the reverse shoulder arthroplasty implant system of the eighty-seventh aspect, or any other aspect, wherein the taper angle is not parallel and not perpendicular to the x-axis.

According to an eighty-ninth aspect, the reverse shoulder arthroplasty implant system of the eighty-seventh aspect, or any other aspect, wherein the taper angle is between about 10° and 45°.

According to a ninetieth aspect, the reverse shoulder arthroplasty implant system of the eighty-ninth aspect, or any other aspect, wherein the post position is located to optimize fixation of the central post into the bony surface, the post position determined by the baseplate face angle and the post angle.

According to a ninety-first aspect, the reverse shoulder arthroplasty implant system of the ninetieth aspect, or any other aspect, wherein the taper position is defined by an offset distance from the post position.

According to a ninety-second aspect, the reverse shoulder arthroplasty implant system of the ninety-first aspect, or any other aspect, wherein the taper position is further defined by a minimum height and a minimum width of the second baseplate face.

According to a ninety-third aspect, the reverse shoulder arthroplasty implant system of the ninety-second aspect, or any other aspect, wherein the taper is designed to receive an inner portion of a glenosphere.

According to a ninety-fourth aspect, the reverse shoulder arthroplasty implant system of the ninety-third aspect, or any other aspect, wherein the inner surface of the glenosphere comprises a recession, the recession designed to receive the taper.

According to a ninety-fifth aspect, the reverse shoulder arthroplasty implant system of the ninety-fourth aspect, or any other aspect further comprising: a humeral stem system comprising: a liner designed to selectively engage with an outer surface of the glenosphere; a spacer tray; and a humeral stem.

According to a ninety-sixth aspect, the reverse shoulder arthroplasty implant system of the ninety-fifth aspect, or any other aspect, wherein the baseplate body further comprises a peripheral surface, the peripheral surface extending between the patient-specific baseplate face and the second baseplate face.

According to a ninety-seventh aspect, the reverse shoulder arthroplasty implant system of the ninety-sixth aspect, or any other aspect, wherein the baseplate body comprises a patient-specific and a thickness that varies between 3-100 mm.

According to a ninety-eighth aspect, the reverse shoulder arthroplasty implant system of the ninety-seventh aspect, or any other aspect, wherein at least one peripheral through-hole extends between the patient-specific baseplate face and the second baseplate face.

According to a ninety-ninth aspect, the reverse shoulder arthroplasty implant system of the ninety-eighth aspect, or any other aspect, wherein the at least one peripheral through-hole is designed to receive a peripheral fixation element.

According to a one hundredth aspect, the reverse shoulder arthroplasty implant system of the ninety-ninth aspect, or any other aspect, wherein the one or more patient-specific regions are disposed on at least one of the patient-specific baseplate face, the second baseplate face, the peripheral surface, or the primary fixation element.

According to a one hundred and first aspect, the reverse shoulder arthroplasty implant system of the eightieth aspect, or any other aspect, wherein the textured surface comprises a porous structure.

Additionally, aspects of the present disclosure generally relate to reverse shoulder arthroplasty systems and techniques. According to a one hundred and second aspect, the present disclosure relates to a surgical process comprising: exposing, via an end effector of a robot, a bony surface of a glenoid of anatomy of a patient, wherein the anatomy defines a Friedman's Line extending from a center of the patient's glenoid cavity to a medial end of the patient's scapula; determining, via the robot, an orientation of a baseplate on the bony surface; drilling an opening into the bony surface, the opening oriented along a fixation angle that is not parallel or perpendicular to the Friedman's Line; placing the baseplate on the bony surface such that a post of the baseplate extends into the opening at the fixation angle, the baseplate comprising: a patient-specific baseplate face comprising a periphery and positioned opposite a second baseplate face, the patient-specific baseplate face arranged and shaped to conformally engage with the bony surface at a baseplate face angle; the post extending from the patient-specific baseplate face at the fixation angle; a taper extending from the second baseplate face at a taper angle and a taper position, the taper angle between about 2° to 80° with respect to the Friedman's Line, wherein: the post angle and the taper angle are different with respect to the Friedman's Line; and the post position and the taper position are offset by at least 1 mm; drilling one or more peripheral holes into the bony surface; using one or more peripheral fixation screws to secure the baseplate to the bony surface; connecting a glenosphere to the taper of the baseplate; and inserting a humeral stem into a prepared humeral side of the patient.

According to a one hundred and third aspect, the surgical process of the one hundred and second aspect, or any other aspect, wherein: a baseplate plane bisects the baseplate body at two representative points of the periphery; and the baseplate face angle is between about 25° to 88° with respect to the baseplate plane and the Friedman's Line.

According to a one hundred and fourth aspect, wherein the robot processes a surgical plan comprising the fixation angle.

According to a one hundred and fifth aspect, the surgical process of the one hundred and second aspect, or any other aspect, wherein: the robot processes a post-operative representation of the anatomy of the patient; and the robot is configured to compare the post-operative representation of the anatomy of the patient to images of the baseplate as secured to the bony surface.

According to a one hundred and sixth aspect, the surgical process of the one hundred and second aspect, or any other aspect, wherein determining the orientation of the baseplate on the bony surface comprises using an instrument that at least partially registers the orientation of the baseplate on the bony surface.

According to a one hundred and seventh aspect, the surgical process of the one hundred and sixth aspect, or any other aspect, wherein the instrument comprises a pin guide.

According to a one hundred and eighth aspect, the surgical process of the one hundred and sixth aspect, or any other aspect, wherein the instrument comprises a baseplate trial.

According to a one hundred and ninth aspect, the surgical process of the one hundred and second aspect, or any other aspect, wherein determining the orientation of the baseplate on the bony surface comprises using a navigation system of the robot to determine the orientation of the baseplate on the bony surface.

According to a one hundred and tenth aspect, the surgical process of the one hundred and second aspect, or any other aspect, wherein determining the orientation of the baseplate on the bony surface comprises using a projected representation of the baseplate on the bony surface.

Additionally, aspects of the present disclosure generally relate to reverse shoulder arthroplasty systems and techniques. According to a one hundred and eleventh aspect, the present disclosure relates to a reverse shoulder arthroplasty implant system comprising: a baseplate comprising a baseplate body, the baseplate body comprising: a patient-specific baseplate face comprising a periphery and positioned opposite a second baseplate face, the patient-specific baseplate face arranged and shaped to conformally engage with a bony surface of the anatomy at a baseplate face angle, wherein a baseplate plane bisects the baseplate body at two representative points of the periphery, and the baseplate angle is between about 25° to 88° with respect to the baseplate plane and the Friedman's Line; a central post extending from the patient-specific baseplate face at a post angle and a post position, the post angle between about 2° to 80° with respect to the Friedman's Line; a taper extending from the second baseplate face at a taper angle and a taper position, the taper angle between about 2° to 80° with respect to the Friedman's Line; one or more patient-specific regions comprising a textured surface; an opening extending from the patient-specific baseplate face to the second baseplate face and sized to accommodate both a peripheral screw and a cannulated inserter; and an anti-rotation element disposed around a periphery of the opening on the second baseplate face, wherein: the opening is internally threaded; the post angle and the taper angle are different with respect to the Friedman's Line; and the post position and the taper position are offset by at least 1 mm.

According to a one hundred and twelfth aspect, the reverse shoulder arthroplasty implant system of the one hundred and eleventh aspect, or any other aspect, wherein the anti-rotation element is a hex-shaped indent.

Additionally, aspects of the present disclosure generally relate to reverse shoulder arthroplasty systems and techniques. According to a one hundred and thirteenth aspect, the present disclosure relates to a reverse shoulder arthroplasty implant system comprising: a glenoid system for interfacing with anatomy of a patient, wherein the anatomy defines a Friedman's Line extending from a center of the patient's glenoid cavity to a medial end of the patient's scapula, the glenoid system comprising: a baseplate comprising a baseplate body, the baseplate body comprising: a patient-specific baseplate face comprising a periphery and positioned opposite a second baseplate face, the patient-specific baseplate face arranged and shaped to conformally engage with a bony surface of the anatomy at a baseplate face angle, wherein a baseplate plane bisects the baseplate body at two representative points of the periphery, and the baseplate angle is between about 25° to 88° with respect to the baseplate plane and the Friedman's Line; a central post extending from the patient-specific baseplate face at a post angle and a post position, the post angle between about 2° to 80° with respect to the Friedman's Line; a taper extending from the second baseplate face at a taper angle and a taper position, the taper angle between about 2° to 80° with respect to the Friedman's Line; an anti-rotation element disposed around a periphery of an opening on the second baseplate face, extending from the patient-specific baseplate face to the second baseplate face and sized to accommodate both a peripheral screw and an inserter tool; one or more patient-specific regions comprising a textured surface; and the inserter tool comprising: a distal end designed to rotate and cause rotation of an externally threaded surface disposed on a proximal end, such that the proximal end selectively engages with the anti-rotation element to prevent the inserter tool from rotating, wherein: the opening is internally threaded; and the threaded surface mates with the opening to reversibly lock the inserter tool with the baseplate; the post angle and the taper angle are different with respect to the Friedman's Line; and the post position and the taper position are offset by at least 1 mm.

Additionally, aspects of the present disclosure generally relate to reverse shoulder arthroplasty systems and techniques. According to a one hundred and fourteenth aspect, the present disclosure relates to a surgical process for installing a reverse shoulder arthroplasty system within anatomy of a patient, the process comprising: exposing a bony surface of a glenoid of anatomy of a patient, wherein the anatomy defines a Friedman's Line extending from a center of the patient's glenoid cavity to a medial end of the patient's scapula; inserting a primary pin into the bony surface at a fixation angle, wherein the fixation angle is measured with respect to the Friedman's Line and is not parallel and not perpendicular to the Friedman's Line; inserting an anti-rotation pin into the bony surface; drilling over the primary pin to form an opening oriented along the fixation angle; engaging an inserter tool with a baseplate, the baseplate comprising an anti-rotation hole; using the inserter tool to place the baseplate over the anti-rotation pin, the anti-rotation pin passing through the anti-rotation hole, wherein a post of the baseplate extends into the opening at the fixation angle; drilling at least one peripheral hole into the bony surface; inserting a first peripheral screw into the at least one peripheral hole to secure the baseplate to the bony surface; disengaging the inserter tool from the baseplate; inserting a second peripheral screw into the anti-rotation hole and the bony surface; placing a glenosphere onto a taper of the baseplate, wherein an angle and a position of the taper are disconnected from the fixation angle and a position of the post; and inserting a humeral stem into a prepared humeral side of the patient.

According to a one hundred and fifteenth aspect, the surgical process of the one hundred and fourteenth aspect, or any other aspect, wherein the baseplate comprises an anti-rotation element disposed around a periphery of the anti-rotation hole.

According to a one hundred and sixteenth aspect, the surgical process of the one hundred and fifteenth aspect, or any other aspect, wherein the step of engaging an inserter tool with the baseplate comprises rotating a distal end of the inserter tool in a first direction to connect an externally threaded proximal end of the inserter tool with internal threading of the anti-rotation hole, and the anti-rotation element prevents the inserter tool from rotating.

According to a one hundred and seventeenth aspect, the surgical process of the one hundred and sixteenth aspect, or any other aspect, wherein the step of disengaging the inserter tool from the baseplate comprises rotating a distal end of the inserter tool in a second direction to detach the externally threaded proximal end from the internal threading of the anti-rotation hole, and the anti-rotation element prevents the inserter tool from rotating.

Additionally, aspects of the present disclosure generally relate to reverse shoulder arthroplasty systems and techniques. According to a one hundred and eighteenth aspect, the present disclosure relates to a surgical process for installing a reverse shoulder arthroplasty system within anatomy of a patient, the process comprising: exposing a bony surface of a glenoid of anatomy of a patient, wherein the anatomy defines a Friedman's Line extending from a center of the patient's glenoid cavity to a medial end of the patient's scapula; inserting an anti-rotation pin into the bony surface; forming an opening in the bony surface, the opening oriented along the fixation angle, wherein the fixation angle is measured with respect to the Friedman's Line and is not parallel and not perpendicular to the Friedman's Line; engaging an inserter tool with a baseplate; using the inserter tool to place the baseplate over the anti-rotation pin at a face angle, the anti-rotation pin passing through an anti-rotation hole formed by the baseplate and the face angle measured with respect to the Friedman's Line and an average plane of contact between the baseplate and the bony surface, wherein a post of the baseplate extends into the opening at the fixation angle; drilling at least one peripheral hole into the bony surface; inserting a first peripheral screw into the at least one peripheral hole to secure the baseplate to the bony surface; disengaging the inserter tool from the baseplate; inserting a second peripheral screw into the anti-rotation hole and bony surface; placing a glenosphere onto a taper of the baseplate, wherein an angle and a position of the taper are disconnected from the fixation angle and a position of the post.

According to a one hundred and nineteenth aspect, the surgical process of the one hundred and eighteenth aspect, or any other aspect, or any other aspect, wherein the baseplate comprises an anti-rotation element disposed around a periphery of the anti-rotation hole.

According to a one hundred and twentieth aspect, the surgical process of the one hundred and nineteenth aspect, wherein the step of engaging an inserter tool with the baseplate comprises rotating a distal end of the inserter tool in a first direction to connect an externally threaded proximal end of the inserter tool with internal threading of the anti-rotation hole, and the anti-rotation element prevents the inserter tool from rotating.

According to a one hundred and twenty-first aspect, the surgical process of the one hundred and twentieth aspect, or any other aspect, wherein the step of disengaging the inserter tool from the baseplate comprises rotating a distal end of the inserter tool in a second direction to detach the externally threaded proximal end from the internal threading of the anti-rotation hole, and the anti-rotation element prevents the inserter tool from rotating.

According to a one hundred and twenty-second aspect, the present disclosure relates to a reverse shoulder arthroplasty implant system comprising: a glenoid system for interfacing with anatomy of a patient, the glenoid system comprising: a baseplate comprising a baseplate body, the baseplate body comprising: a patient-specific baseplate face comprising a periphery and positioned opposite a second baseplate face, the patient-specific baseplate face arranged and shaped to conformally engage with a bony surface of the anatomy at a baseplate face angle, wherein a baseplate plane bisects the baseplate body at two representative points of the periphery, and the baseplate angle is calculated to be within a first predetermined design envelope between about 25° to 88° with respect to the baseplate plane and an anatomical reference; a central post extending from the patient-specific baseplate face at a post angle and a post position, the post angle within a second predetermined design envelope and between about 2° to 80° with respect to the anatomical feature; a taper extending from the second baseplate face at a taper angle and a taper position, the taper angle within a third predetermined envelope and between about 2° to 80° with respect to the anatomical feature; an anti-rotation element disposed around a periphery of an opening on the second baseplate face, extending from the patient-specific baseplate face to the second baseplate face and sized to accommodate both a peripheral screw and an inserter tool; one or more patient-specific regions comprising a textured surface; and the inserter tool comprising: a distal end designed to rotate and cause rotation of an externally threaded surface disposed on a proximal end, such that the proximal end selectively engages with the anti-rotation element to prevent the inserter tool from rotating, wherein: the opening is internally threaded; and the threaded surface mates with the opening to reversibly lock the inserter tool with the baseplate; the post angle and the taper angle are different with respect to the anatomical reference; and the post position and the taper position are offset by at least 1 mm.

According to a one hundred and twenty-third aspect, the present disclosure relates to a reverse shoulder arthroplasty implant system comprising: a glenoid system for interfacing with anatomy of a patient, the glenoid system comprising: a baseplate comprising a baseplate body, the baseplate body comprising: a patient-specific baseplate face comprising a periphery and positioned opposite a second baseplate face, the patient-specific baseplate face arranged and shaped to conformally engage with a bony surface of the anatomy; a central post extending from the patient-specific baseplate face at a post angle and a post position, the post angle within a first predetermined design envelope and between about 2° to 80° with respect to an anatomical feature of the patient; a taper extending from the second baseplate face at a taper angle and a taper position, the taper angle within a second predetermined envelope and between about 2° to 80° with respect to the anatomical feature; an anti-rotation element disposed around a periphery of an opening on the second baseplate face, the opening extending from the patient-specific baseplate face to the second baseplate face and sized to accommodate both a peripheral screw and an inserter tool; one or more patient-specific regions comprising a textured surface; and the inserter tool comprising: a distal end designed to rotate and cause rotation of an externally threaded surface disposed on a proximal end, such that the proximal end selectively engages with the anti-rotation element to prevent the inserter tool from rotating, wherein: the opening is internally threaded; and the threaded surface mates with the opening to reversibly lock the inserter tool with the baseplate; the post angle and the taper angle are different with respect to the anatomical reference; and the post position and the taper position are offset by at least 1 mm.

According to a one hundred and twenty-fourth aspect, the present disclosure relates to a reverse shoulder arthroplasty implant kit comprising: a pin guide comprising one or more windows and at least one feature customized to a patient's anatomy; a baseplate comprising: one or more drill guides screwed into one or more first peripheral screw holes that extend through the baseplate; an anti-rotation element disposed around a periphery of a dual purpose opening on the second baseplate face, the dual purpose opening extending through the baseplate body and sized to accommodate both a second peripheral screw and an inserter tool; the inserter tool comprising: a distal end designed to rotate and cause rotation of an externally threaded surface disposed on a proximal end, such that the proximal end selectively engages with the anti-rotation element to prevent the inserter tool from rotating, wherein the opening is internally threaded and the threaded surface mates with the opening to reversibly lock the inserter tool with the baseplate; and a representative model of the patient's anatomy comprising visual representations of a plurality of screws that extend through each of the one or more first peripheral screw holes and the second screw hole.

It will be understood by those skilled in the art that one or more aspects of this disclosure can meet certain objectives, while one or more other aspects can lead to certain other objectives. Various modifications to the illustrated embodiments will be readily apparent to those skilled in the art, and the generic principles herein can be applied to other embodiments and applications without departing from embodiments of the disclosure. Other objects, features, benefits, and advantages of the present disclosure will be apparent in this summary and descriptions of the disclosed embodiments, and will be readily apparent to those skilled in the art. Such objects, features, benefits, and advantages will be apparent from the above as taken in conjunction with the accompanying figures and all reasonable inferences to be drawn therefrom.

DETAILED DESCRIPTION

Figure 1:
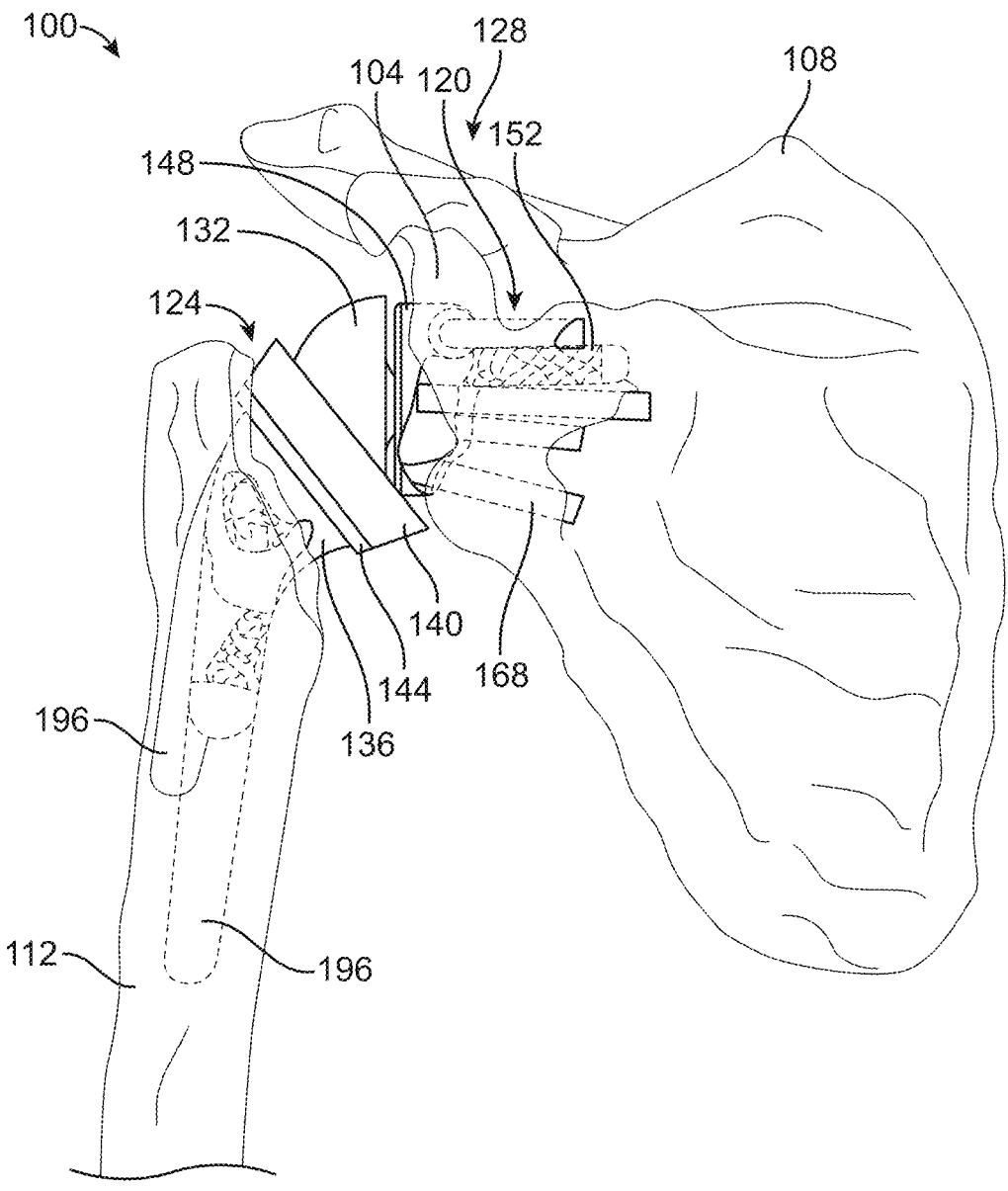
FIG. 1 is a side view of an exemplary reverse shoulder arthroplasty (RSA) implant system installed in a patient, according to at least one embodiment.

In one embodiment, the shoulder implants discussed herein may be installed in patients with varying degrees of shoulder damage. In at least one embodiment, a method of conducting a reverse shoulder arthroplasty (RSA) procedure comprises the installation of a humeral stem into the humerus of a patient, and a baseplate attached to a glenosphere into the glenoid cavity of the patient. The baseplate may include a post and a patient-specific surface configured to mate with a bony surface of the patient anatomy.

In a particular embodiment, a surgeon performing the installation of the humeral stem and the baseplate may make use of instruments designed to facilitate placement of the implant components within the patient anatomy. For example, a method of implantation of the implant components may first comprise placement of one or more pins in the patient's scapula. The placement of the one or more pins may be guided with the use of a pin guide. The pins may act as references for the insertion of a baseplate trial, which may be configured to model the baseplate, and soft tissue and/or cartilage of the glenoid cavity may be iteratively removed after one or more fittings of the baseplate trial to ensure a proper fit. The method may further comprise steps of preparing the implantation site for the baseplate post via drilling and subsequently inserting the baseplate into the glenoid cavity of the scapula. The method may additionally comprise steps of fixating the baseplate using one or more peripheral fixation screws and attaching a glenosphere to a taper of the baseplate to enable shoulder articulation.

Any one or more of the implant components used in the reverse shoulder arthroplasty method may be patient-specific, and components such as the pin guide, the baseplate trial, and the baseplate may feature surfaces or shapes that are uniquely designed to mimic or mate to the patient's anatomy. As described herein, examples of implant components comprising different features for different patient anatomy are provided to display the customization allowed by the disclosed systems and processes.

As will be understood, while various aspects and embodiments are described herein, additional aspects, features, and methodologies of the claimed systems, implants, instruments, and methods will be readily discernible from the description herein, by those of ordinary skill in the art. Many embodiments and adaptations of the disclosure and claimed embodiments other than those herein described, as well as many variations, modifications, and equivalent arrangements and methodologies, will be apparent from or reasonably suggested by the disclosure and the foregoing description thereof, without departing from the substance or scope of the claims.

The present systems provide a novel advantage over prior systems: the taper and post (and/or other features) are "disconnected." In various embodiments, the taper, and thus the location and angle of the glenosphere, and post (and other features) can be independently and optimally designed for a specific patient's anatomy. The systems described herein include novel taper and post locations and angles to maximize use of dense bone of a patient or other considerations to provide an improved patient outcome.

Figure 2:
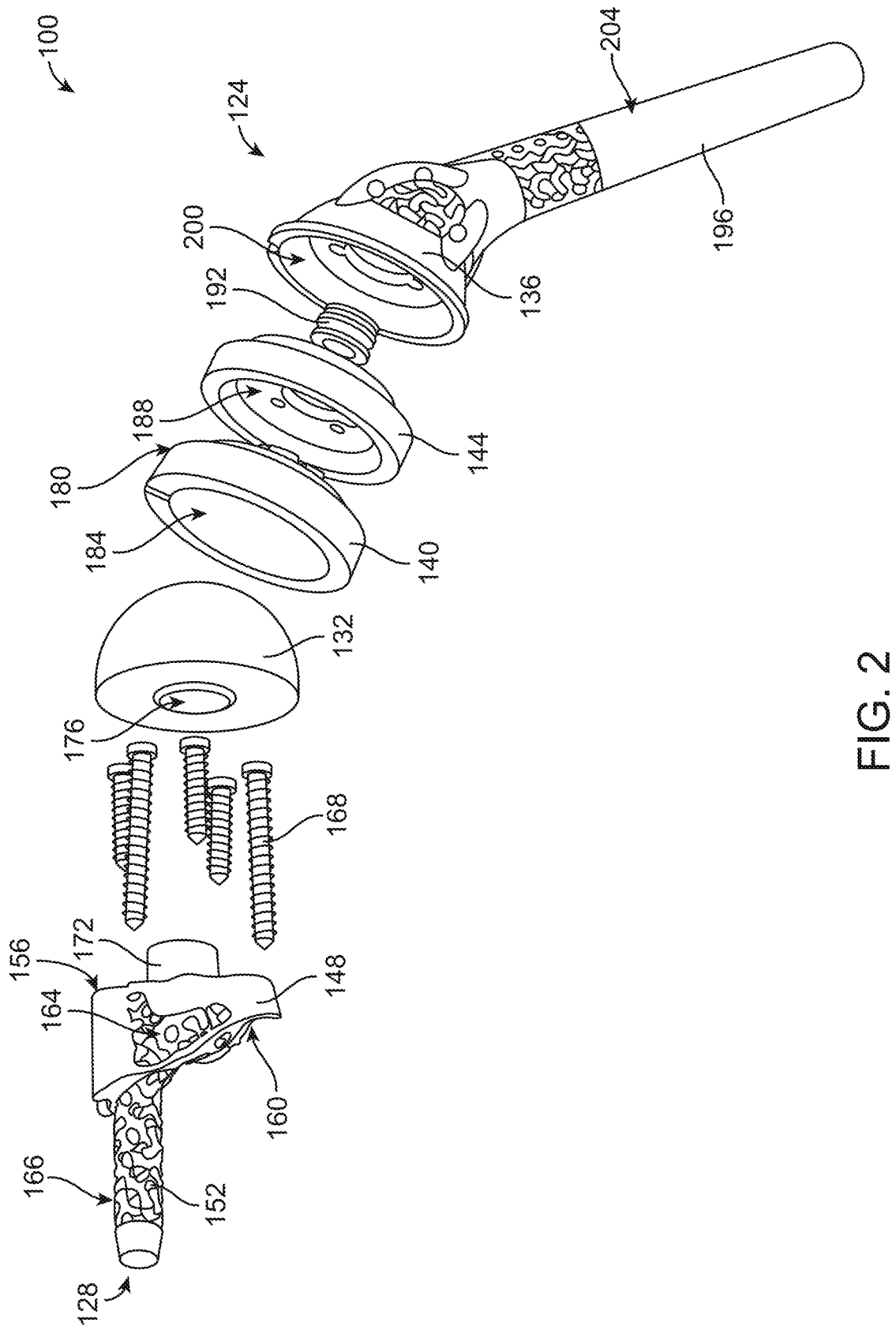
FIG. 2 is an exploded view of an exemplary RSA implant system, according to at least one embodiment.
Figure 55:
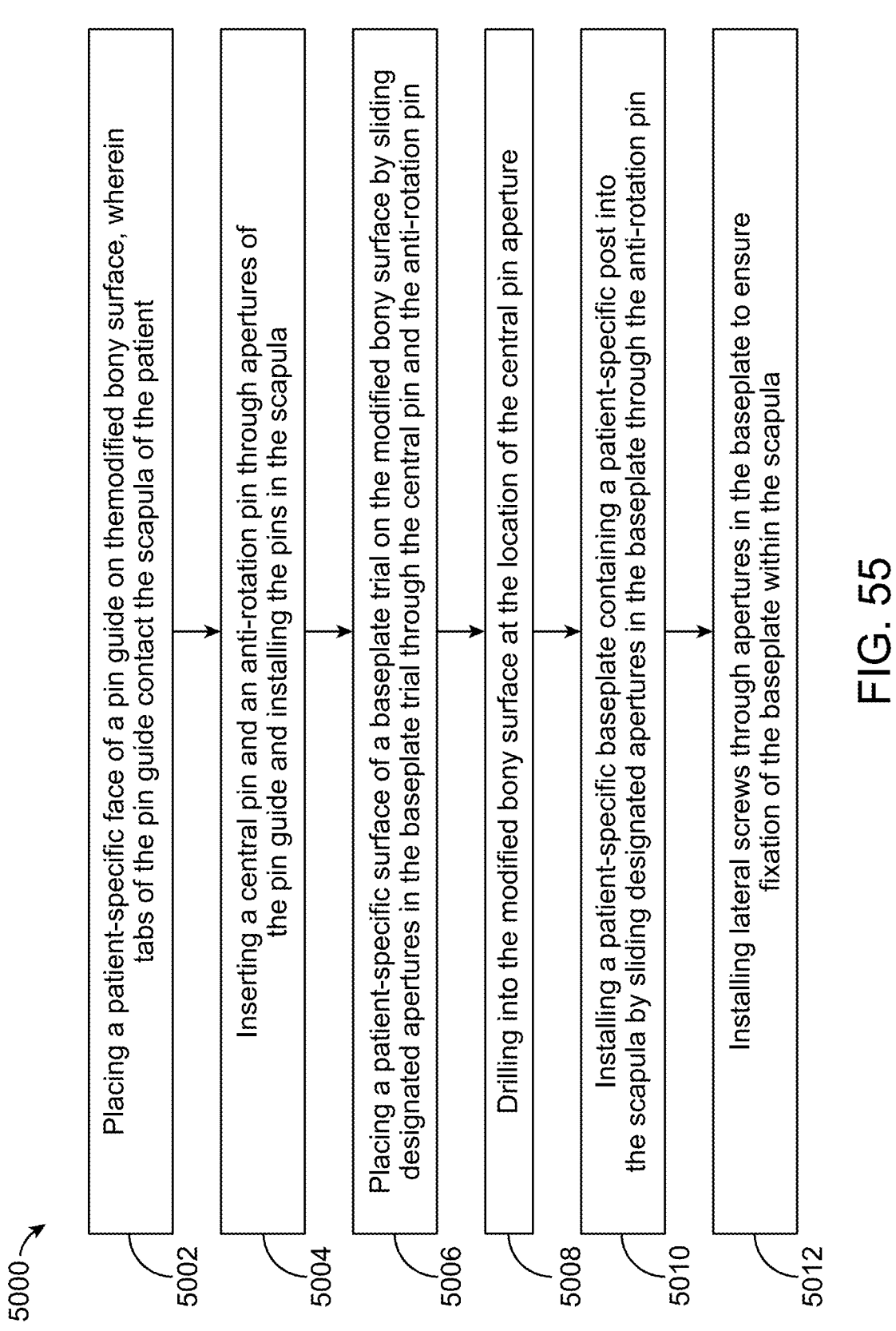
FIG. 55 is a flowchart depicting a method of performing an RSA procedure, according to at least one embodiment.
Figure 56:
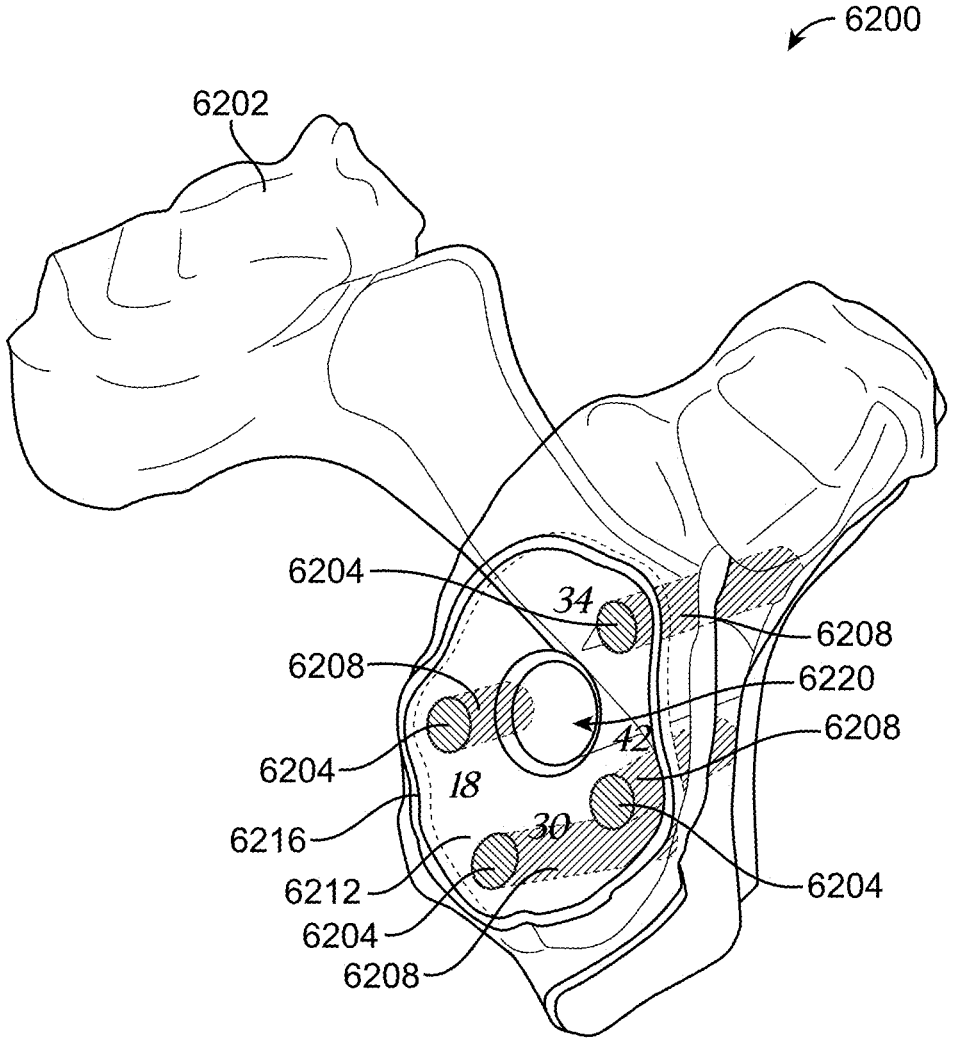
FIG. 56 is a perspective view of a three-dimensionally printed representation of patient anatomy and peripheral fixation screws, according to at least one embodiment.
Figure 57:
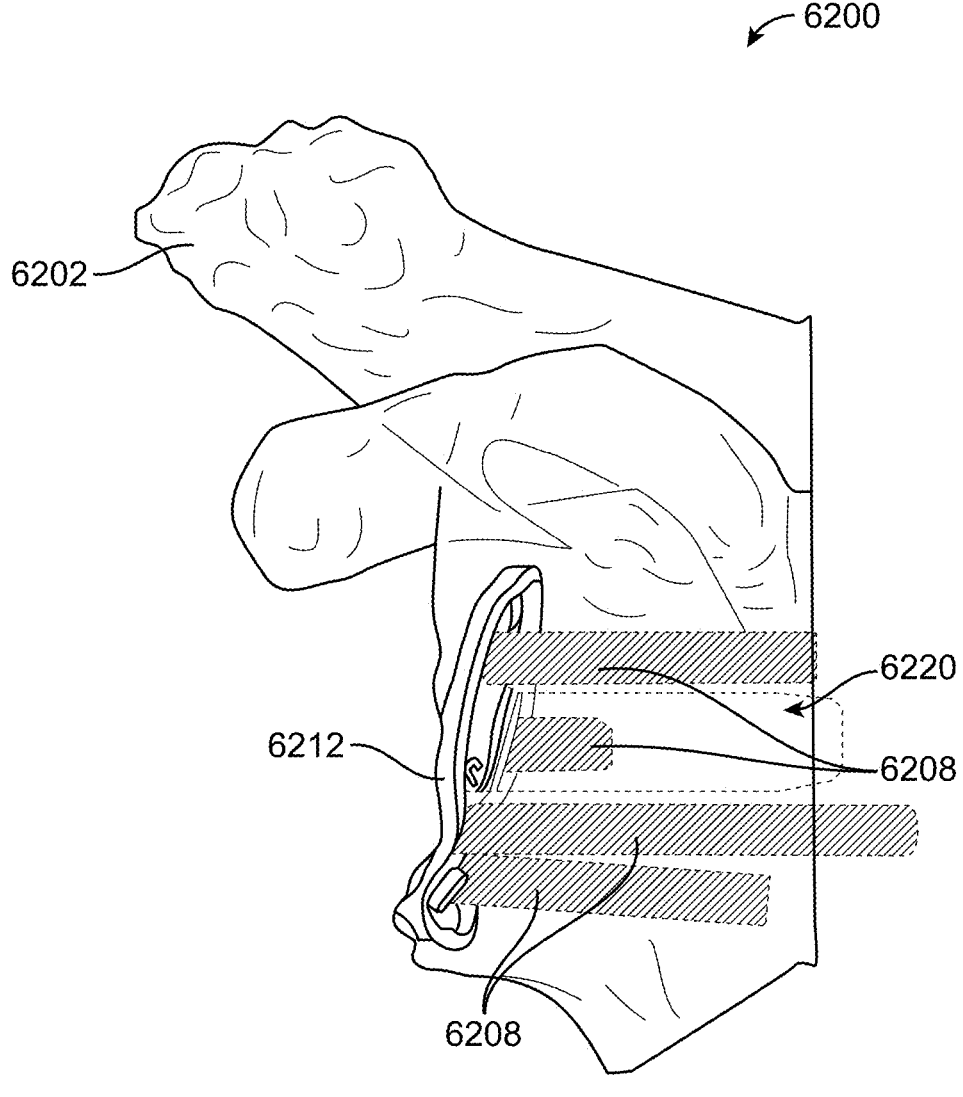
FIG. 57 is a side view of a three-dimensionally printed representation of patient anatomy and peripheral fixation screws, according to at least one embodiment.

FIGS. 1 and 2 show an exemplary implant assembly for a patient undergoing a reverse shoulder arthroplasty procedure. FIGS. 3-40 show an exemplary patient specific system according to a specific surgical plan. FIGS. 41-48 show select features of a second and third patient specific system according to a second and third surgical plan. FIGS. 49-54 show select features of a fourth patient specific system according to a fourth surgical plan. FIG. 55 displays an exemplary method of performing an RSA procedure using components of the patient-specific systems. FIGS. 56 and 57 illustrate exemplary three-dimensionally printed patient anatomy for visualization of the surgical site. The present disclosure is not limited to the embodiments discussed and it will be understood from discussions herein that the figures and descriptions are exemplary and features of one component may be used with a different component.

FIG. 1 shows an exemplary reverse shoulder implant assembly 100 installed in the glenoid cavity 104 of a patient's scapula 108 and humerus 112, according to one embodiment. In various embodiments, the glenoid cavity 104 contains a bony surface 120, which may be modified by the surgeon in any suitable way to allow for the implant assembly 100 to be installed (e.g., a surgeon may remove or modify tissue to remove damaged, injured, or diseased tissue, or remove soft tissue that will not be utilized post-surgery). In at least one embodiment, the implant assembly 100 is provided in the form of a humeral stem system 124 and a glenoid system 128. The humeral stem system 124 may generally include a stem 136 comprising one or more shafts 196, a liner 140, and an optional spacer tray 144. The glenoid system 128 may generally include a baseplate 148, a post 152, one or more peripheral fixation screws 168, and a glenosphere 132.

According to one embodiment and as will be understood from discussions herein, the liner 140 may act as a socket and the glenosphere 132 may act as the ball in the shoulder of a patient. The glenosphere 132 may articulate with the liner 140 such that the patient may perform an expected range of motion.

Referring now to FIG. 2, an exploded view of the implant assembly 100 of FIG. 1 is shown. According to one embodiment, the implant assembly 100 may include the glenoid system 128, which includes the baseplate 148, one or more peripheral fixation screws 168, and the glenosphere 132. As discussed above in FIG. 1, in at least one embodiment, the RSA system may also include the humeral stem system 124, which includes a humeral stem 136, the liner 140, and a spacer tray 144.

In at least one embodiment, the baseplate 148 includes a post 152, a back surface 156, a patient-specific surface 160, side surfaces 164, and a taper 172. In one embodiment, one or more of the back surface 156, the patient-specific surface 160, and side surfaces 164 may be fully solid, fully porous, partially porous, or hollow. Any of the surfaces of the baseplate (or humeral stem system), including the surface 166 of the post 152 may additionally feature porous regions—such as a sheet-based triply periodic, minimal surface (TPMS) gyroid structure—that may improve the in-growth potential between bone and other tissues with the post 152.

The post 152 may include a tip and a shaft and may provide structural support for fixation of the remainder of the glenoid system 128 within the patient's anatomy. As will be understood, the length, orientation, and angle of the post 152 may be customized to the patient to ensure optimal placement and fixation in the scapula 108. The degree of porosity of the surface 166 of the post 152 may also facilitate bone growth in the patient, which may, in one example, depend upon a degree of bone loss in the patient's shoulder. In one embodiment, the baseplate 148 and the post 152 may be integrally formed. In another embodiment, the baseplate 148 and the post 152 may be coupled. In further embodiments, the post may take the form of another structural component, such as a screw (e.g., with or without porosity). In yet another embodiment, the post 152 may be modularly constructed such that the post 152 is assembled during installation in the glenoid cavity 104.

The patient-specific surface 160 of the baseplate 148 may be designed to mimic one or more details of a bony surface 120 of the patient's glenoid cavity 104 where the glenoid system 128 will be installed. In one embodiment, the patient-specific surface 160 is substantially perpendicular to the post 152. In another embodiment, the patient-specific surface 160 is inclined such that augment thicknesses of the side surfaces 164 of the baseplate vary along the perimeter of the baseplate 148.

The taper 172 may be a protrusion extending away from the baseplate 148, according to one embodiment. The taper 172 may be configured to accept and couple the glenosphere 132 to the baseplate 148. Thus, in various embodiments, the taper is provided in the form of a self-locking taper. For example, in one embodiment, the glenosphere 132 can be press-fitted onto the taper 172. The taper may alternatively be provided in the form of a Jacobs, Jamo, Brown & Sharpe, HSK, NMTB, B, or morse taper as appropriate. In another embodiment, the taper 172 may feature external threads (not shown) designed to mate with internal female threads in an aperture 176 of the glenosphere 132. The glenosphere 132 and the taper 172 may additionally be coupled prior to installation in the patient, and the taper 172 may be coupled to the glenosphere 132 via the aperture 176 through the use of an adhesive, welding, fixator, or other attachment methods.

The peripheral fixation screws 168 may be inserted into apertures in the baseplate 148 to fix the glenoid system 128 to the underlying patient scapula 108 in order to increase stability of the exemplary reverse shoulder implant assembly 100. The length of the one or more peripheral fixation screws 168 may be designed in accordance with the degree of bone loss, available bone, or bone density of the patient and condition of the scapula 108. In one embodiment, the system may include any suitable number of screws, including one screw, two screws, three screws, four screws, or ten screws, to ensure fixation of the glenoid system 128 in the scapula 108. In one such embodiment, all of the peripheral fixation screws 168 installed in a patient are of the same length and diameter. In another embodiment, each peripheral fixation screw 168 of the peripheral fixation screws 168 is of a unique length and/or diameter chosen based on installation location and/or available bone. As will be understood from discussions herein, the peripheral fixation screws 168 may be integrally formed with the glenoid system 128 (e.g., 3D-printed with the post 152 and glenoid system 128) or may be attached separately. The peripheral fixation screws 168 may additionally include porosity, such as any or all of the porous features discussed herein, to increase bony ingrowth, or may be screws without any porous features.

As will be understood from discussions herein, the baseplate 148 may include one or more holes or openings for receiving peripheral fixation screws 168. In various embodiments, such holes or openings are oriented such that each of the peripheral fixation screws 168 extends into the scapula of a patient at a specific, predetermined angle. In at least one embodiment, the orientation of a particular hole or opening is based on a corresponding peripheral fixation screw 168 angle. For example, if a surgical plan calls for a peripheral fixation screw 168 to extend into the scapula of a patient at 89 degrees from a sagittal plane (e.g., sagittal plane 1048 in FIG. 3), then a longitudinal axis extends from a center of the particular hole or opening at 89 degrees from the sagittal plane.

The glenosphere 132, while typically hemispherical, may feature eccentricity depending upon an individual patient's needs. The size of the glenosphere 132 may be created depending on the individual patient's anatomy. In one embodiment, the glenosphere 132 may have a diameter between 26 mm and 50 mm, or between 30 mm and 48 mm, or between 36 and 44 mm, or between 38 mm and 42 mm, or any other suitable diameter in accordance with the principles of this disclosure. In one embodiment, the glenosphere 132 may be constructed of a polymeric material, such as polyethylene. Smaller diameter glenospheres (or any glenosphere) 132 may comprise metals or metallic alloys including but not limited to cobalt, chromium, titanium, and stainless steel. In one embodiment, the glenosphere 132 and the baseplate 148 of the glenoid system 128 may be integrally formed. In another embodiment, the glenosphere 132 and the baseplate 148 of the glenoid system 128 may be coupled before, during, or after installation in the patient.

Turning now to the humeral stem system 124, in a particular embodiment, the humeral stem system 124 includes the liner 140, a spacer tray 144, and a humeral stem 136 that may be installed in the humerus 112. The humeral stem 136 may comprise one or more shafts 196 and an opening 200 to accept or otherwise interface with the spacer tray 144.

In one embodiment, the liner 140 comprises a concave surface 180 and an interior volume 184. The interior volume 184 may have a diameter substantially similar to that of the glenosphere 132 such that upon contact, the liner 140 may couple smoothly to the surface of the glenosphere 132 and allow a wide range of motion for the patient. In various embodiments, the liner 140 is constructed of a polymeric material, such as polyethylene, and may feature protrusions to accept the spacer tray 144.

The spacer tray 144 may be optionally coupled to the liner 140 to adjust the placement of the liner 140 with respect to the glenosphere 132. In various embodiments, the spacer tray 144 features an interior volume 188, with a diameter substantially similar to the diameter of the liner 140. In another embodiment, the spacer tray 144 (or the functionality thereof) is integral to the humeral stem 136.

In an additional embodiment, the spacer tray 144 further includes a connecting member 192 containing male threads to couple the spacer tray 144 to the humeral stem 136 via screwing into the opening 200 of the humeral stem 136. In other embodiments, where the connecting member 192 is omitted, the spacer tray 144 may comprise a connecting surface (not depicted), configured to sit within the opening 200 of the humeral stem 136. The connecting surface may comprise a tapered edge.

The humeral stem 136 may include a plurality of shafts 196 installed within the humerus 112. In another embodiment, the humeral stem 136 may comprise only one shaft 196 installed along a longitudinal axis of the humerus 112. In one embodiment, a surface 204 of the humeral stem 136 includes porosity that may osteointegrate within the patient's humerus 112.

According to the principles of this disclosure, any one or more of the components of the implant assembly 100 may be customized for a patient. Customization of the implant assembly 100 may include variation in the length, width, diameter, composition, porosity, angular orientation, weight, and location of installation, of any one or more of the components of the implant assembly 100. Furthermore, in one embodiment, a surgeon may select to exclude a component based on any number of factors of the patient's anatomy, including, but not limited to, the patient's degree of shoulder injury, bone size or density, pain tolerance, etc. Additional components that are not displayed may also be included within or along with the implant assembly 100 to ensure proper recovery of the patient. Further, in one embodiment, one or more of the components of the implant assembly 100 may be packaged and/or sterilized and distributed to the surgeon performing the RSA procedure.

Prior to implantation of any of the components of the implant assembly 100, the implant site(s) may be prepared for surgery. The implant site may include the bony surface 120 of the patient, any area of the scapula 108 that would make contact with the baseplate 148, and any other surrounding areas. The bony surface 120 may include portions of the scapula 108 that are injured, diseased, weak, structurally deficient, or deformed prior to surgery. As would be understood by one skilled in the art, the bony surface 120 of the scapula 108 may in some embodiments be modified, such as by removal of cartilage, soft tissue, or bone, such that the bony surface 120 may be optimized for interaction with the glenoid system 128.

Figure 3:
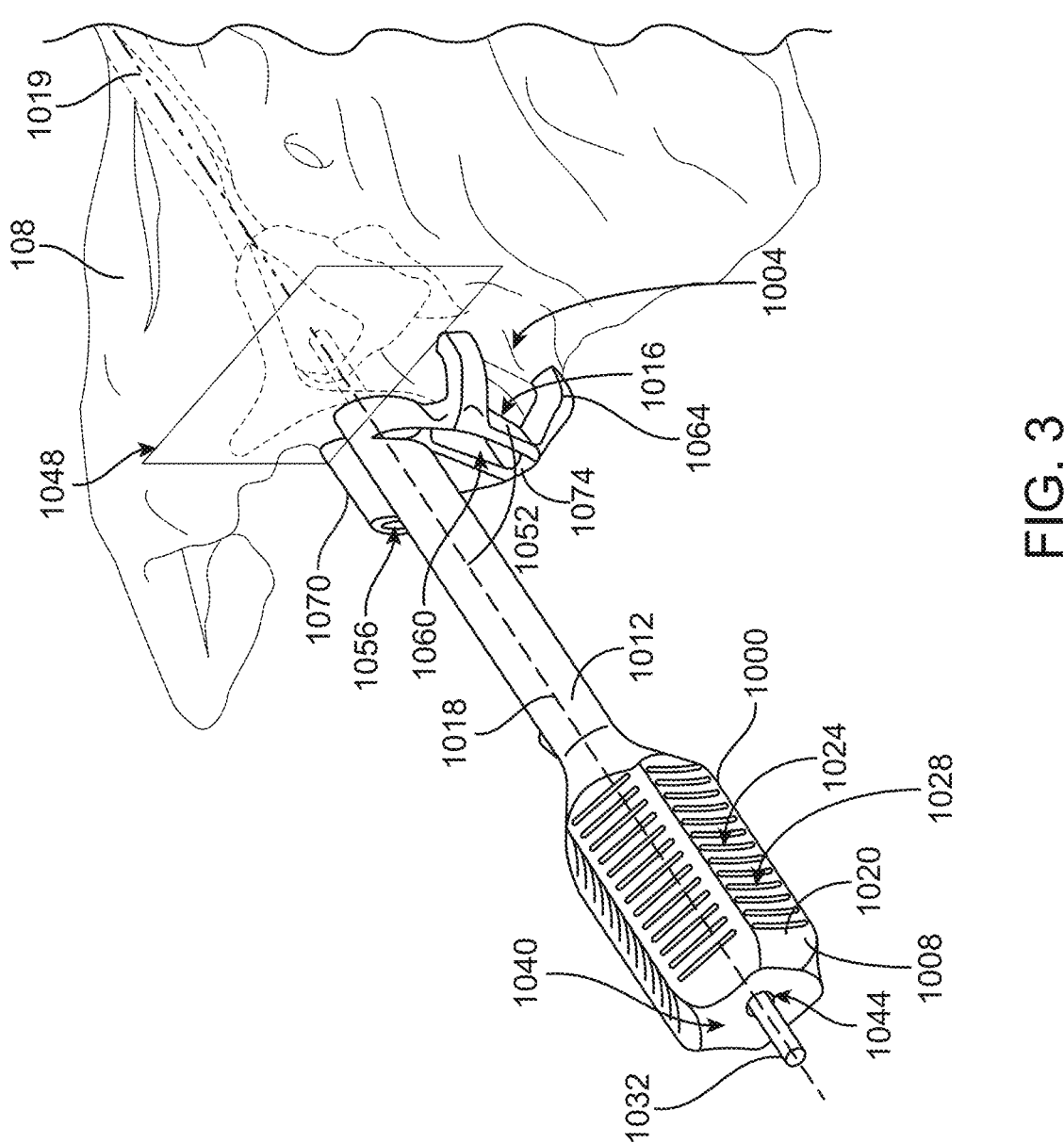
FIG. 3 is a perspective view of an exemplary pin guide interacting with patient anatomy, according to at least one embodiment.
Figure 4:
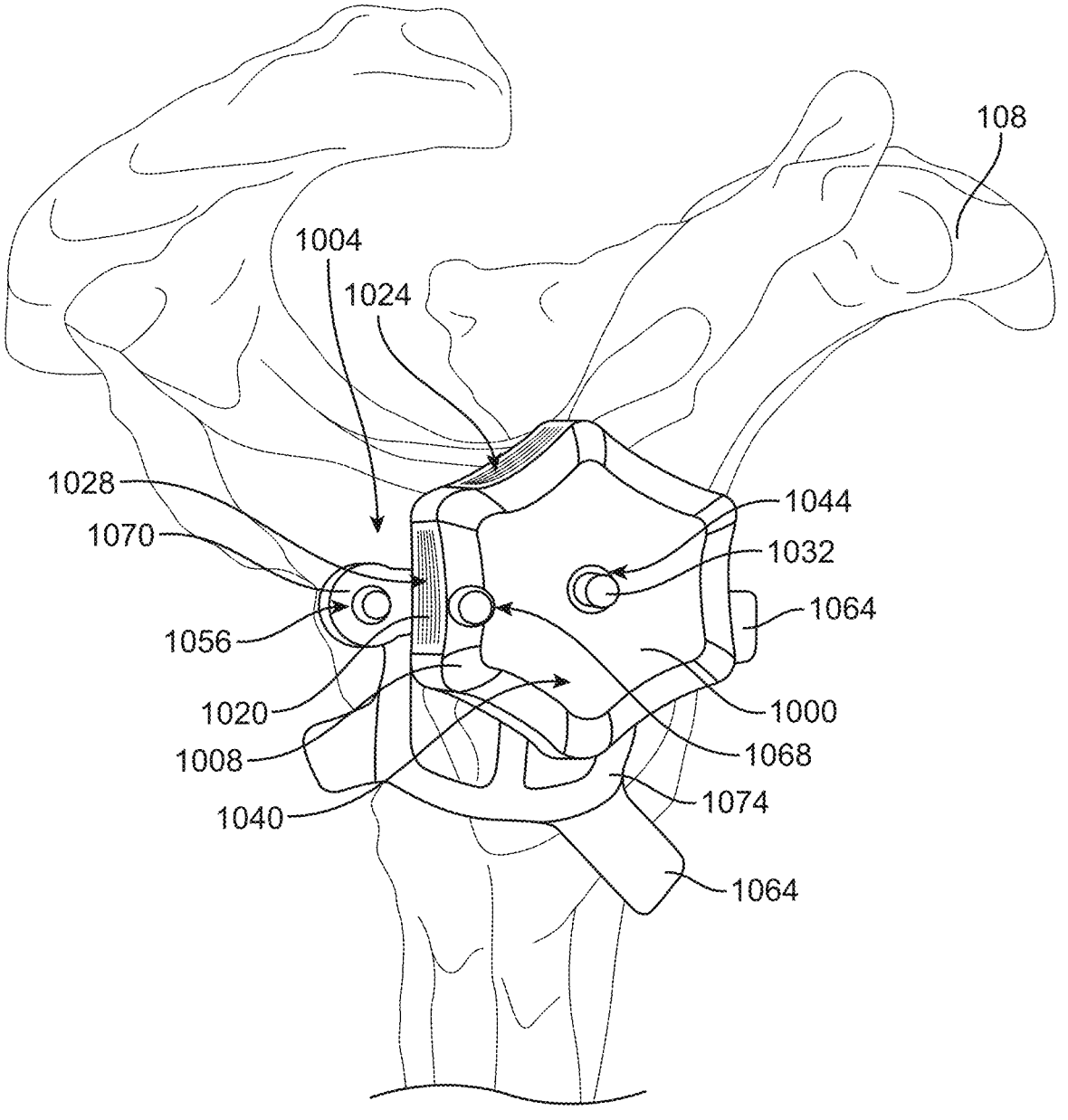
FIG. 4 is a back view of an exemplary pin guide interacting with patient anatomy, according to at least one embodiment.
Figure 5:
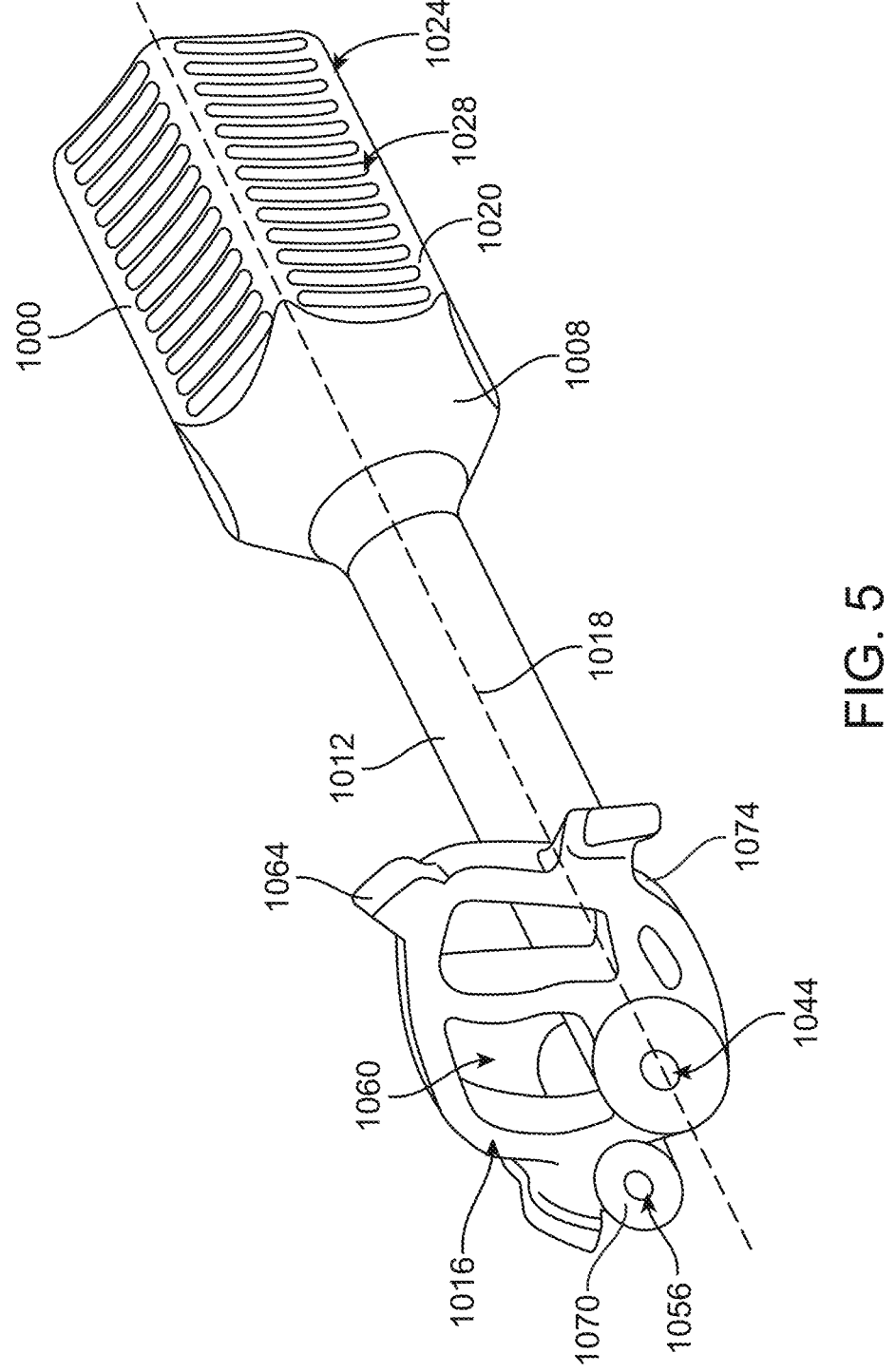
FIG. 5 is a perspective view of an exemplary pin guide, according to at least one embodiment.
Figure 6:
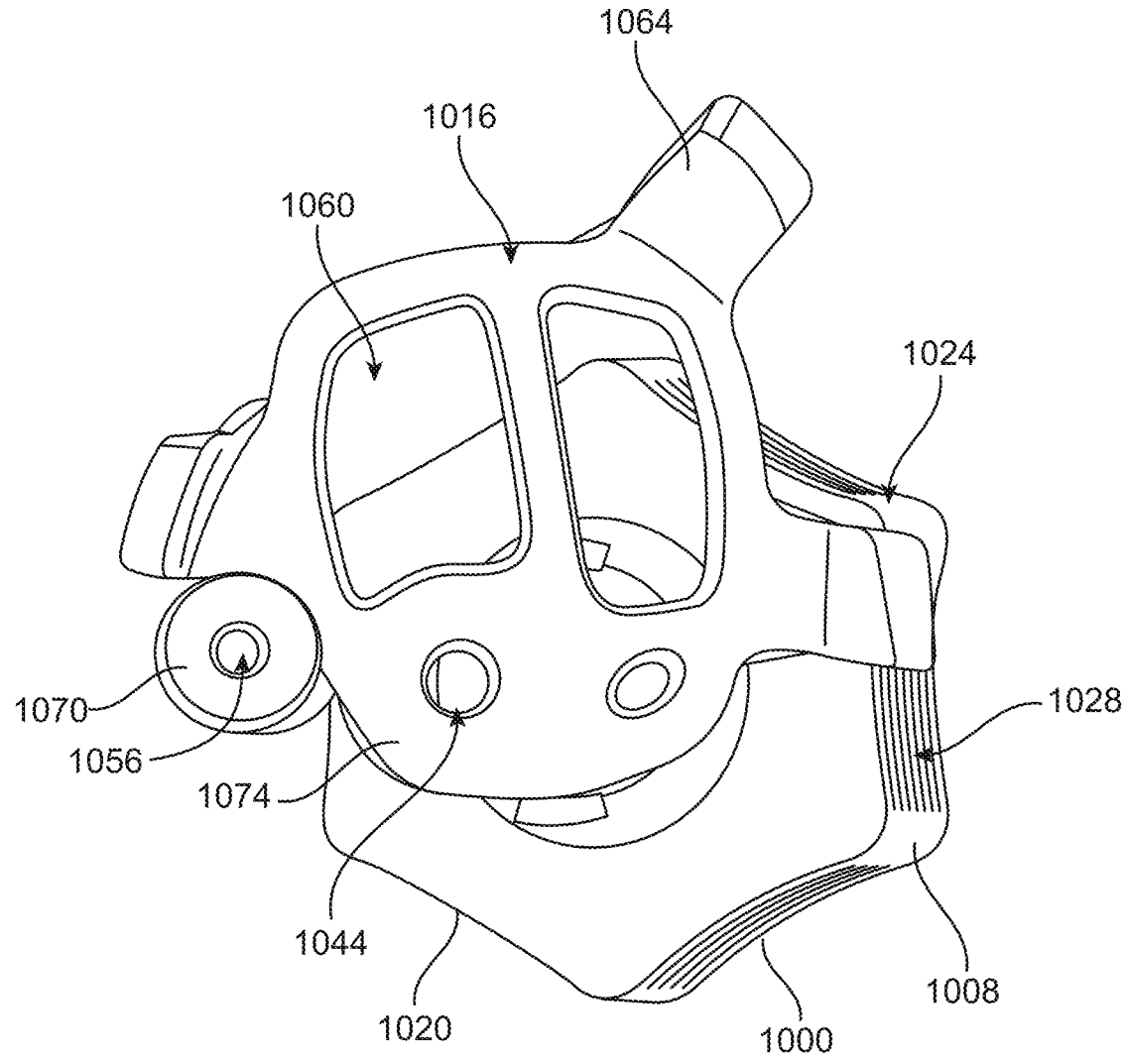
FIG. 6 is a front view of an exemplary pin guide, according to at least one embodiment.
Figure 7:
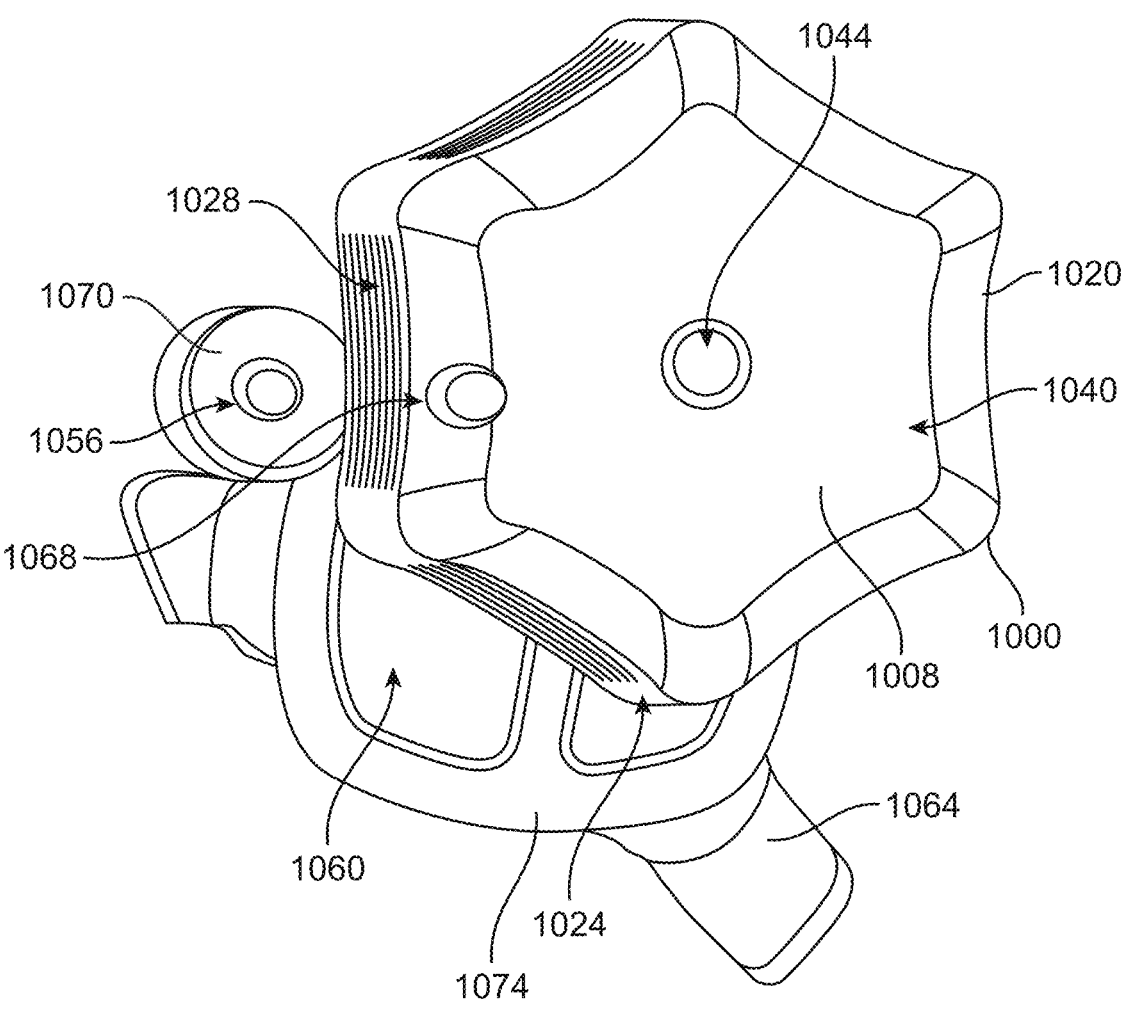
FIG. 7 is a back view of an exemplary pin guide, according to at least one embodiment.

As discussed above, an exemplary RSA system may include one or more instruments to aid in the installation of the implant assembly 100. These instruments may be included in a kit (sterile, non-sterile, or a combination of separately packaged sterile and non-sterile components) containing the implant assembly components such that the surgeon may easily access all items needed to perform the procedure. For example, a pin guide and guide pins may be utilized to assist with the precise placement of the baseplate, as shown in FIGS. 3 and 4. The pin guide 1000 may include a patient-specific face 1016 designed to interact with the contours of a bony surface 1004.

In various embodiments, the pin guide 1000 includes a patient-specific face 1016 and may be configured to allow for accurate placement of a central pin 1032 and a second pin (see FIG. 10) through the bony surface 1004 of the scapula 108. In at least one embodiment, the pin guide 1000 defines a longitudinal/central pin guide axis, otherwise referred to as a "central axis" 1018. In one embodiment, the second pin is an anti-rotation pin 1036 for remaining in place during portions of a surgery to prevent movement or rotation of other components. In another embodiment, the second pin may also be removed and rotated during surgery. In at least one embodiment, the central pin 1032 and the anti-rotation pin 1036 guide the later placement of a baseplate trial and/or baseplate upon the bony surface 1004, as well as the drilling location for the post of the baseplate. In another embodiment, the central pin 1032 and/or the anti-rotation pin 1036 (e.g., via spikes or broaches) are instead affixed to the bottom of the patient-specific face 1016 and provide reference points on the bony surface 1004 by creating orifices in the tissue of the bony surface 1004.

As will be understood, one of ordinary skill in the art may use or calculate certain anatomical references for use in RSA (or other) surgeries. There may exist specific design envelopes, such as those for regulatory purposes, that require precise angulations and calculations. In certain embodiments, the systems, devices, and processes discussed herein may leverage such anatomical references for regulatory-cleared systems, devices, and processes, which may be different from systems, devices, and processes that are fully custom and may not have the same design envelope regulatory requirements. Such references used in various embodiments herein include a Friedman's Line 1019, defined as a line extending from the center of the glenoid cavity 104 to a medial end (not shown) of the scapula 108, and a sagittal plane 1048 defined orthogonal to the Friedman's Line 1019. One of ordinary skill in the art would understand that other anatomical references may be appropriate to calculate, determine, and/or meet various design envelopes, including, but not limited to, Maurer Lines, calculations related to anatomical planes (e.g., sagittal plane), etc. In at least one embodiment, certain design features of devices discussed herein may be predetermined based on a patient's anatomy (e.g., via received CT scans or the like) and then included in a corresponding device. As will further be understood, different features of a device may be based upon or predetermined based on different anatomical features (e.g., a post angle may be based on Friedman's Line, but an angle of a baseplate body may be based on the patient's scapula or a sagittal plane).

As will be understood from discussions herein, the central axis 1018 of the handle 1008 of the pin guide 1000, a central post (e.g., post 152), or other components discussed herein may not be parallel to the Friedman's Line 1019 and may not be perpendicular to the sagittal plane 1048. As will be understood, components herein may be at any angle with respect to Friedman's line 1019 or the sagittal plane 1048 in any plane (e.g., in x, y, or z directions). For example, components discussed herein (e.g., post 152, central axis 1018 of the handle 1008) may be 0, 1, 2, 3, 4, 5, 6, 7, 8, 9, 10, 10-20, or 21-90 degrees from the Friedman's Line 1019 (e.g. where parallel to the Friedman's Line would be 0 degrees). Thus, the patient-specific face 1016 of the pin guide 1000, the baseplate trial, and the baseplate may mate with the bony surface askew to the sagittal plane 1048, such as in patient-specific procedures with an off-axis baseplate and post installation.

Placement of the pin guide 1000 may additionally help to prepare the bony surface 1004 of the patient for installation of the implant assembly 100. After placement of the patient-specific face 1016 of the pin guide 1000 on the bony surface 1004, the surgeon may continue to modify the bony surface 1004 until a desired fit between the bony surface 1004 and the patient-specific face 1016 is achieved. In one embodiment, this process is performed iteratively prior to installation of the pins 1032, 1036.

The pin guide 1000 may include an angle 1052 between the patient-specific face 1016 and the central axis 1018. In one embodiment, the angle 1052 may be between 0 and 360 degrees, or between 0 and 270 degrees, or between 0 and 180 degrees, or between 0 and 90 degrees, or between 10 and 80 degrees, or between 15 and 70 degrees, or between 20 and 60 degrees, or between 25 and 50 degrees, or between 30 and 45 degrees. In an embodiment where the angle 1052 is not equivalent to 90 degrees, the patient-specific face 1016 is askew with the sagittal plane 1048. As discussed herein, the orientation of the patent-specific face may be angled in any direction (e.g., x, y, or z directions) and may not be parallel to the Friedman's Line or orthogonal the sagittal plane.

In the embodiment shown, the pin guide 1000 includes the handle 1008, a cylindrical shaft 1012, and the patient-specific face 1016. In various embodiments, the pin guide 1000 may further comprise a top surface 1040 containing an aperture 1044 that extends axially through the handle 1008 and the shaft 1012. A width of the aperture 1044 may be substantially similar to or slightly greater than a diameter of the central pin 1032, which may be placed within the aperture 1044 during installation to facilitate proper fixation of the central pin 1032 within the bony surface 1004. A central axis of the shaft 1012 is thus colinear to the central axis 1018 of the central pin 1032 when the pin guide 1000 is in use.

In some embodiments, the shaft 1012 further comprises orientation markers (not depicted) that may assist with the orientation of the pin guide 1000. For example, in one embodiment, the shaft 1012 may have the orientation markers "SUP" and "INF" where "SUP" indicates the superior portion of the shaft 1012 and "INF" indicates the inferior portion of the shaft 1012. The superior portion of the shaft 1012 may be aligned with the upper portion of the bony surface 1004, towards the top of shoulder. The inferior portion of the shaft 1012 may be aligned with the lower portion of the bony surface 1004, towards the bottom of the shoulder. In some embodiments, other orientation markers may be used, such as arrows, symbols, words, other acronyms, or other combinations thereof.

The handle 1008 of the pin guide 1000 may comprise one or more edges 1020. Although typically rectangles, the edges 1020 may be, according to an embodiment, of any shape, including but not limited to ellipses, triangles, trapezoids, parallelograms, etc. The edges 1020 may be comprised of surfaces 1024 that may feature ridges 1028 to enhance the grip of the surgeon using the pin guide 1000 during surgery. The handle 1008 may contain additional features or attachments not discussed herein to improve the ergonomic nature of the handle 1008 or provide for greater comfort during use.

In one embodiment, the handle 1008 may comprise between three and twelve edges 1020, or between four and ten edges 1020, or between five and eight edges 1020, or six or seven edges 1020, depending upon the preference of the user. The edges 1020 may be uniform in size or incongruent/asymmetric. A diameter and a length of the handle 1008 may additionally be customized to promote greater grip strength and ease of use. In one embodiment, the diameter of the handle 1008 may be greater than the diameter of the shaft 1012.

The patient-specific face 1016 may comprise an aperture 1056 configured to accept and guide the placement of the anti-rotation pin 1036. As such, the diameter of the aperture 1056 may be substantially similar to or slightly greater than a diameter of the anti-rotation pin 1036. In one embodiment, the anti-rotation pin 1036 is installed substantially parallel to the central pin 1032. In alternate embodiments, the anti-rotation pin 1036 and the central pin 1032 are not parallel but are off angle from each other. The handle 1008 of the pin guide 1000 may also include an aperture 1068 designed for the anti-rotation pin 1036. The apertures 1056, 1068 may be colinear and have substantially equivalent diameters.

In various embodiments, the pin guide 1000 includes an anti-rotation pin guide structure 1070 for guiding the anti-rotation pin 1036, which defines the aperture 1056. In the embodiment shown in FIG. 3, the anti-rotation pin guide structure 1070 is generally cylindrical and extends away from the patient-specific face 1016, although the anti-rotation pin guide structure 1070 may be any suitable shape. In some embodiments, the anti-rotation pin guide structure 1070 extends away from the patient-specific face 1016 between 1-50 millimeters. In particular embodiments, the anti-rotation pin guide structure 1070 extends away from the patient-specific face to or past the handle 1008 and, in some embodiments, may be attached, coupled to, or integrally formed with, the handle 1008.

For example, in one embodiment, the central pin 1032 and/or aperture 1056 may have a diameter between 0.5 mm and 5.0 mm, or between 0.7 mm and 4.0 mm, or between 1.0 mm and 3.2 mm, or between 1.6 mm and 3.0 mm, or between 2.0 mm and 2.5 mm, or any other suitable diameter in accordance with the principles of this disclosure. Similarly, in one embodiment, the anti-rotation pin 1036 and/or aperture 1068 may have a diameter between 0.5 mm and 5.0 mm, or between 0.7 mm and 4.0 mm, or between 1.0 mm and 3.2 mm, or between 1.6 mm and 3.0 mm, or between 2.0 mm and 2.5 mm, or any other suitable diameter in accordance with the principles of this disclosure.

In one embodiment, the patient-specific face 1016 may further comprise one or more windows 1060 and tabs 1064 protruding downward and away from the patient-specific face 1016 that aid in visualizing and stabilizing the pin guide 1000 on the scapula 108 while the pins 1032, 1036 are installed. The windows 1060, in the form of apertures, may allow for a reduction in the amount of material used to construct the patient-specific face 1016. The locations, quantity, and size of the windows 1060 and tabs 1064 may be customized in conjunction with the patient-specific face 1016 depending upon where visualization of underlying tissue may be most helpful. In one embodiment, at least three tabs 1064 are present to contact at least two ends of the scapula 108.

The tabs 1064 may be of any suitable size or shape. For example, as shown, the tabs 1064 are generally curved with a generally rectangular end. In various embodiments, the tabs 1064 may cover or include more or less of the perimeter of the pin guide body 1074 than shown (e.g., the area of two tabs 1064 shown herein may be covered by one, larger tab). In at least one embodiment, at least one of the tabs 1064 has a rounded or triangular shaped end.

The top surface 1040 of the pin guide 1000 may feature one or more bevels as displayed in the present embodiment or any number of additional designs, features, and attachments to facilitate use of the handle 1008. In accordance with the number of edges 1020 present, the top surface 1040 may take the form of any shape, including but not limited to a triangle, square, trapezoid, parallelogram, pentagon, hexagon, heptagon, octagon, nonagon, etc. In one embodiment, the top surface 1040 may take the form of a circle or ellipse, in which case the edges 1020 may instead form one smooth surface 1024 in the shape of a right or oblique cylinder without corners.

Views of the patient-specific face 1016 of the pin guide 1000 are displayed in FIGS. 4-7. The patient-specific face 1016 is designed to mate or otherwise interface with the bony surface 1004 of the scapula 108, which may be deformed or modified in preparation for surgery. For example, raised portions of the bony surface may be mapped onto the patient-specific face 1016 as recessions such that the raised portions may easily be "inserted" into the recessions on the patient-specific face 1016, and vice versa. The patient-specific face 1016 can in one embodiment be considered a "negative" of the bony surface 1004 such that the two surfaces are compatible.

In various embodiments, the patient-specific face 1016 may be similar or consistent with a size or diameter of the bony surface 1004. The patient-specific face 1016 may take the form of any shape and as such may have varying diameters. In one embodiment, for example, the longest diameter of the patient-specific face 1016 is between approximately 30 mm and 50 mm, or between approximately 36 and 44 mm, or between approximately 38 mm and 42 mm, or any other suitable diameter in accordance with the principles of this disclosure.

The windows 1060 may allow surgeons to examine tissue during installation of the pins. As displayed in FIG. 6, the one or more windows 1060 need not be identical in shape, size, nor angular orientation with respect to the bony surface 1004. Physical characteristics of the one or more windows 1060 may be based on areas of the bony surface 1004 that, for example, need to be examined during surgery or would not be compatible with contacting the patient-specific face 1016. The inclusion of windows 1060 may impact the cost to produce the pin guide 1000, as the windows 1060 may allow for a reduced amount of material to be used in manufacturing of the pin guide 1000.

Figure 8:
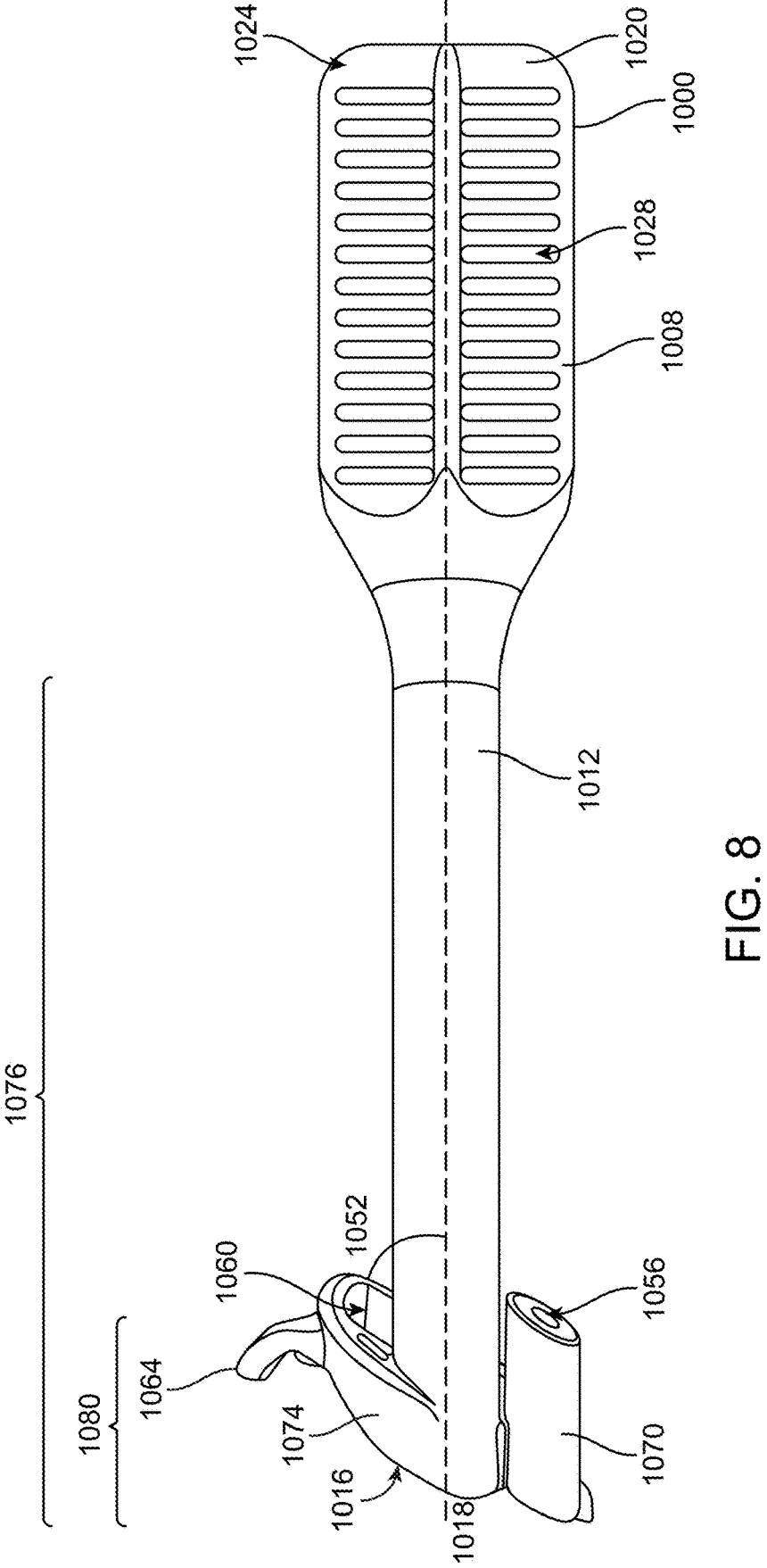
FIG. 8 is a first side view of an exemplary pin guide, according to at least one embodiment.
Figure 9:
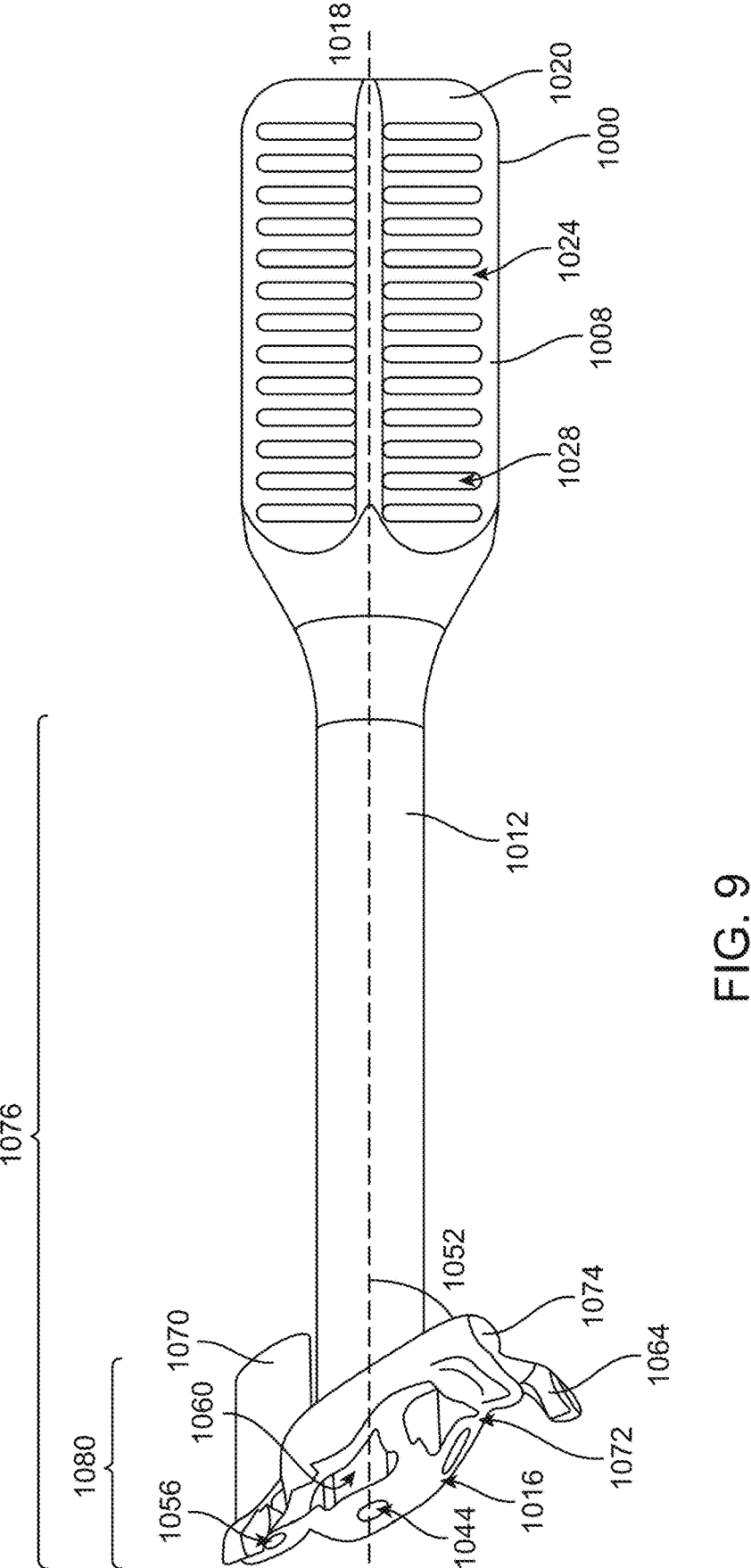
FIG. 9 is a second side view of an exemplary pin guide, according to at least one embodiment.

Referring now to the exemplary embodiment shown in FIGS. 8 and 9, the angle 1052 between the inclination of the patient-specific face 1016 and the central axis 1018 is acute. As will be understood from discussions herein, the angle 1052 may be any suitable angle, including, but not limited to, 1-15 degrees, 16-25 degrees, 25-90 degrees, 90-180 degrees, etc.

In certain embodiments, the pin guide 1000 includes a length 1076, which includes a length of the shaft 1012 and a length 1080 of the pin guide body 1074. In one embodiment, the length 1076 represents the total distance of entry into patient anatomy, wherein the handle 1008 remains external to incision. The length 1080 of the pin guide body 1074 may be impacted by the angle 1052 of inclination of the patient-specific face 1016 with respect to the central axis 1018 and by a thickness of the pin guide body 1074. The thickness of the pin guide body 1074 may in one embodiment be substantially similar to a thickness of the later-installed baseplate trial and/or the baseplate.

Figure 10:
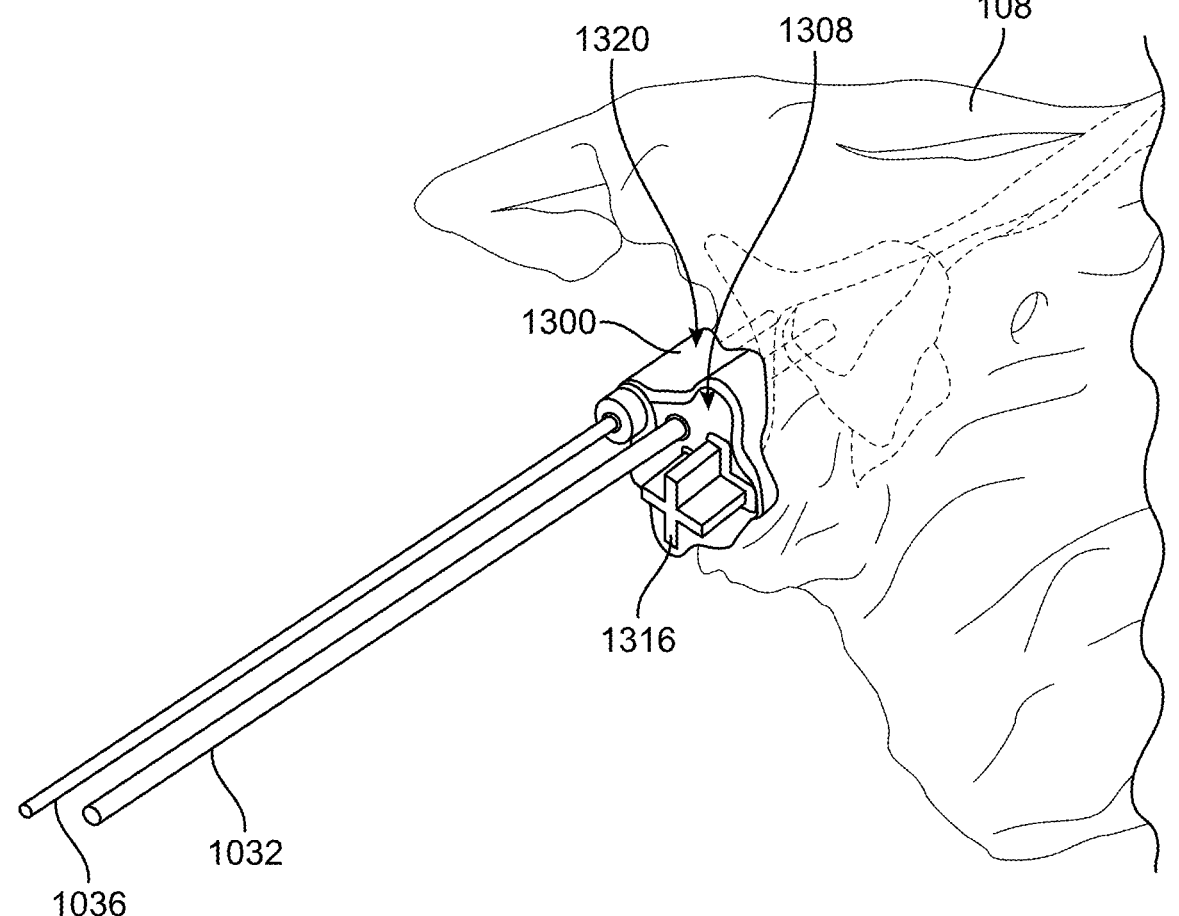
FIG. 10 is a perspective view of an exemplary baseplate trial interacting with patient anatomy, according to at least one embodiment.
Figure 11:
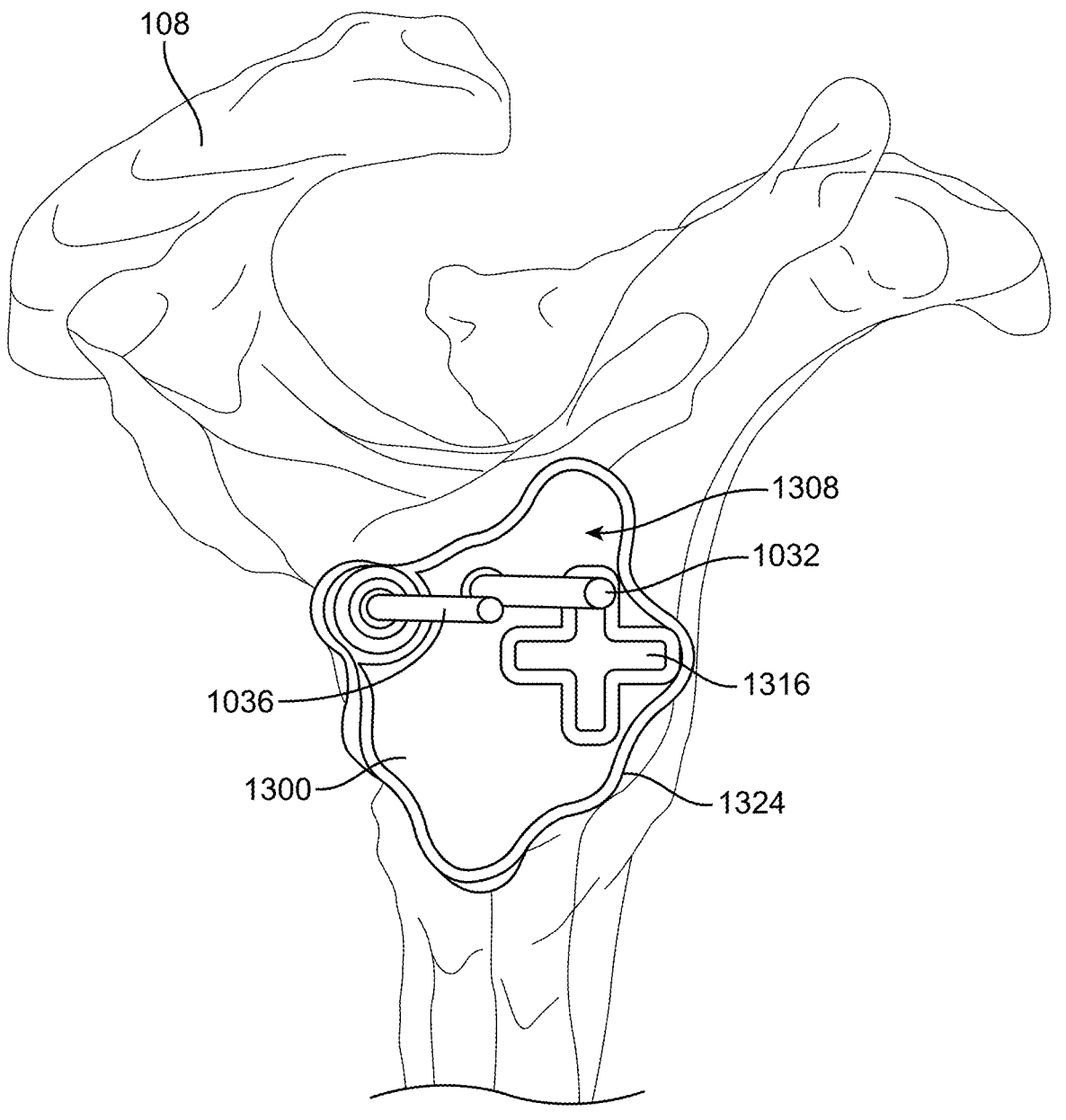
FIG. 11 is a front view of an exemplary baseplate trial interacting with patient anatomy, according to at least one embodiment.

Referring now to FIGS. 10 and 11, the pins 1032, 1036 are rigid in at least one embodiment and installed in the bony surface 1004 such that a baseplate trial 1300 may subsequently be placed by the surgeon using the pins 1032, 1036 as references. The baseplate trial 1300 may be directed by the pins 1032, 1036 through a central aperture 1304 and a raised aperture 1306, respectively, in the baseplate trial 1300 to ensure a proper fit of the baseplate trial 1300 on the bony surface 1004.

Figure 12:
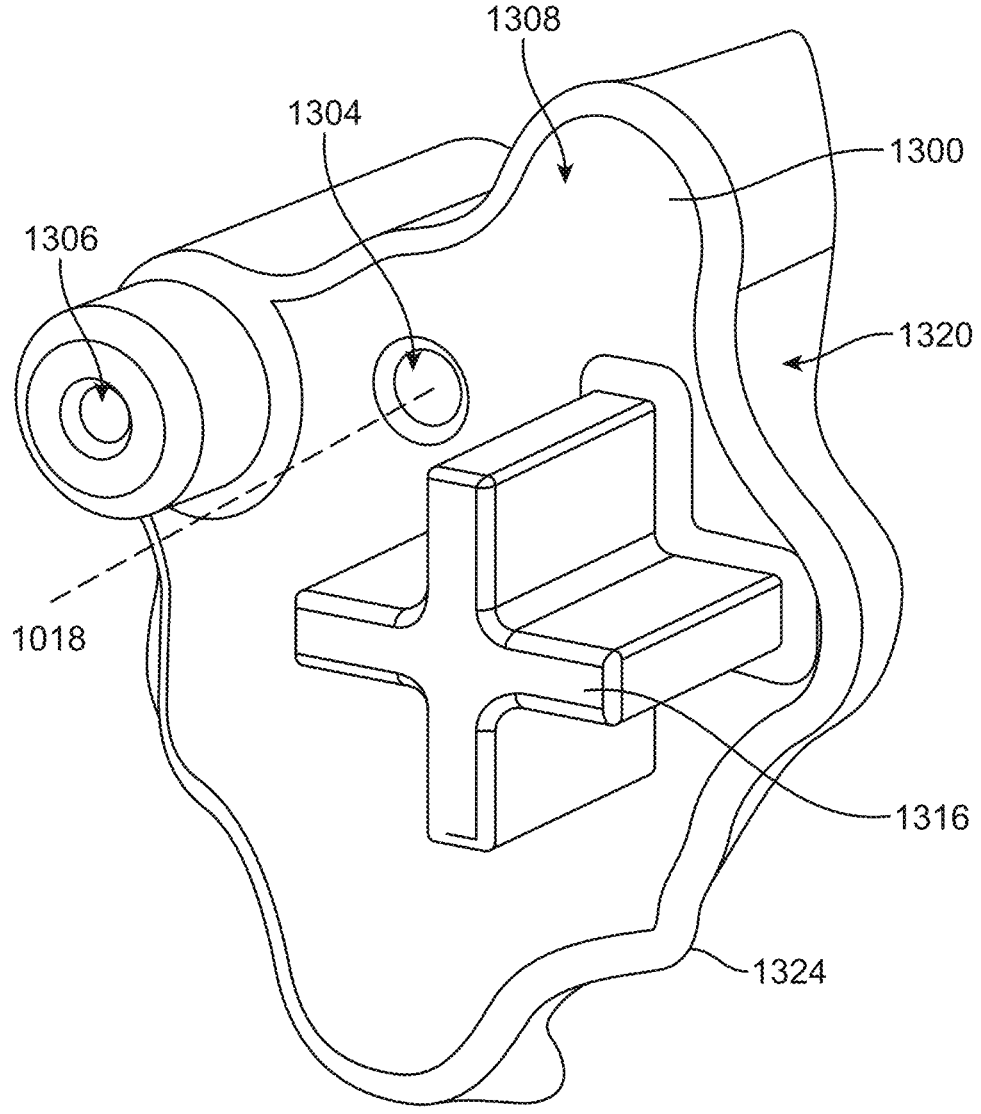
FIG. 12 is a perspective view of an exemplary baseplate trial, according to at least one embodiment.
Figure 13:
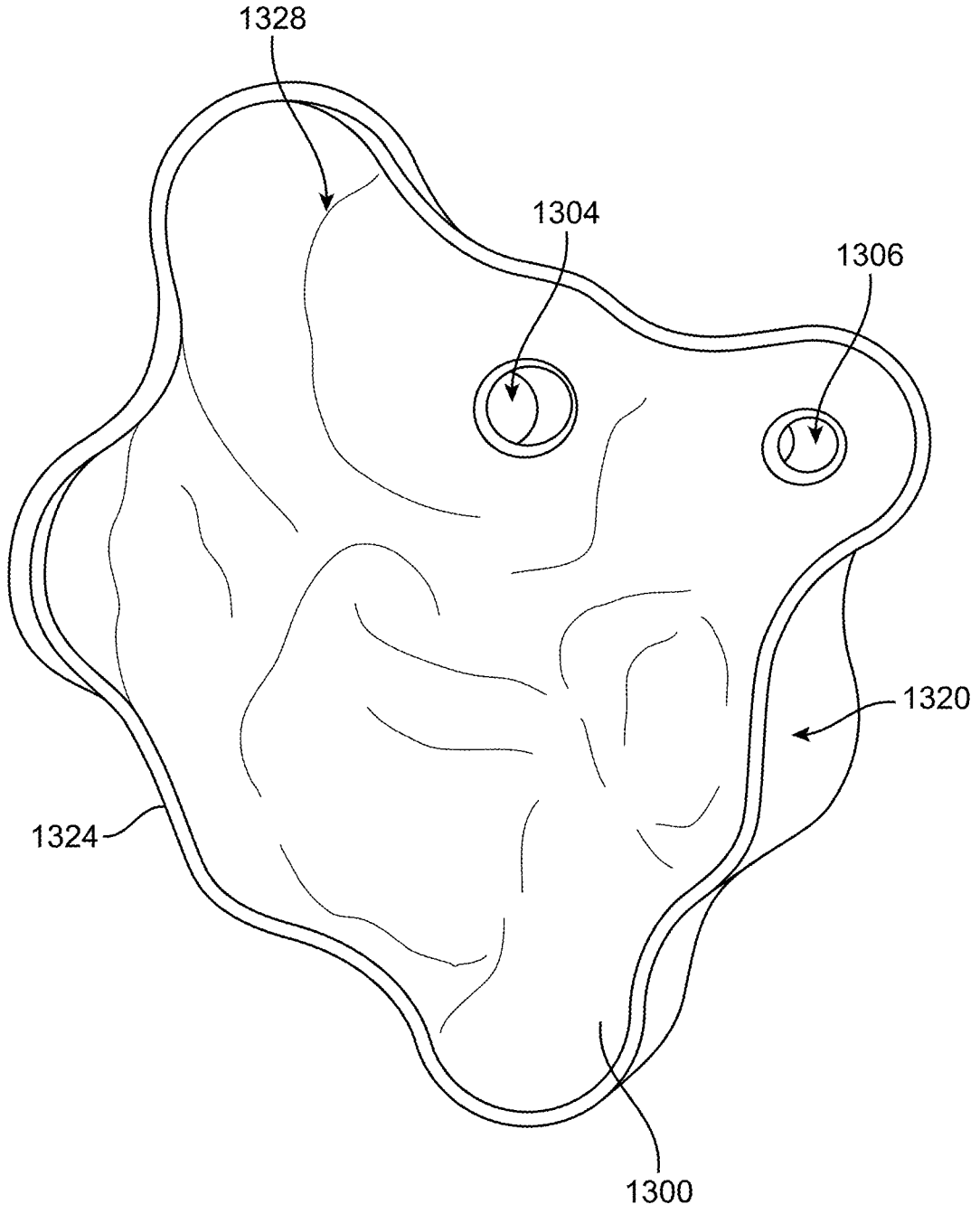
FIG. 13 is a back view of an exemplary baseplate trial, according to at least one embodiment.

The raised aperture 1306 may comprise a solid boss, as shown in FIG. 12. The raised aperture 1306 may comprise an outer edge which may extend from the surface of the baseplate trial 1300 that does not abut the bony surface 1004. In at least one embodiment, the outer edge of the raised aperture slopes or angles towards an upper surface of the raised aperture 1306. The upper surface may be flat or angled downward, towards the opening of the raised aperture 1306. The exemplary embodiment of the raised aperture 1306 depicted in FIG. 12 comprises an additional angled face between the upper surface and the interior of the raised aperture 1306. Some embodiments may omit the additional angled face. The structure of the raised aperture 1306 may further stabilize the anti-rotation pin 1032 when the baseplate trial 1300 is placed.

At this stage, the surgeon may assess the fixture of the baseplate trial 1300 upon the bony surface 1004 as a reflection of the fit of the later-installed baseplate. For example, the surgeon may decide to alter bony structure of the patient in response to an unexpected incompatibility between the baseplate trial 1300 and the bony surface 1004 or may further alter the patient anatomy to better fit the baseplate. In addition to apertures 1304, 1306 for the pins 1032, 1036, the baseplate trial 1300 may include a flat front surface, or front surface 1308, a projection 1316, and side surface 1320. As shown in FIG. 12, the projection 1316 may be raised and extend away from the front surface 1308. Although depicted as a cross in one embodiment, the projection 1316 may take the form of any shape or marker, including but not limited to a square, circle, rectangle, annulus, triangle, arrow, hemisphere, etc. The projection 1316 may provide a visual marker to the surgeon during implantation or offer a handle with which to grip the baseplate trial 1300 during surgery. In one embodiment, the projection 1316 may act as a button or may allow for depression such that a height of the projection 1316 with respect to the front surface 1308 of the baseplate trial 1300 is adjustable.

The side surface 1320 of the baseplate trial 1300 may in one embodiment be smooth and without sharp edges. In another embodiment, the side surface 1320 may feature edges or contours in accordance with the shape of an outer perimeter 1324 of the front surface 1308 of the baseplate trial 1300. While the outer perimeter 1324 may take the form of a known shape such as a circle or ellipse in one embodiment, the outer perimeter 1324 of the baseplate trial 1300 may take the form of a freeform shape, customized for each patient. The outer perimeter 1324 may in one embodiment be substantially similar to an outer perimeter of the pin guide body 1074 of the pin guide 1000. In another embodiment, the outer perimeter 1324 may appear different from the perimeter of the patient-specific face 1016 of the pin guide 1000. The shape of the outer perimeter 1324 as well as a patient-specific surface 1328 may mimic the texture, size, shape, and boundary of the bony surface 1004 of the patient (see FIG. 13). The patient-specific surface 1328 of the baseplate trial 1300 may include at least one common feature with the patient-specific face 1016 of the pin guide 1000. In one embodiment, the patient-specific surface 1328 of the baseplate trial 1300 and the patient-specific face 1016 of the pin guide 1000 may be substantially similar (e.g., may have same general shape, may have similar slopes, may have similar dimensions, etc.).

Figure 14:
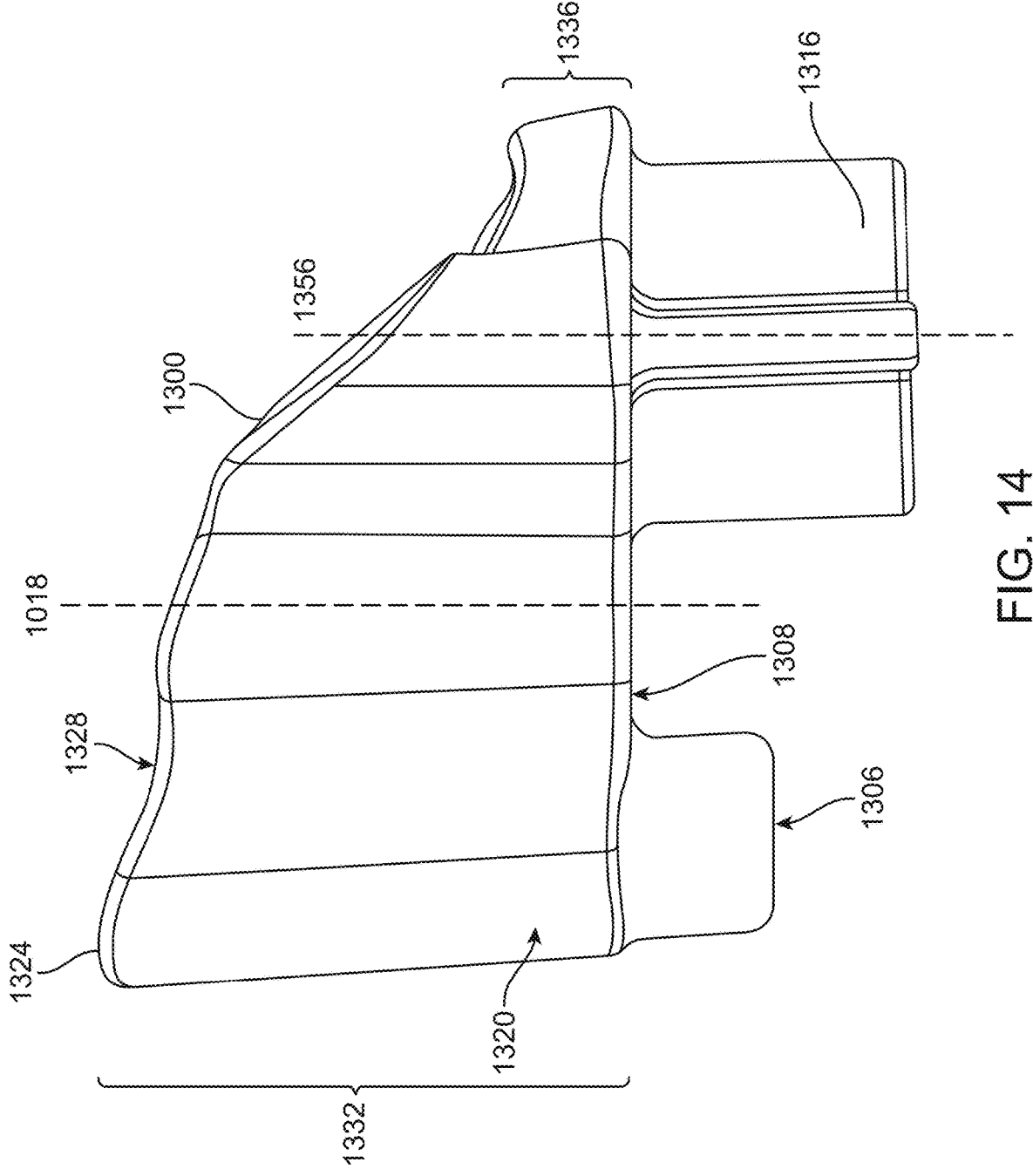
FIG. 14 is a first side view of an exemplary baseplate trial, according to at least one embodiment.
Figure 15:
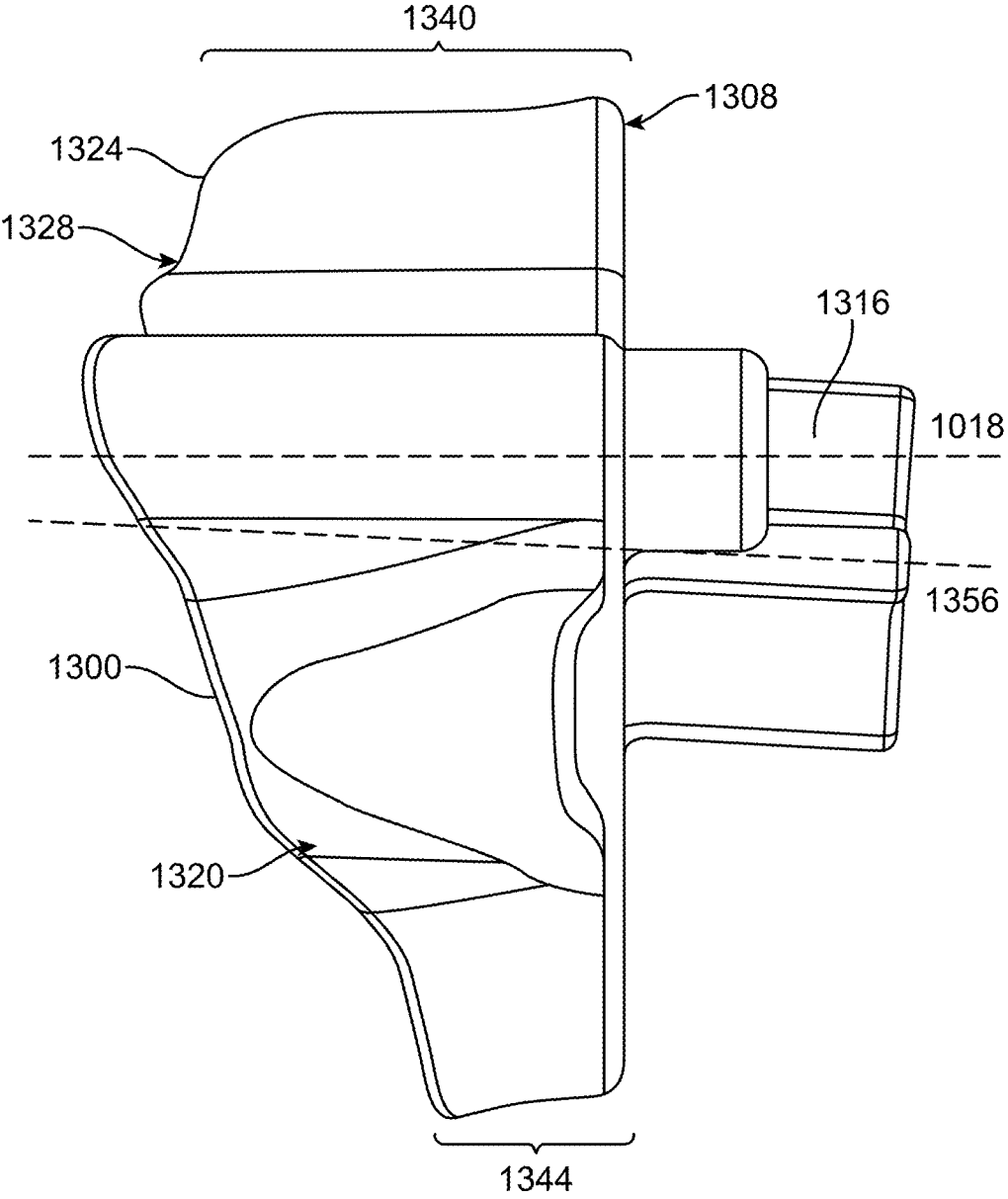
FIG. 15 is a second side view of an exemplary baseplate trial, according to at least one embodiment.
Figure 16:
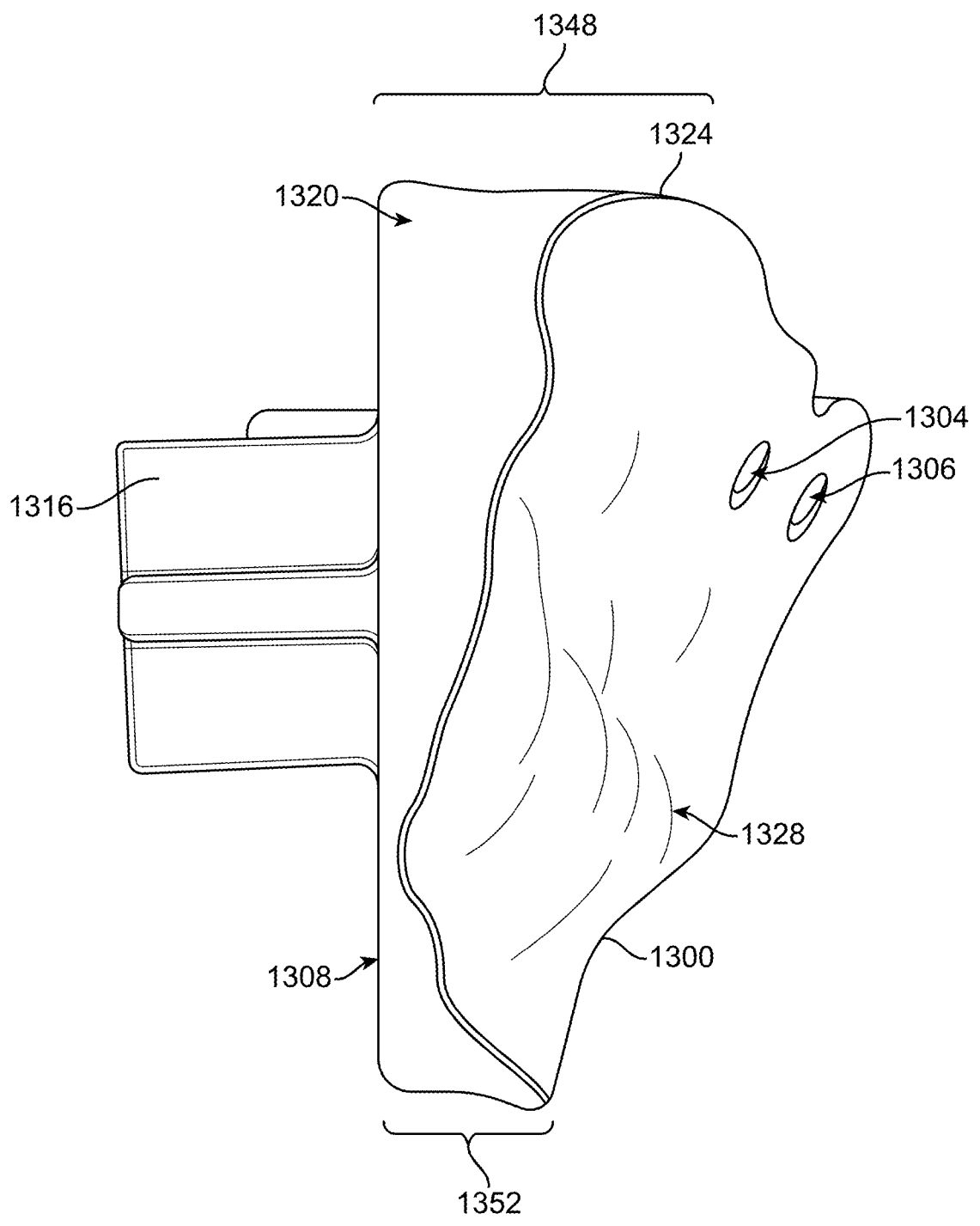
FIG. 16 is a third side view of an exemplary baseplate trial, according to at least one embodiment.

FIGS. 14-16 display the baseplate trial 1300 from various side views. As shown, augment thicknesses 1332, 1336, 1340, 1344, 1348, and 1352 of the baseplate trial 1300 may vary significantly as a result of a "slope" of the outer perimeter 1324. The slope of the patient-specific surface 1328 of the baseplate trial 1300 may not be constant in one embodiment and may feature peaks, troughs, and numerous inflection points according to the contours of the bony surface 1004.

Figure 17:
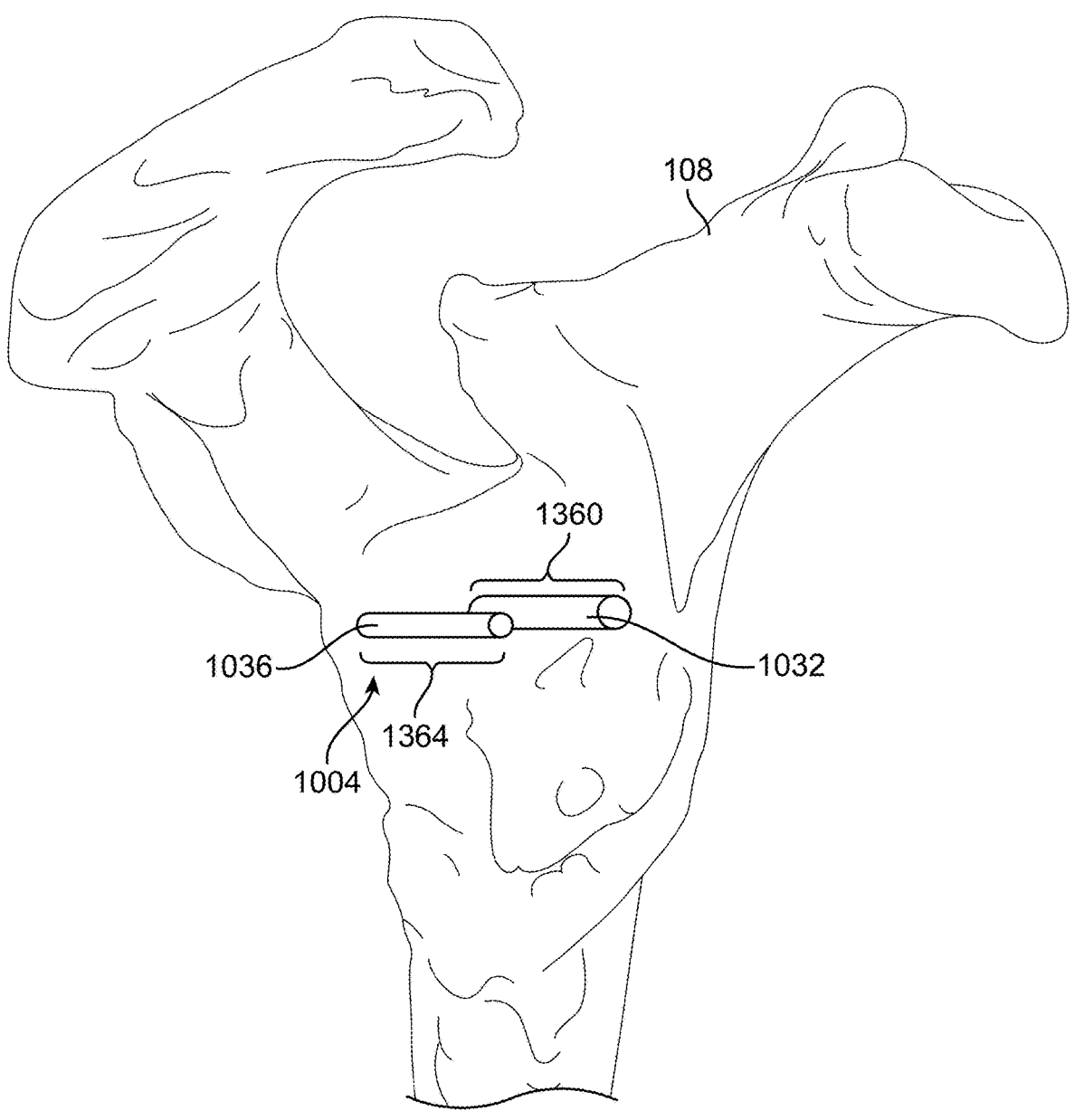
FIG. 17 is a perspective view of an exemplary central pin and an exemplary anti-rotation pin interacting with patient anatomy, according to at least one embodiment.
Figure 18:
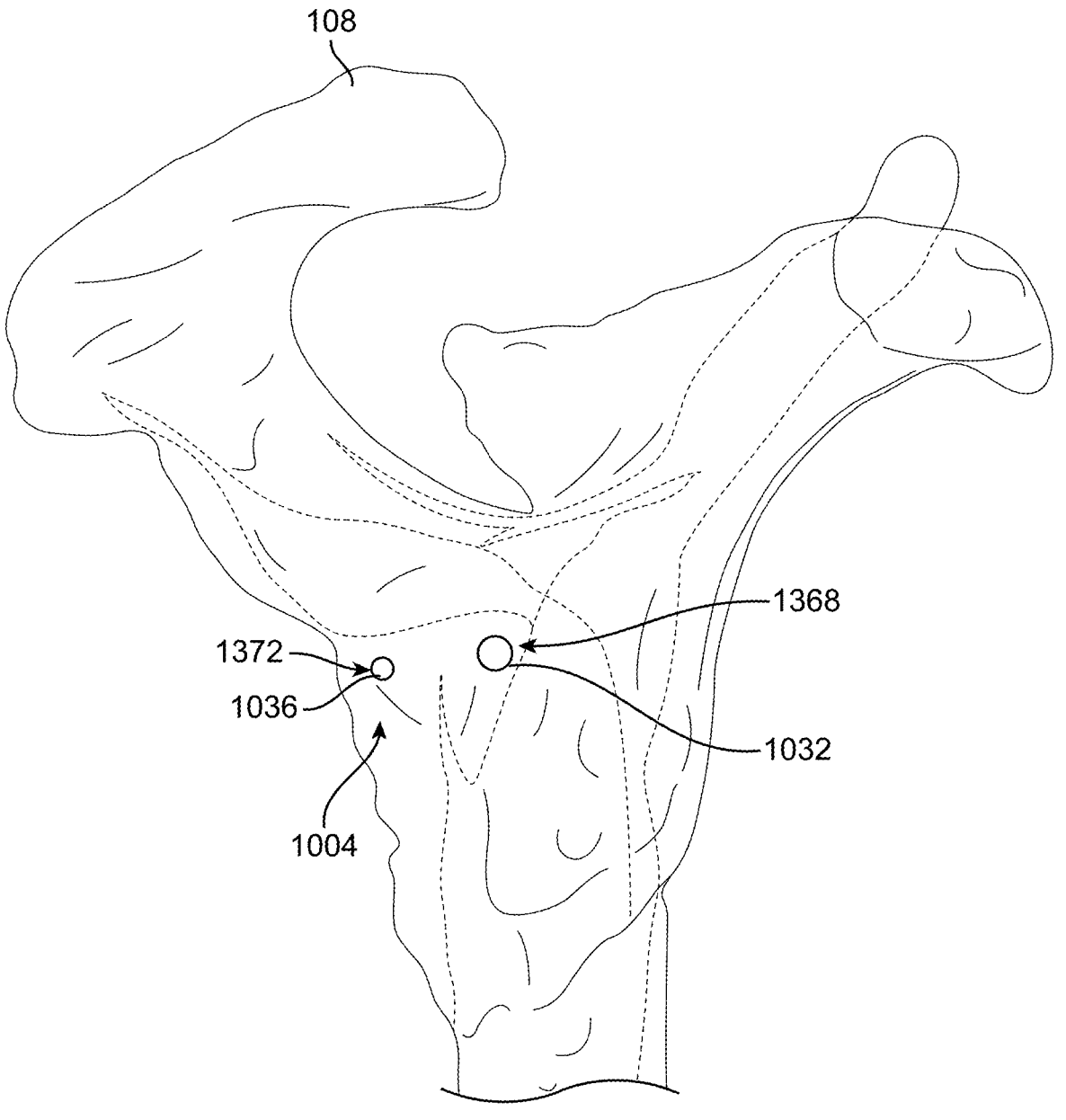
FIG. 18 is a front view of an exemplary central pin and an exemplary anti-rotation pin interacting with patient anatomy, according to at least one embodiment.

The baseplate trial 1300 may subsequently be removed from the bony surface 1004 and leave behind the central pin 1032 and the anti-rotation pin 1036, implanted at insertion distances (or depths) 1360 and 1364 into the scapula 108, as depicted in FIGS. 17 and 18. In one embodiment, the insertion distances 1360, 1364 are nonequivalent and may be patient specific. The central pin 1032 may be inserted through the tissue of the bony surface 1004 to create an orifice 1368, and the anti-rotation pin 1036 is inserted through the tissue of the bony surface 1004 to create an orifice 1372, wherein orifices 1368, 1372 are of nonequivalent diameter according to one embodiment.

The sagittal plane 1048 (not shown) orthogonal to the Friedman's Line 1019 is not necessarily parallel to a cross-section of the orifice 1368. The central pin 1032 may thereby be tilted in any direction with respect to the bony surface 1004, reflective of the unrestricted angular orientation of a patient-specific baseplate post installed in future steps of the RSA procedure. The sagittal plane 1048 (not shown) orthogonal to the Friedman's Line 1019 is additionally not necessarily parallel to a central axis 1356 of the projection 1316. The projection 1316 may thereby be tilted in any direction with respect to the front surface 1308 of the baseplate trial 1300.

Figure 19A:
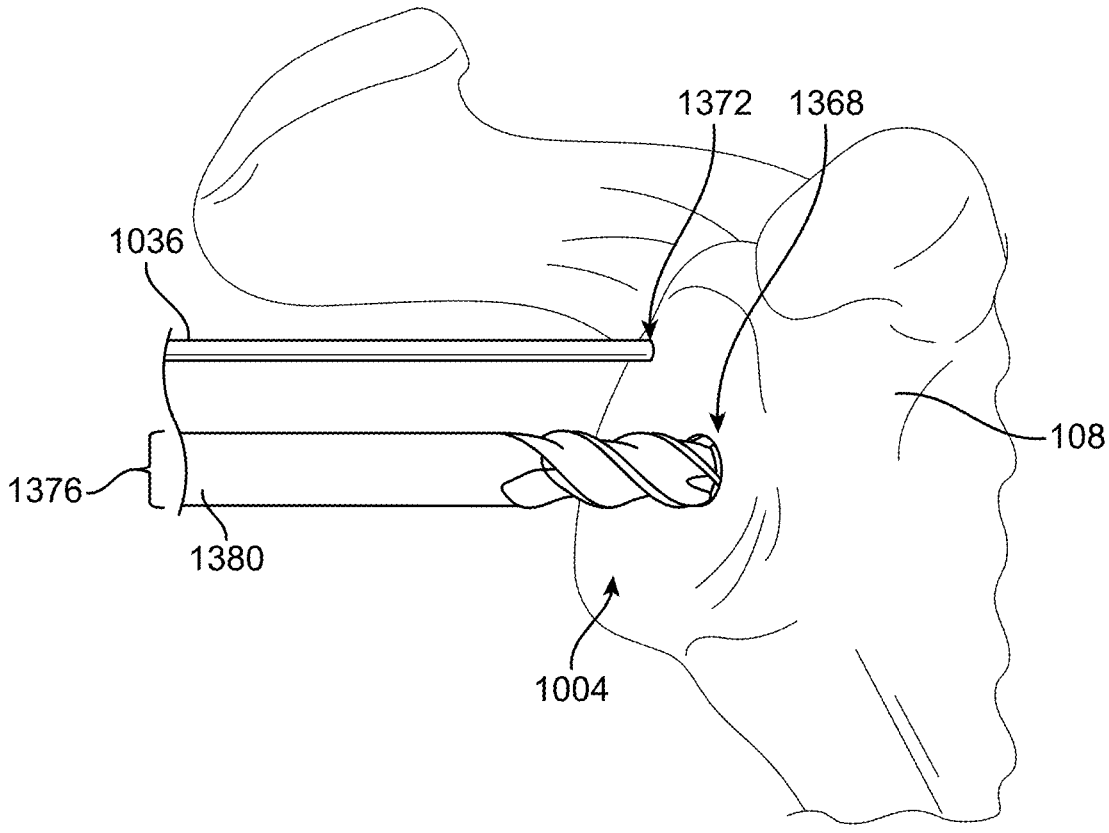
FIG. 19A is a side view of an exemplary drill and an exemplary anti-rotation pin interacting with patient anatomy, according to at least one embodiment.

Referring now to FIG. 19A, the RSA method may further comprise removal of the central pin 1032 from the implantation site such that a surgeon may drill at the site of the central pin 1032 (e.g., at orifice 1368). In various embodiments, a surgeon may use a cannulated drill to drill over the central pin 1032 instead of first removing the central pin

1032. The insertion distance 1360 of the central pin 1032 (see FIG. 17) may thus provide a reference as to the depth of drilling for installation of the baseplate post (see FIG. 20). In various embodiments, a width 1376 of a drill 1380 is in accordance with a predicted width of a post of the baseplate, as the drill 1380 bores an appropriate-sized entry point for the post into the bony surface 1004.

Figure 19B:
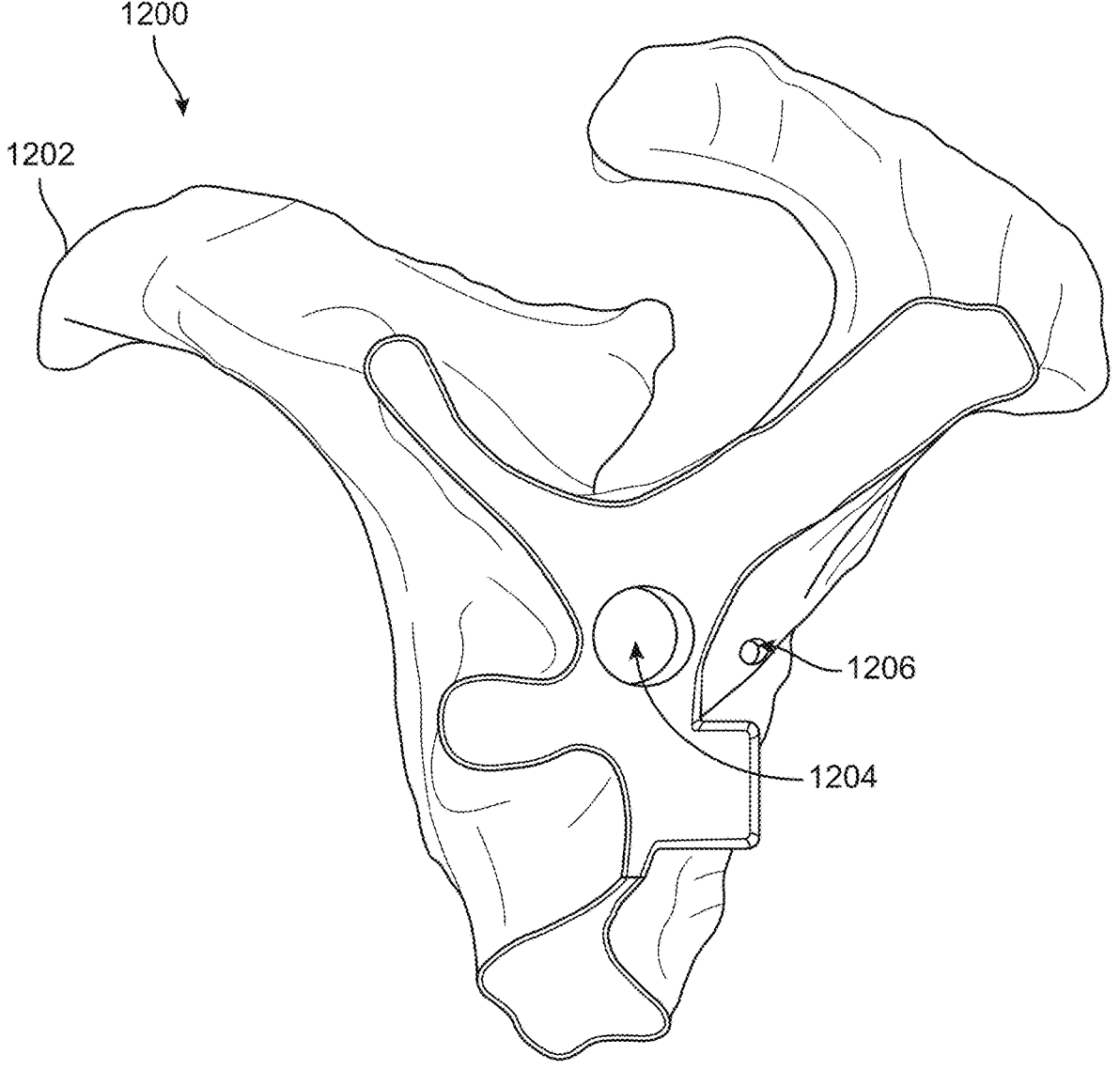
FIG. 19B is a back view of a three-dimensionally printed representation of patient anatomy, according to at least one embodiment.
Figure 19C:
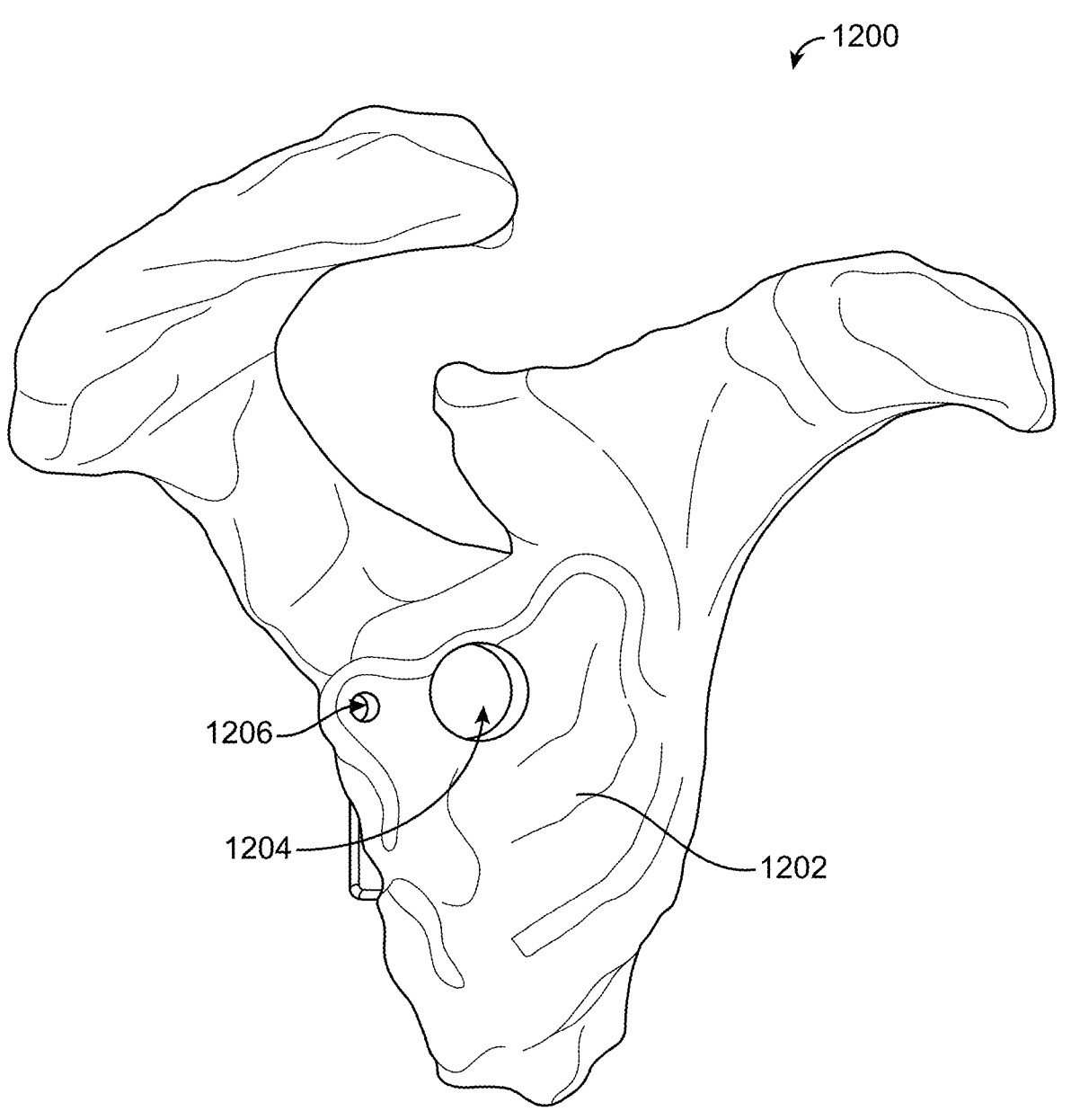
FIG. 19C is a front view of a three-dimensionally printed representation of patient anatomy, according to at least one embodiment.

The drilling step may be visualized on a three-dimensionally printed representation 1200 of patient anatomy, such as a patient-specific model, or model 1202, as shown in FIGS. 19B and 19C, which may be included with a surgical kit also including one or more other components discussed herein. Orifices 1204 and 1206 for the central pin 1032 and the anti-rotation pin 1036 respectively may be drilled into the model 1202 included during printing to simulate the surgical procedure and assess the choice of diameter, location, etc. of the orifices 1204, 1206 for the later insertion of a patient-specific baseplate post such as the exemplary post 152. The model 1202 may contain at least one or more features in common with the bony surface 1004 of the patient anatomy, as well as additional details mimicking the scapula or other anatomical features of the patient. The representation(s) 1200 may additionally be used in other steps of the RSA process, such as to simulate usage of the pin guide 1000, baseplate trial 1300, and modification of the bony surface 1004 in response to fit of the baseplate trial 1300.

In one embodiment, a central axis of the drill 1380 may be collinear with the central pin 1018. In another embodiment, the drill 1380 may enter the bony surface 1004 at a non-right angle with respect to the bony surface 1004, reflective of the unrestricted angular orientation of a patient-specific baseplate post installed in the next step of RSA procedure conveyed in FIG. 20. Herein, a cannulated screw guide, or screw guide 1400, features an internal aperture of substantially the same diameter as the anti-rotation pin 1036, and an end of the anti-rotation pin 1036 is inserted into the screw guide 1400 to aid with implanting of a patient-specific baseplate, or baseplate 1500. In various embodiments, the baseplate 1500 includes or defines an aperture (obscured) designated for entry of the anti-rotation pin 1036, which is rigid.

Figure 20:
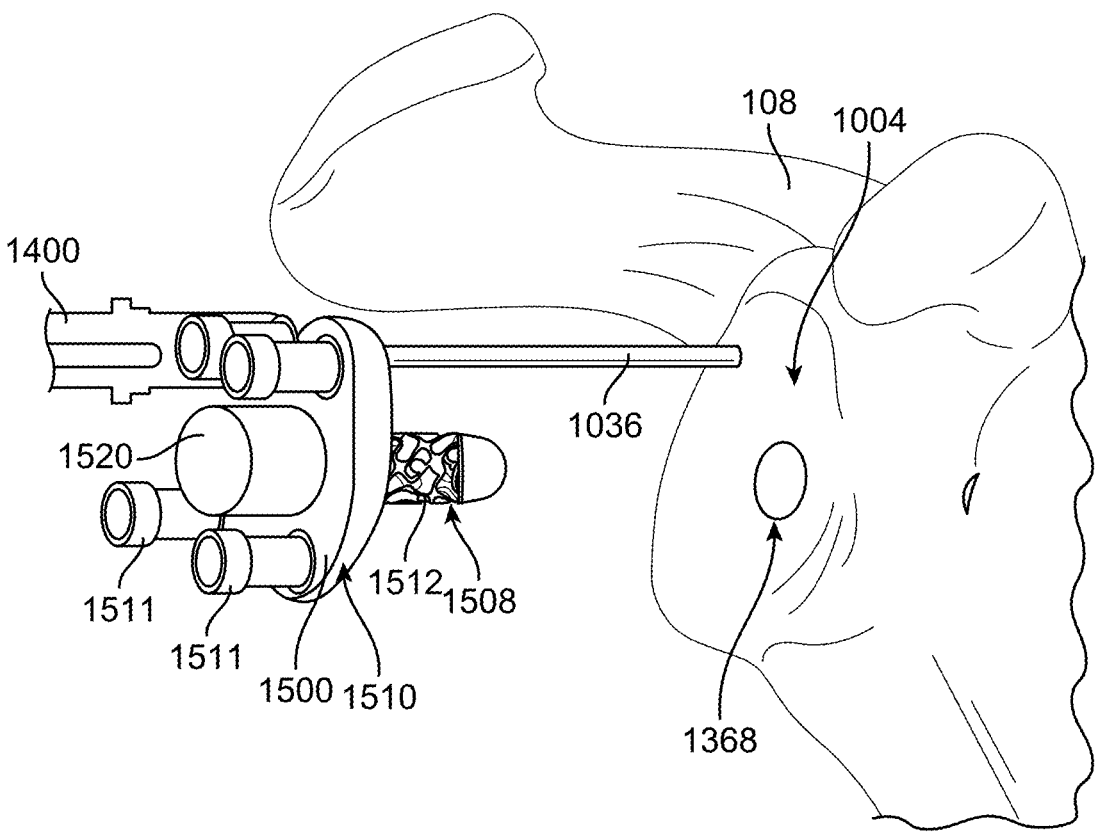
FIG. 20 is a side view of an exemplary baseplate approaching patient anatomy, according to at least one embodiment.

The baseplate 1500 in one embodiment comprises a series of drill guides 1511 removably affixed to apertures or peripheral fixation screw through-holes 1522, as depicted in FIG. 20. In some embodiments, the peripheral fixation screw through-holes comprise interior threads configured to receive the drill guides 1511 and peripheral fixation screws 1600, respectively. In embodiments of the baseplate comprising drill guides 1511, the drill guides 1511 may come pre-installed into the peripheral fixation screw through-holes. In some embodiments, the drill guides 1511 may be installed prior to use by a surgeon.

The drill guides 1511 may comprise an internal channel or opening configured to receive a drill bit. In these embodiments, there may be an equal number of drill guides 1511 installed into the baseplate 1500, such that each peripheral screw through-hole 1522 may have a drill guide 1511 affixed thereto. In some embodiments, where drilling at the planned locations of the peripheral screw through-holes 1522 may not be conducted, only some of the peripheral screw through-holes may be outfitted with drill guides 1511.

Figure 29:
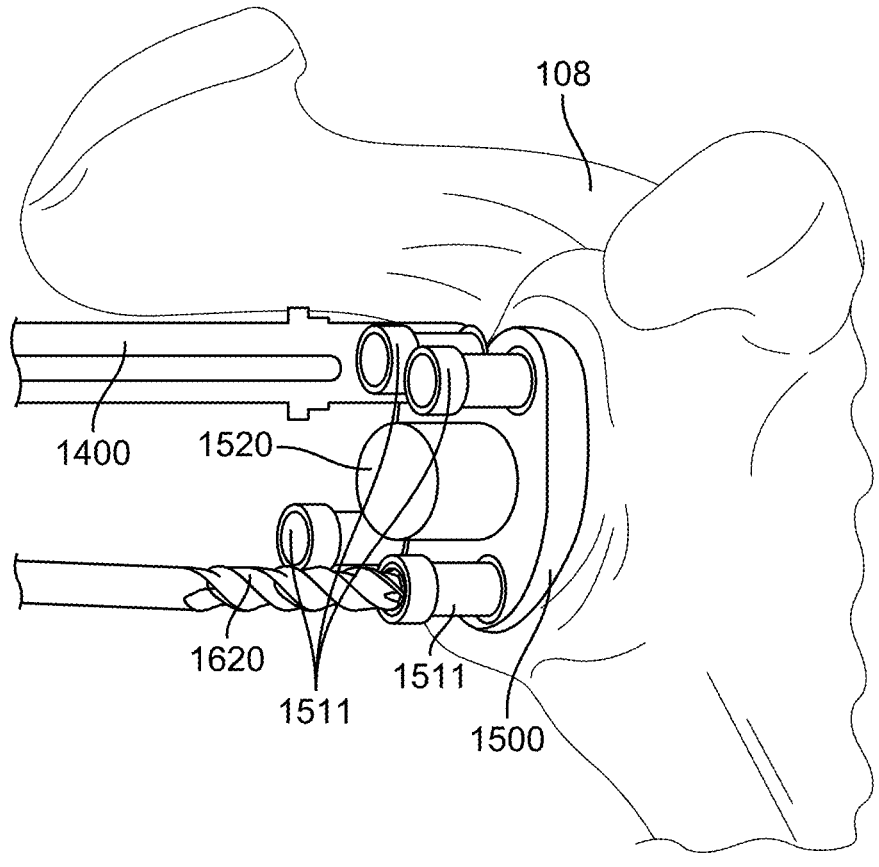
FIG. 29 is a perspective view of an exemplary baseplate and an exemplary screw guide interacting with patient anatomy, according to at least one embodiment.
Figure 30:
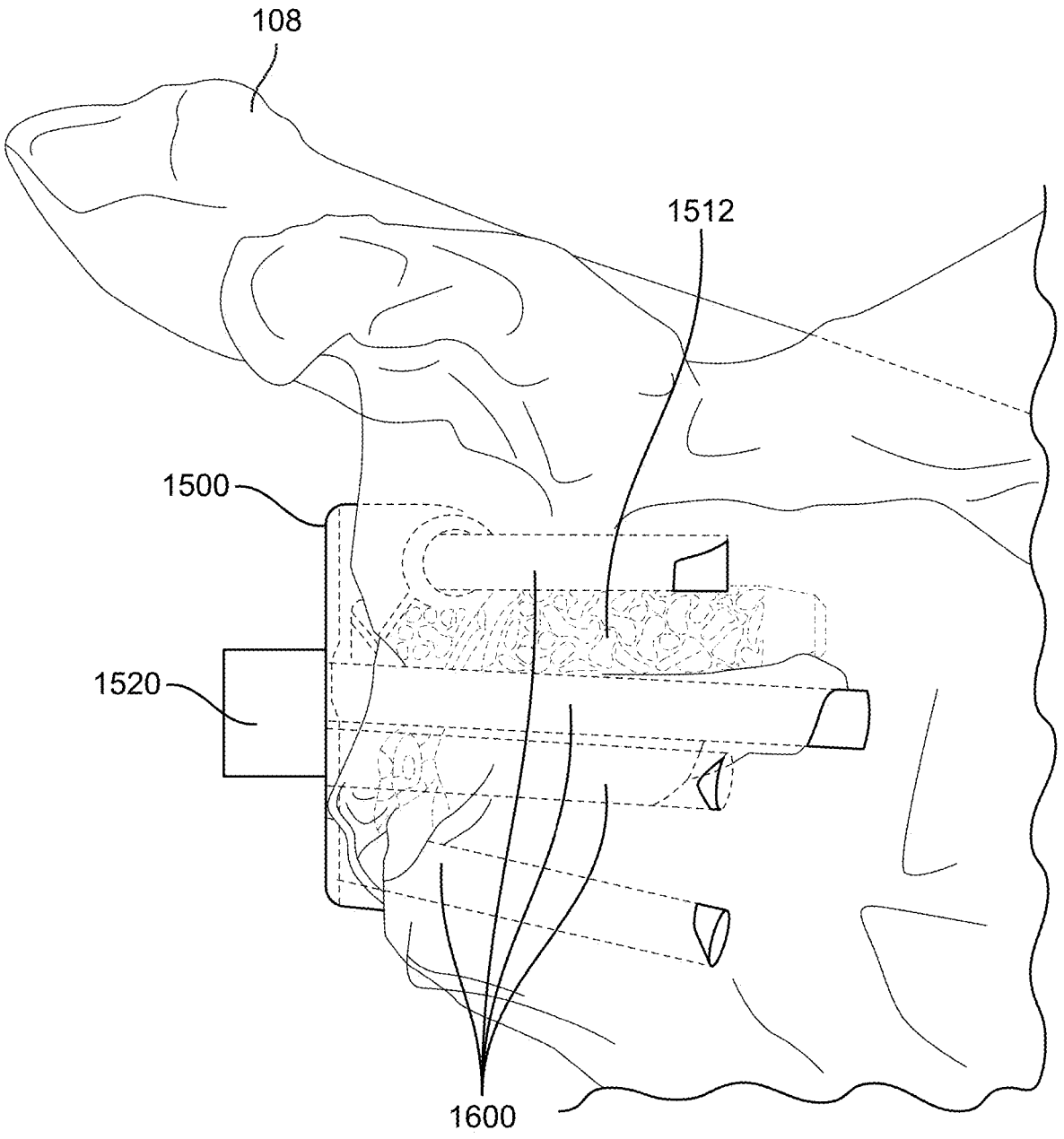
FIG. 30 is a first side view of an exemplary baseplate and screws interacting with patient anatomy, according to at least one embodiment.
Figure 31:
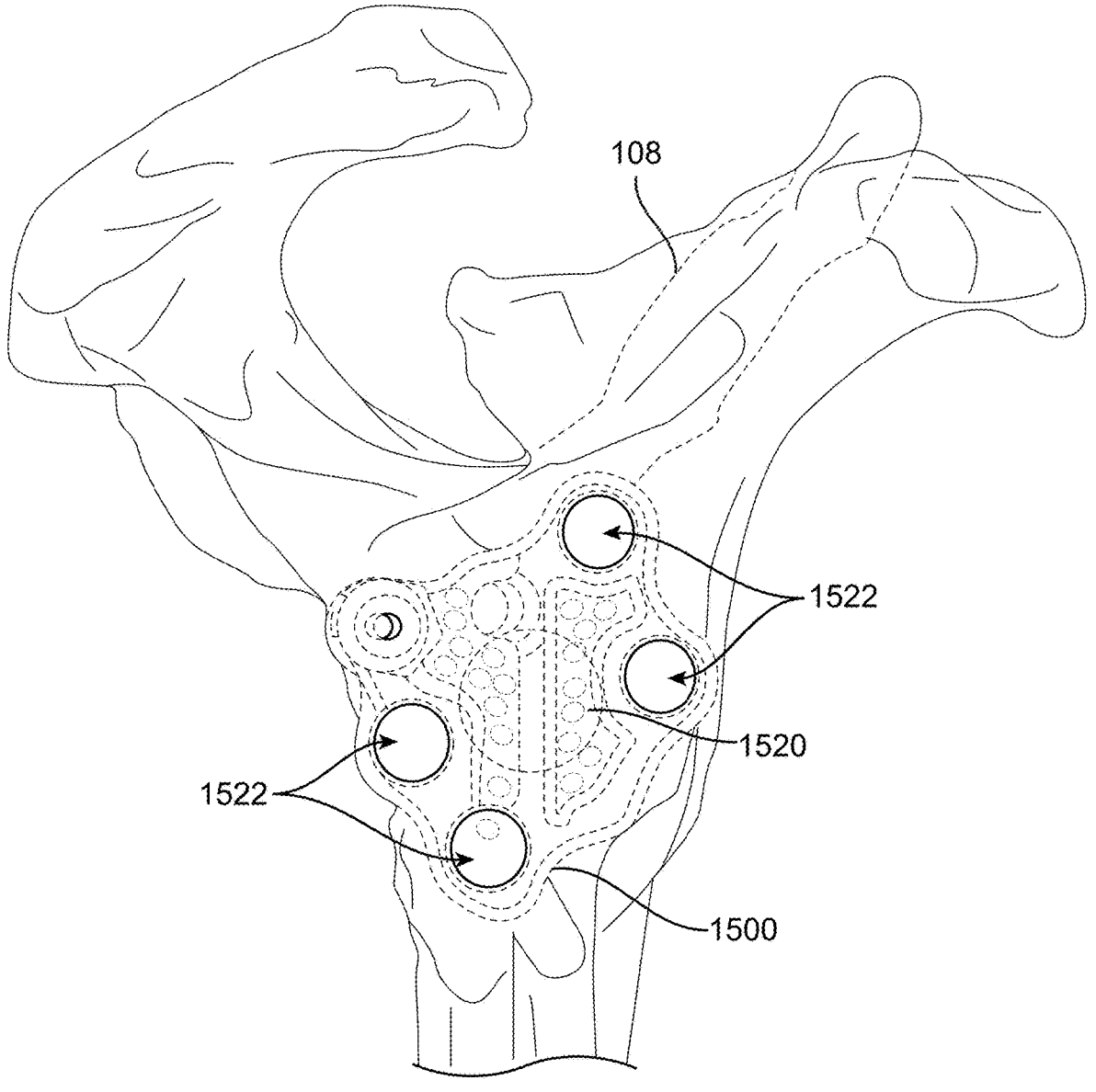
FIG. 31 is a front view of an exemplary baseplate and screws interacting with patient anatomy, according to at least one embodiment.
Figure 32:
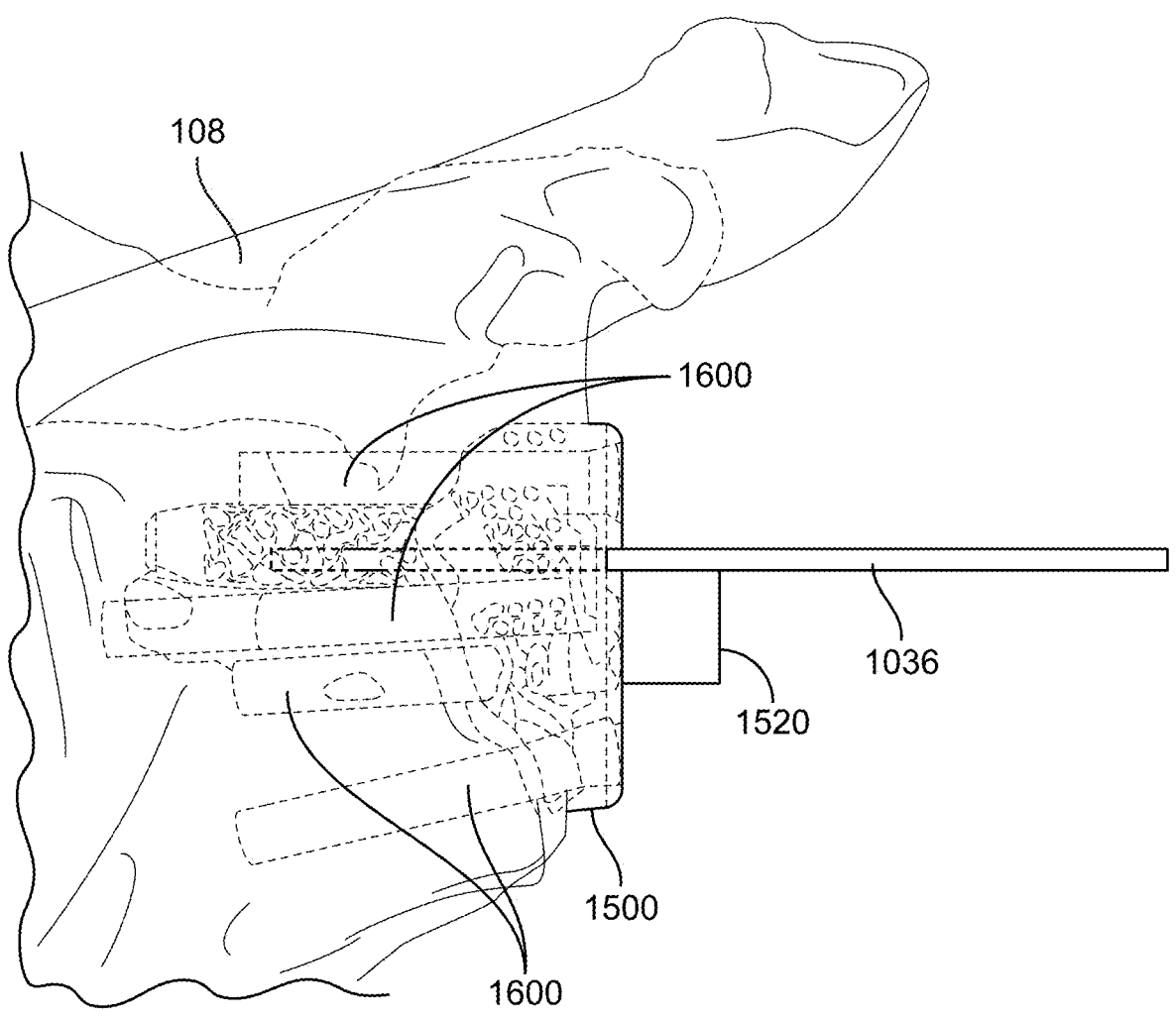
FIG. 32 is a second side view of an exemplary baseplate and screws interacting with patient anatomy, according to at least one embodiment.
Figure 33:
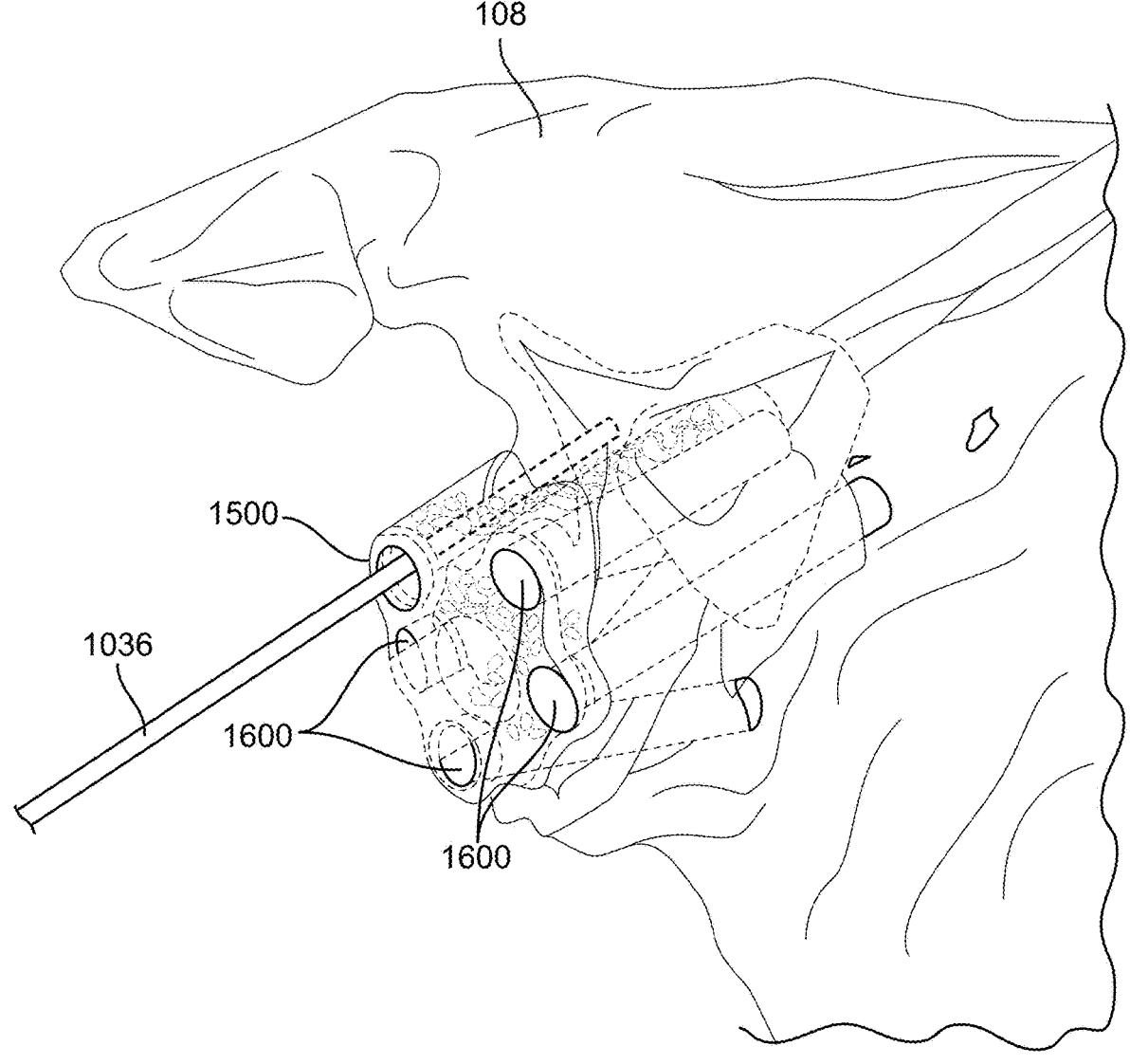
FIG. 33 is a perspective view of an exemplary baseplate and screws interacting with patient anatomy, according to at least one embodiment.
Figure 34:
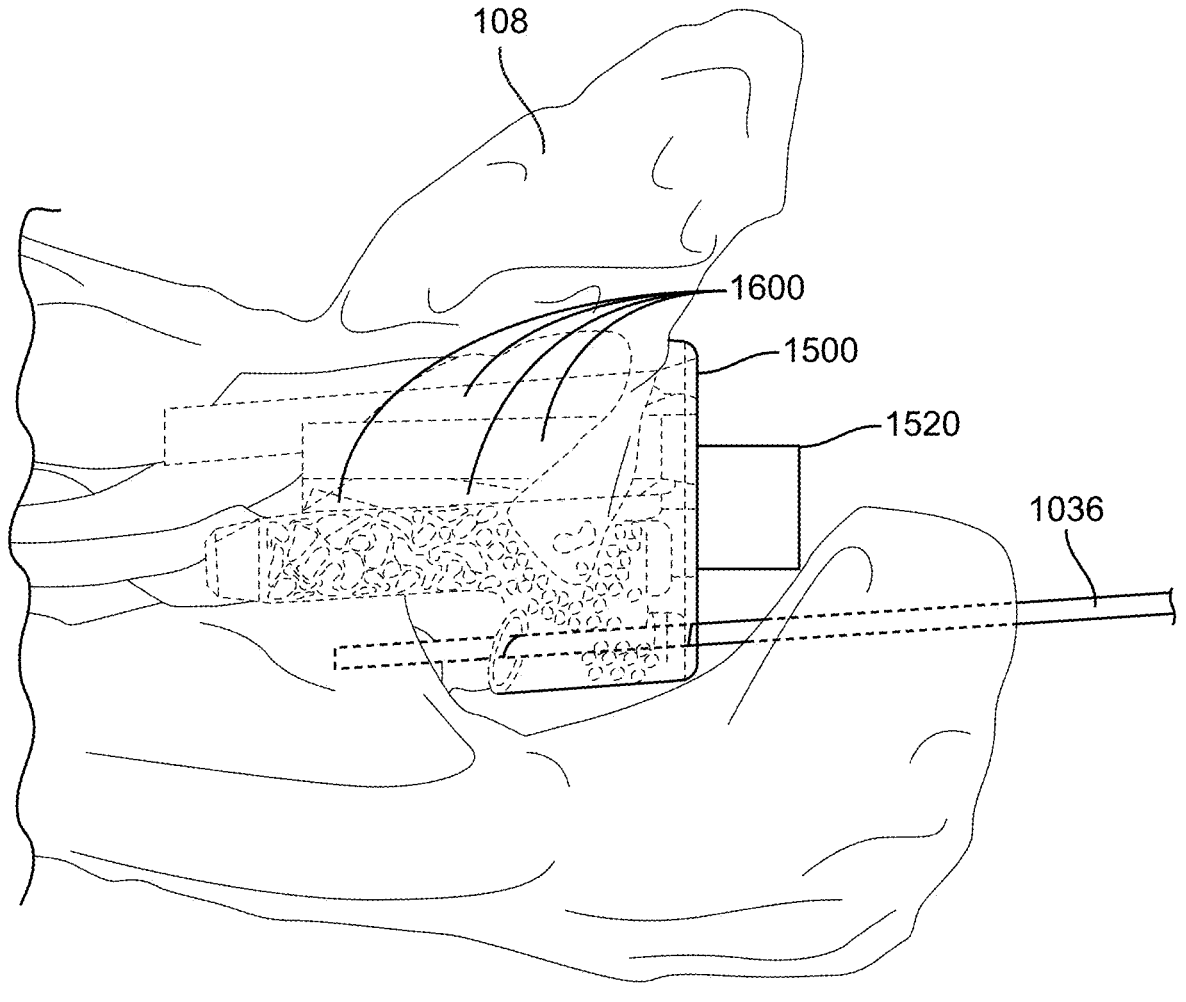
FIG. 34 is a third side view of an exemplary baseplate and screws interacting with patient anatomy, according to at least one embodiment.

The drill guides 1511 may guide the drilling of apertures in the bony surface 1004, to prepare the bony surface 1004 for the insertion of peripheral fixation screws 1600 (see FIG. 29). Once the apertures have been drilled into the bony surface 1004, the drill guide 1511 may be removed from the baseplate 1500 by unscrewing the drill guides 1511 from the peripheral fixation screw through-holes 1522. Then, as will be discussed further below, the peripheral fixation screws 1600 can be installed into the peripheral fixation screw through-holes 1522.

The peripheral fixation screws 1600 may be included to reinforce the attachment of the baseplate 1500 to the bony surface 1004 of the scapula 108. A quantity of peripheral fixation screws 1600 may be patient-specific: in one embodiment, the surgeon may elect to use between one and ten screws, or between two and eight screws, or between three and seven screws, or between four and six screws. In one embodiment, the surgeon may use other means of attachment to secure the baseplate 1500 to the bony surface 1004. In some cases, the locations of the peripheral fixation screw through-holes 1522 are selected to optimize fixation of the peripheral fixation screws 1600 into the bony surface.

Figure 21:
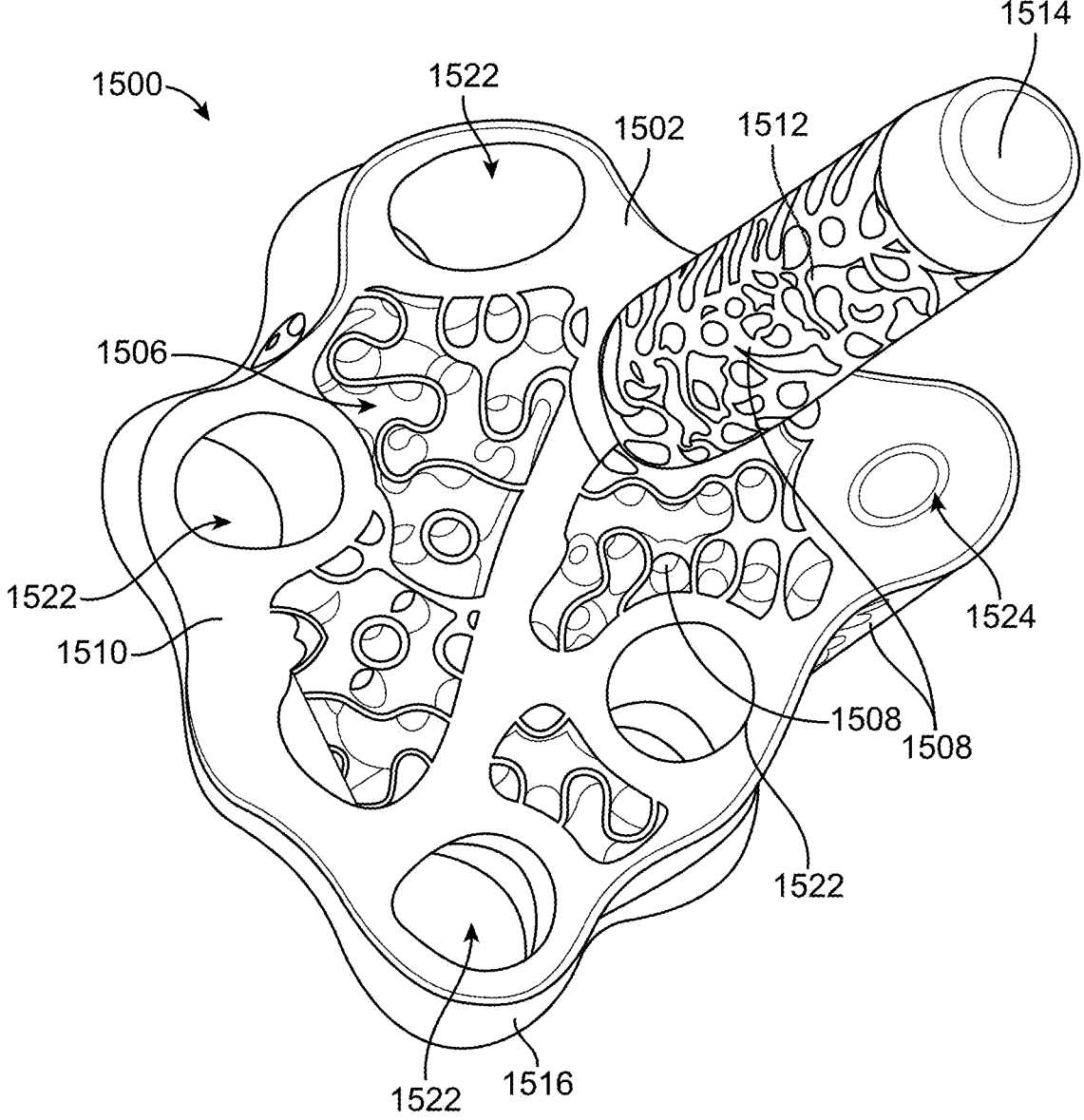
FIG. 21 is a perspective view of an exemplary baseplate, according to at least one embodiment.

In an exemplary embodiment, the baseplate 1500 comprises a first end 1502, a second end 1504, a periphery 1516, a patient-specific surface 1506, a post 1512, a post tip 1514, peripheral fixation screw through-holes 1522, and a guide opening 1524 (see FIG. 21). The first end 1502 is configured to be medial facing, towards the surgical site. The second end 1504 is configured to be lateral facing, away from the surgical site. The periphery 1516 can connect the first end 1502 to the second end 1504. The periphery 1516 can comprise a first thickness 1586 and a second thickness 1570. The first thickness 1586 can be greater than the second thickness 1570 such that the baseplate 1500 can sit flush with the anatomy of the surgical site of the particular patient. In some embodiments, the first thickness 1586 and the second thickness 1570 can be equivalent. In other embodiments, the first thickness 1586 can be less than the second thickness 1570. The patient-specific surface 1506 may be configured to abut, mate with, or otherwise interface with the interior of the surgical site. In some embodiments, the perimeter of the patient-specific surface 1506 is optimized to each patient's surgical site. The perimeter may be generally circular, generally ovular, generally polygonal, or any combination of shapes. Some areas of the perimeter can be concave or convex to accommodate removed or preserved tissue. Some areas of the perimeter may be generally straight or angular. The dimensions, contours, and angulations of the patient-specific surface 1506 can all be particularized to the surgical site of the patient.

In embodiments where the first thickness 1586 is not equal to the second thickness 1570, the baseplate 1500 is oriented at an angle A with respect to Friedman's Line. To define this angle, a plane P (not shown) can be defined as perpendicularly bisecting the first end 1502 of the baseplate. The plane P may extend lengthwise to the periphery 1516 of the baseplate 1500, thereby intersecting the periphery 1516 at two points along the periphery 1516 located on opposite sides. In some embodiments, the two points comprise a first point on the periphery 1516 furthest from the center of the patient-specific surface 1506 and a second point on the periphery 1516 closest to the center of the patient-specific surface 1506. Angle A may then be calculated as the angle between plane P and Friedman's Line in any suitable way, such as, for example using the following mathematical formula:

$$\Phi = \sin^{-1}\left|\frac{\vec{b}\cdot\vec{n}}{|\vec{b}|\cdot|\vec{n}|}\right|,$$

wherein Φ denotes an angle measurement, such as the angle A, and vectors $\vec{b}$ and $\vec{n}$ denote vector projections of Friedman's Line and a normal line to the plane P, respectively.

Hence, in some embodiments, the baseplate 1500 is customized such that the first end 1502, Friedman's Line, and the post 1512 are all imparted with different trajectories, per the specific anatomical conditions of the patient.

Further, the patient-specific surface 1506 may be textured and comprise additional features specific to the surface of the bony surface 1004, such as divots, angle changes, slopes, textures, or any combination thereof. In some embodiments, the patient-specific surface 1506 can comprise divots to accommodate areas of the surgical site where there are small regions of tissue. In other embodiments, the patient-specific surface 1506 can comprise slopes and/or angle changes to accommodate healthy areas of bone or tissue.

Additionally, the patient-specific surface 1506 may comprise a porous surface 1508 and a smooth surface 1510. For example, in the embodiment depicted in FIG. 21, the patient-specific surface 1506 comprises both a porous surface 1508 and a smooth surface 1510. However, it is contemplated that the patient-specific surface 1506 can have different configurations of porous surfaces 1508 and smooth surfaces 1510, depending on the particular patient's anatomy (or for other reasons). For example, in the exemplary embodiment depicted, the porous surface 1508 extends through the periphery 1516 and the post 1512 comprises an entirely porous surface 1508, with the exception of the post tip 1514. In other embodiments, the porous surface 1508 might only extend through the post 1512 and not the periphery 1516. Throughout the baseplate 1500 structure, the porous surface 1508 can be arranged on top of or below or beside the smooth surface 1510.

In at least one embodiment, the porous surface 1508 can comprise a sheet-based triply periodic, minimal surface (TPMS) architecture. In exemplary embodiments, the TPMS architecture of the porous surface 1508 comprises an arrangement of Schwarz-diamond lattices, gyroid lattices, or Schwarz-primitive lattices. The TPMS architecture can be integrally formed with other parts of the device. Further, the arrangement of lattices can vary the porosity throughout the porous surface 1508, such that some areas of the porous surface 1508 may have a higher or lower porosity than other areas of the porous surface 1508. The TPMS architecture can promote osseointegration because of a high surface area to volume ratio and a porosity, while minimizing points of stress concentration. Exemplary sheet based TPMS structures are further discussed in U.S. Pat. No. 11,484,413, filed May 7, 2021, and entitled "SHEET BASED TRIPLY PERIODIC MINIMAL SURFACE IMPLANTS FOR PROMOTING OSSEOINTEGRATION AND METHODS FOR PRODUCING SAME," incorporated by reference herein in its entirety. While it is contemplated that the porous surfaces 1508 comprises TPMS architecture, in other embodiments, other types of porous architecture may be suitable and a single device or instrument may include more than one type of porous architecture, pore structure, depth of pores, and/or pore diameter.

Because the baseplate can be customized for a particular patient, the dimensions of the baseplate can be particular to that patient. The baseplate 1500 has a total height 1578, a total width 1580, a total thickness 1582, and a total length 1586. For example, the total height 1578 can be 10 mm, the total width 1580 can be 15 mm, the total thickness 1582 can be 6 mm, and the total length 1586 can be 15 mm. In another embodiment, the total height 1578 can be 20 mm, the total width 1580 can be 30 mm, the total thickness 1582 can be 8 mm, and the total length 1586 can be 50 mm. These dimensions can be modified to suit the anatomy of the particular patient. For example, the total length total length 1586 may be anywhere between 3 and 100 mm.

Figure 22:
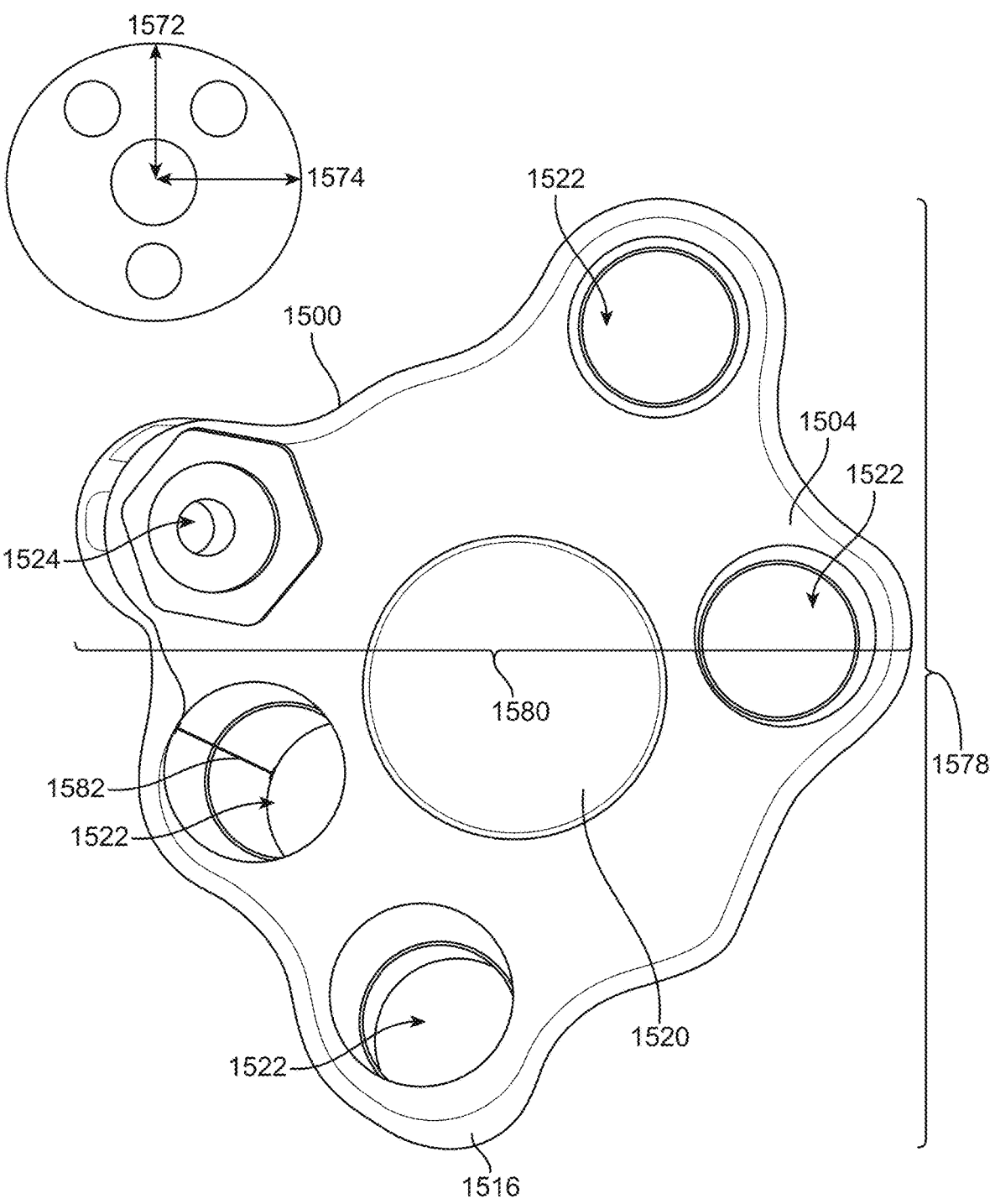
FIG. 22 is a back view of an exemplary baseplate, according to at least one embodiment.
Figure 23:
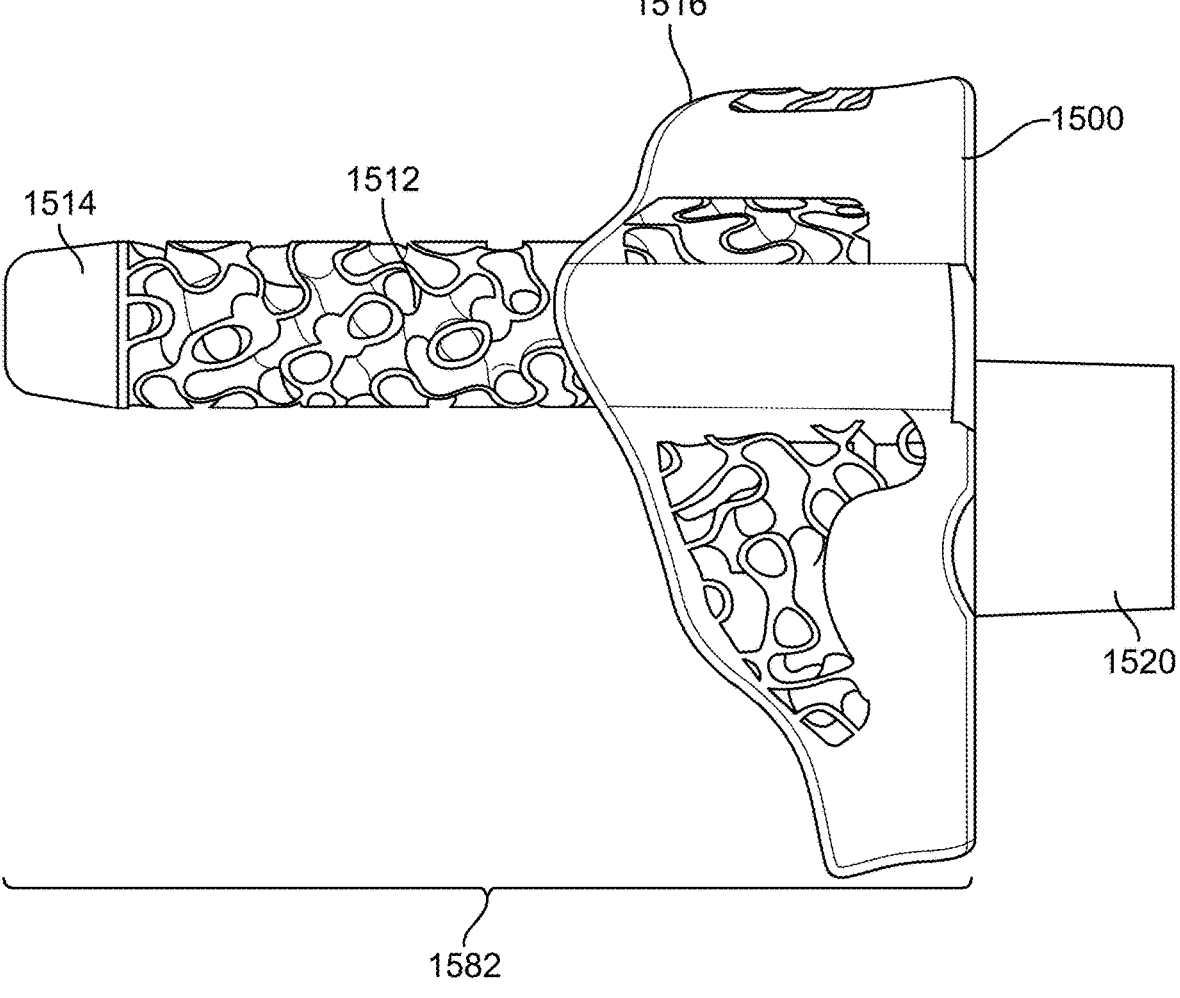
FIG. 23 is a first side view of an exemplary baseplate, according to at least one embodiment.
Figure 24:
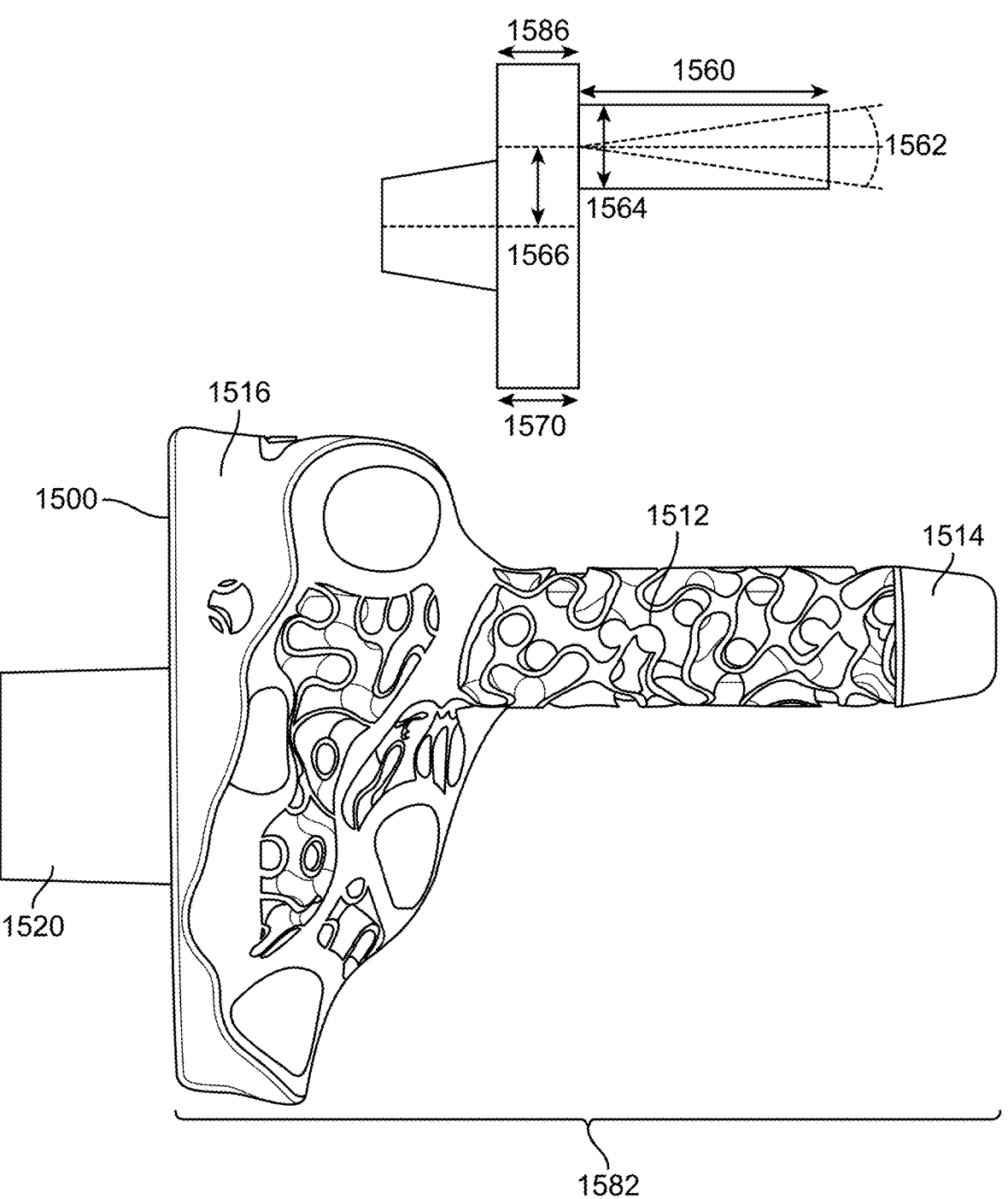
FIG. 24 is a second side view of an exemplary baseplate, according to at least one embodiment.
Figure 25:
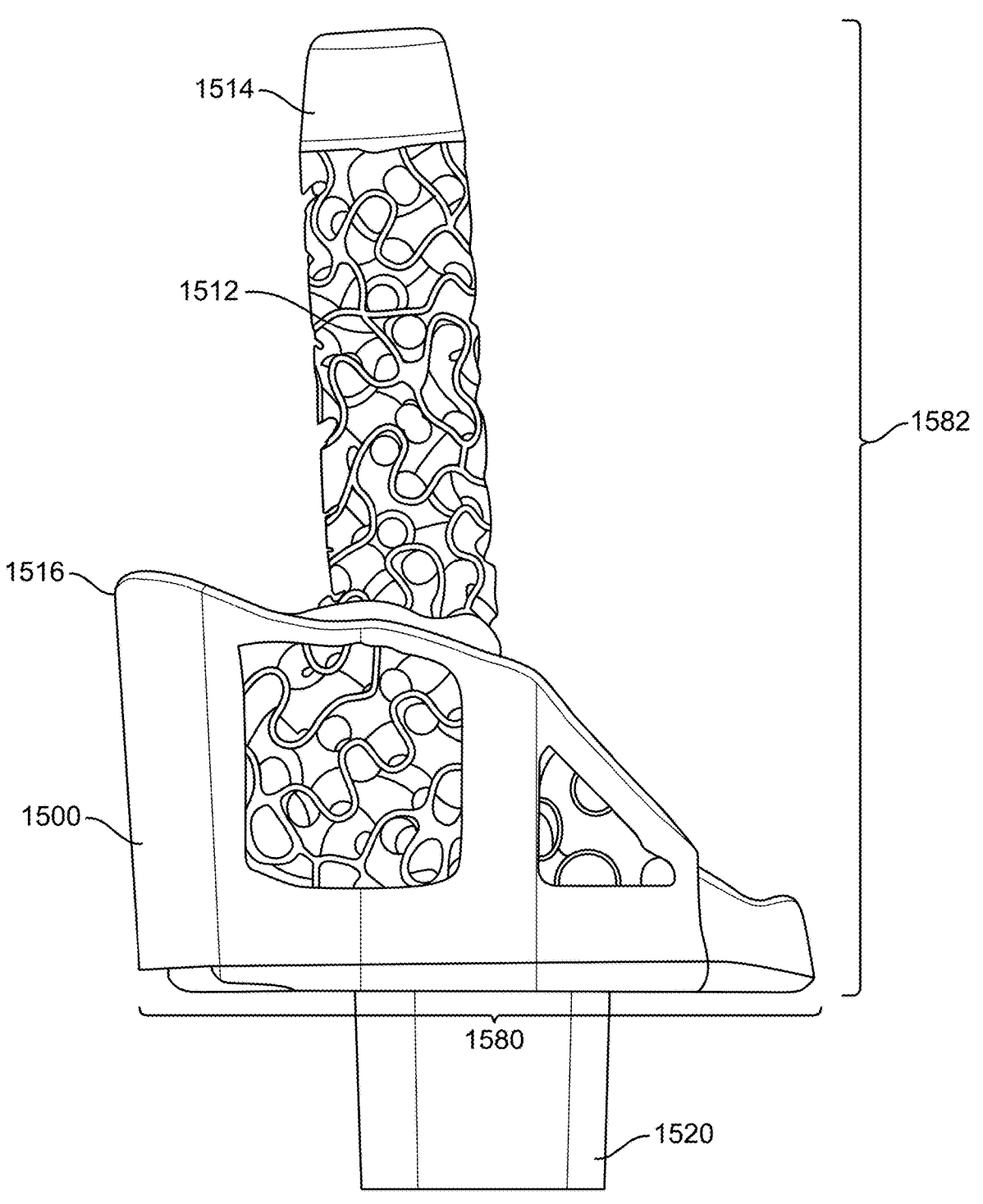
FIG. 25 is a third side view of an exemplary baseplate, according to at least one embodiment.

There are four peripheral fixation screw through-holes 1522 depicted in the exemplary embodiment of FIG. 22, but it is contemplated that a fewer or greater number of peripheral fixation screw through-holes 1522 could be suitable. For example, one patient may only use two peripheral fixation screws to secure the baseplate 1500 to their surgical site, and thus only two peripheral fixation screw through-holes 1522 are included. Another exemplary patient may use five peripheral fixation screws, and thus the baseplate 1500 comprises five peripheral fixation screw through-holes 1522.

The baseplate 1500 further comprises a taper 1520. The taper is configured to receive the glenosphere, discussed herein. The taper 1520 has a vertical distance 1572 and a horizontal distance 1574 from the periphery 1516 of the baseplate 1500. The vertical distance 1572 and the horizontal distance 1574 may be patient-specific, such that the taper 1520 can be located anywhere on the second end 1504 of the baseplate 1500. For example, the vertical distance 1572 can be 5 mm and the horizontal distance 1574 can be 8 mm. In other exemplary embodiments, the vertical distance 1572 can be 2, 3, 4, 5, 6, or 7 mm and the horizontal distance 1574 can be 2, 3, 4, 5, 6, or 7 mm. In one embodiment, the taper 1520 may be coupled to the second end 1504 of the baseplate 1500. In another embodiment, the taper 1520 may be integrally formed with the baseplate 1500, or affixed to the baseplate 1500 such as by welding, adhesives, or fasteners. The taper 1520 may extend laterally from the second end 1504, opposite of the post 1512.

The dimensions of the post 1512 can be particularized to the patient's anatomy, including a particular post length 1560, a post angulation 1562, a post diameter 1564, and a post offset 1566. The post offset 1566 refers to the distance between the center point of the post 1512 and the center point of the taper 1520. The post angulation 1562 can be adjusted greater or less than a right angle, as desired by the angulation of the patient's glenoid cavity or other bone and patient-specific considerations. The post angulation 1562 can be defined with respect to Friedman's Line. In such embodiments, the post angulation 1562 comprises the angle between the post 1512 and the Friedman's Line, and may be between 0° and 90°, or more specifically between 2° and 88°. The post angulation 1562 may be determined in any suitable way know to one of skill in the art. In one non-limiting example, to determine the post angulation 1562, the post 1512 and the Friedman's Line have respective direction ratios, represented as $(a_1, b_1, c_1)$ for the Friedman's Line and $(a_2, b_2, c_2)$ for the post 1512. The post angulation can then be computed according to the following equation:

$$\cos\theta = \frac{a_1 a_2 + b_1 b_2 + c_1 c_2}{\sqrt{a_1^2 + b_1^2 + c_1^2} \cdot \sqrt{a_2^2 + b_2^2 + c_2^2}}$$

For example, in a surgical plan where bone density (or better/less damaged bone) is towards the top of the patient's shoulder, the post angulation 1562 can be between 0° and 90°, or, more specifically, between 2° and 88° upwards with respect to the Friedman's Line. In a different exemplary surgical plan, where bone density or better/less damaged bone skews downwards towards the patient's chest, the post angulation 1562 can between 90° and 180°, or, more specifically, between 2° and 88° downwards with respect to the Friedman's Line.

Similarly, the taper 1520 can extend from the second end 1504 at a taper angle (not depicted). The taper angle can be defined with respect to the Friedman's Line and may be between 0° and 90°, or, more specifically, between 2° and 88°. The taper angle can be determined using the same method as the post angulation 1562, using the taper 1520 and the Friedman's Line's respective direction ratios.

The post offset 1566 similarly can be any length less than the total width 1580 of the baseplate. This enables the optimization of not only the location of the post 1512, the taper 1520, and, by proxy, the glenosphere that will couple with the taper 1520, because the location and angulation of the taper 1520 is not limited by the location or angle of the post 1512. As will be understood by one of ordinary skill in the art, the taper 1520 can be located anywhere on the second surface 1504. The post 1512 can be located anywhere on the first end 1502. In some embodiments, the post offset 1566 may be nearly zero, so that the post 1512 and the taper are in the same location on the respective ends 1502, 1504 of the baseplate 1500, relative to the top of the scapula 108. For example, in a surgical plan where an optimal or advantageous location of the baseplate is located towards the top of the scapula 108, the post offset 1566 can be 2 millimeters. In another exemplary surgical plan, where an optimal location of the baseplate is located in the center or bottom of the scapula 108, the post offset 1566 can be 6 millimeters.

Figure 26:
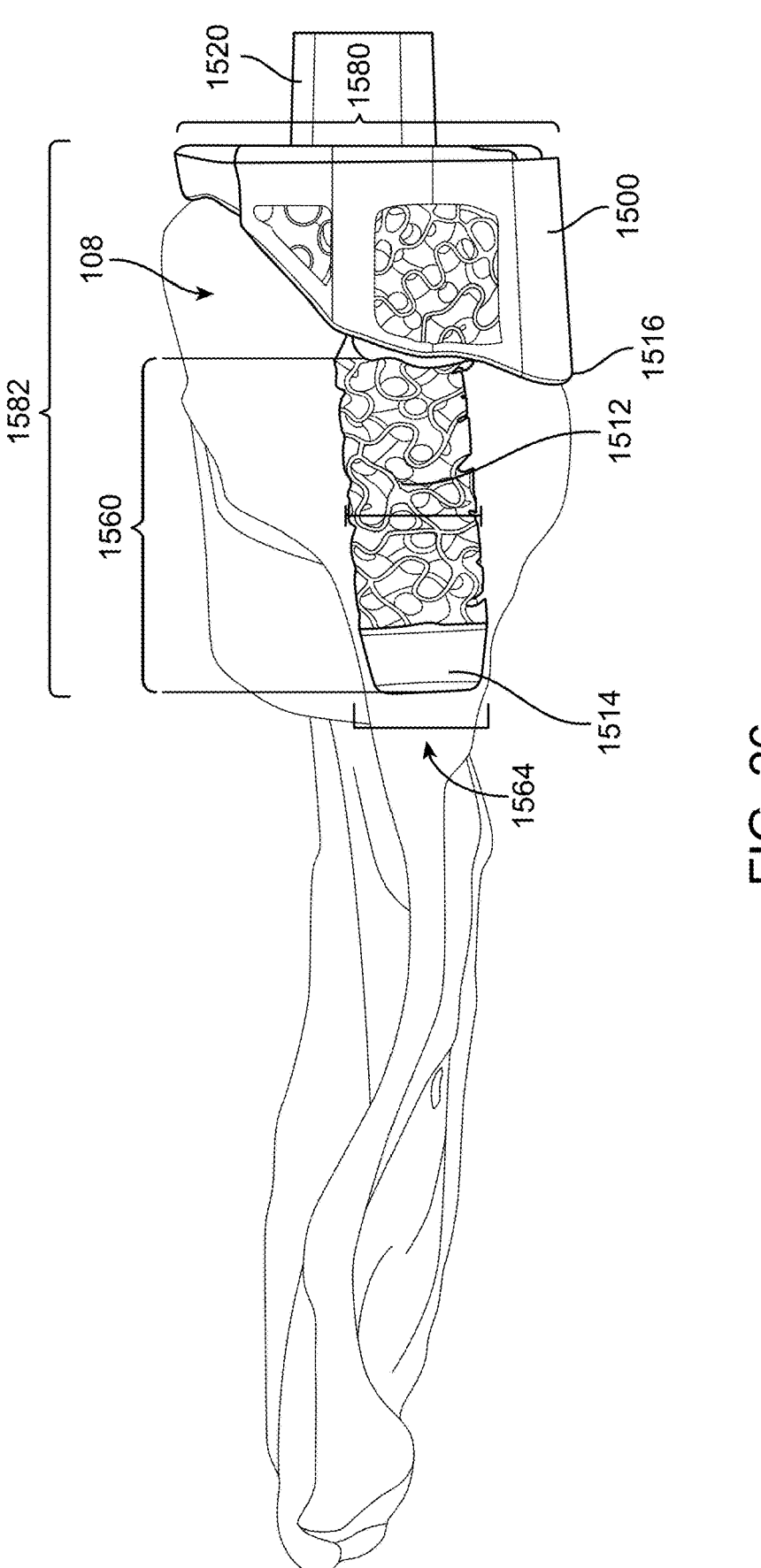
FIG. 26 is a first side view of an exemplary baseplate interaction with patient anatomy, according to at least one embodiment.
Figure 27:
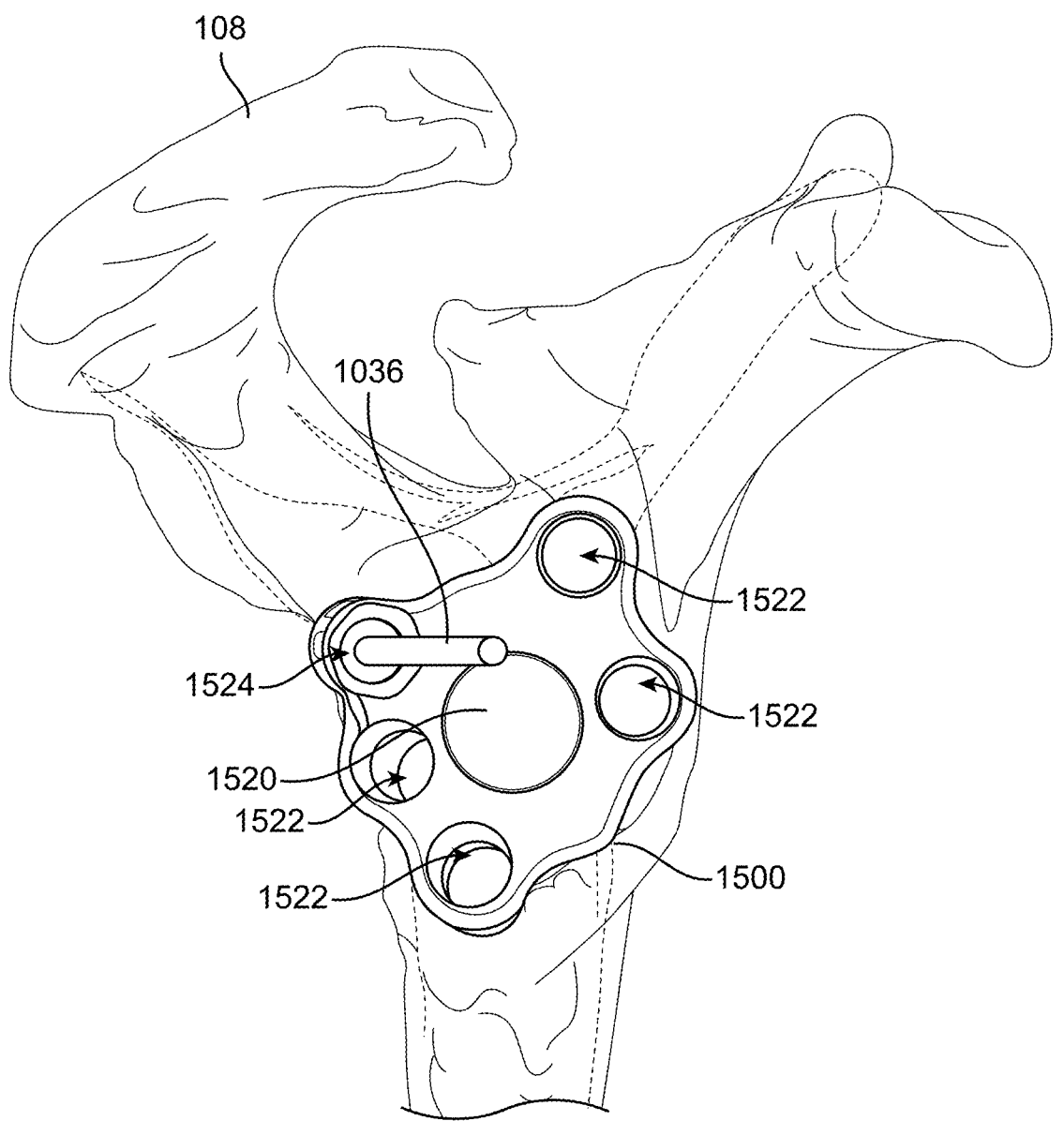
FIG. 27 is a front view of an exemplary baseplate interaction with patient anatomy, according to at least one embodiment.
Figure 28:
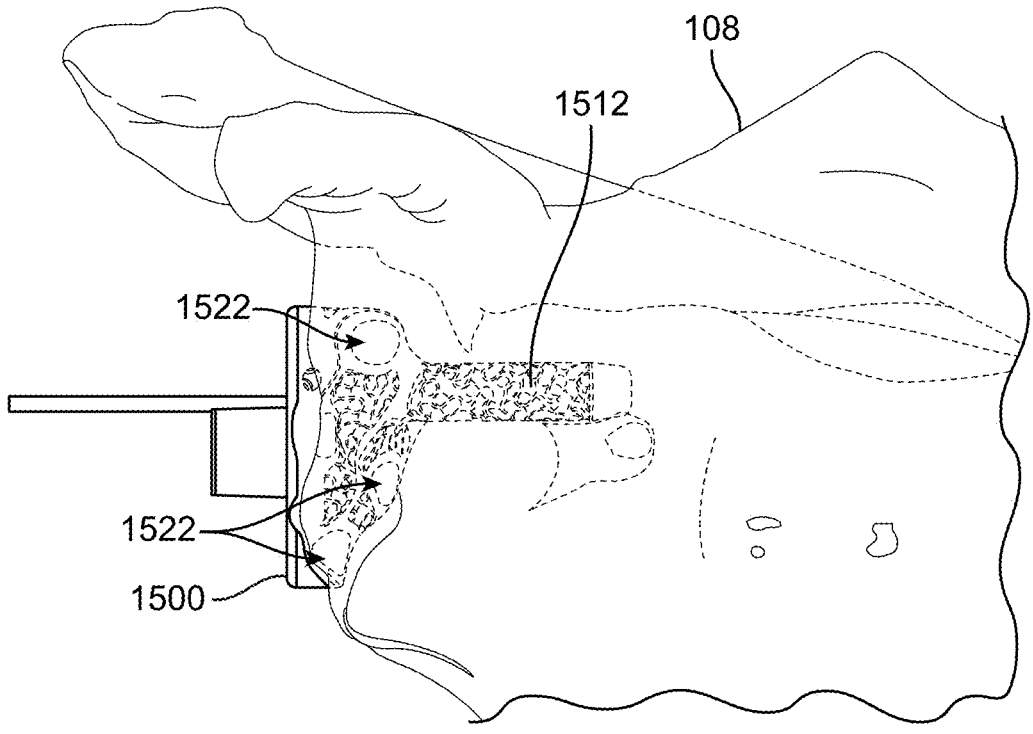
FIG. 28 is a second side view of an exemplary baseplate interaction with patient anatomy, according to at least one embodiment.

As an example of the above discussion, FIG. 26 depicts the baseplate 1500 inserted into the surgical site such that the patient-specific surface 1506 abuts the glenoid cavity and the post 1512 extends into the scapula 108. The post 1512 has a downward post angulation 1562 relative to the Friedman's Line, between 5° and 10°. The post length 1560, the post angulation 1562, and the post diameter 1564 are configured such that the post 1512 can be press-fit into directly into the bone of the glenoid cavity. The post offset 1566 is such that the taper 1520 is in an optimized position for the glenosphere to be located, relative to the scapula and the humerus.

In one embodiment, particular parameters of the post 1512 may be consistent across RSA procedures for different patients while other parameters are variable and customized for a particular patient. In one embodiment, the post diameter 1564 is between 1 and 15 mm, or between 2 and 10 mm, or between 3 and 9 mm, or between 5 and 8 mm, or between 7 and 7.5 mm. For example, the post diameter 1564 may be 7.3 mm for every patient. In another embodiment, the post diameter 1564 may be a unique value for each patient undergoing RSA surgery. In various embodiments, during the placement of the baseplate 1500 into the glenoid cavity, the guide opening 1524 is placed over an anti-rotation pin 1030, where the anti-rotation pin 1030 was placed earlier in the surgery, as discussed supra. The second end 1504 of the baseplate can face outward from the surgical site and the peripheral fixation screw through-holes 1522 are aligned with the desired location and at a predetermined angle for a set of peripheral fixation screws 1600. The taper 1520 extends away from the application site, such that the taper 1520 can receive the glenosphere after the completed installation of the baseplate 1500.

In an exemplary installation of the baseplate, a screw guide 1400 can be inserted into the guide opening 1524 (see FIG. 29). A series of drill guides 1511 may be loaded into the peripheral fixation screw though-holes 1522. The drill guides 1511 may be loaded one at a time, more than one at a time, or all at once. The drill guides 1511 can be loaded prior to the baseplate 1500 being packaged and/or sterilized or by the surgical team. In the exemplary embodiment, all of the drill guides 1511 have been loaded into the peripheral fixation screw through-holes 1522. A peripheral screw drill 1620 may be inserted through the opening of one of the drill guides 1511 and drilled into the bony surface 1004, such that an aperture for a peripheral screw can be made. This process is repeated at the location of each one of the drill guides 1511.

Once the apertures 1522 for the peripheral screws have been drilled into the bony surface 1004, the peripheral fixation screws 1600 can be inserted through the baseplate 1500 and into the created apertures 1522. When the peripheral fixation screw drill 1620 screws the peripheral fixation screws 1600 through the peripheral fixation screw through-holes 1522, the peripheral fixation screws 1600 enter the surgery site (see FIG. 30). The peripheral fixation screws 1600 may secure the post 1512 position within patient's bone and the periphery of the baseplate 1516 against the surgery site.

In various embodiments, throughout the securing of the peripheral fixation screws 1600, the anti-rotation pin 1030 remains inserted through the guide opening 1524 and within a portion of the scapula 108 (or surrounding anatomy). Once all of the peripheral fixation screws 1600 have been inserted into the scapula 108 and the baseplate 1500 is secured, the anti-rotation pin 1030 can be removed from the surgery site through the guide opening 1524.

After the baseplate 1500 has been properly secured to the glenoid cavity, a glenosphere 1800 can be inserted onto the baseplate 1500. The glenosphere 1800 may comprise a glenosphere surface 1802 and a recession or glenosphere aperture 1804. The glenosphere surface 1802 may be generally hemispherical in shape. The glenosphere aperture 1804 may be configured to mate with the taper 1520, affixing the glenosphere 1800 to the baseplate 1500. It is contemplated that the attachment of the glenosphere 1800 to the taper 1520 may be permanent, such as by adhesive, welding, or other suitable coupling methods, including by press-fit and/or via additional fasteners (e.g., screws or pins). The attachment method may also be impermanent where appropriate, and may occur through snap-fit type attachment methods, temporary fasteners, adhesives, etc. In some instances, it may be appropriate to insert a trial glenosphere to ensure proper shape, type, and fit prior to a final glenosphere insertion, dependent on the particular patient. In such cases, the trial glenosphere may be removably affixed to the taper 1520.

Figure 35:
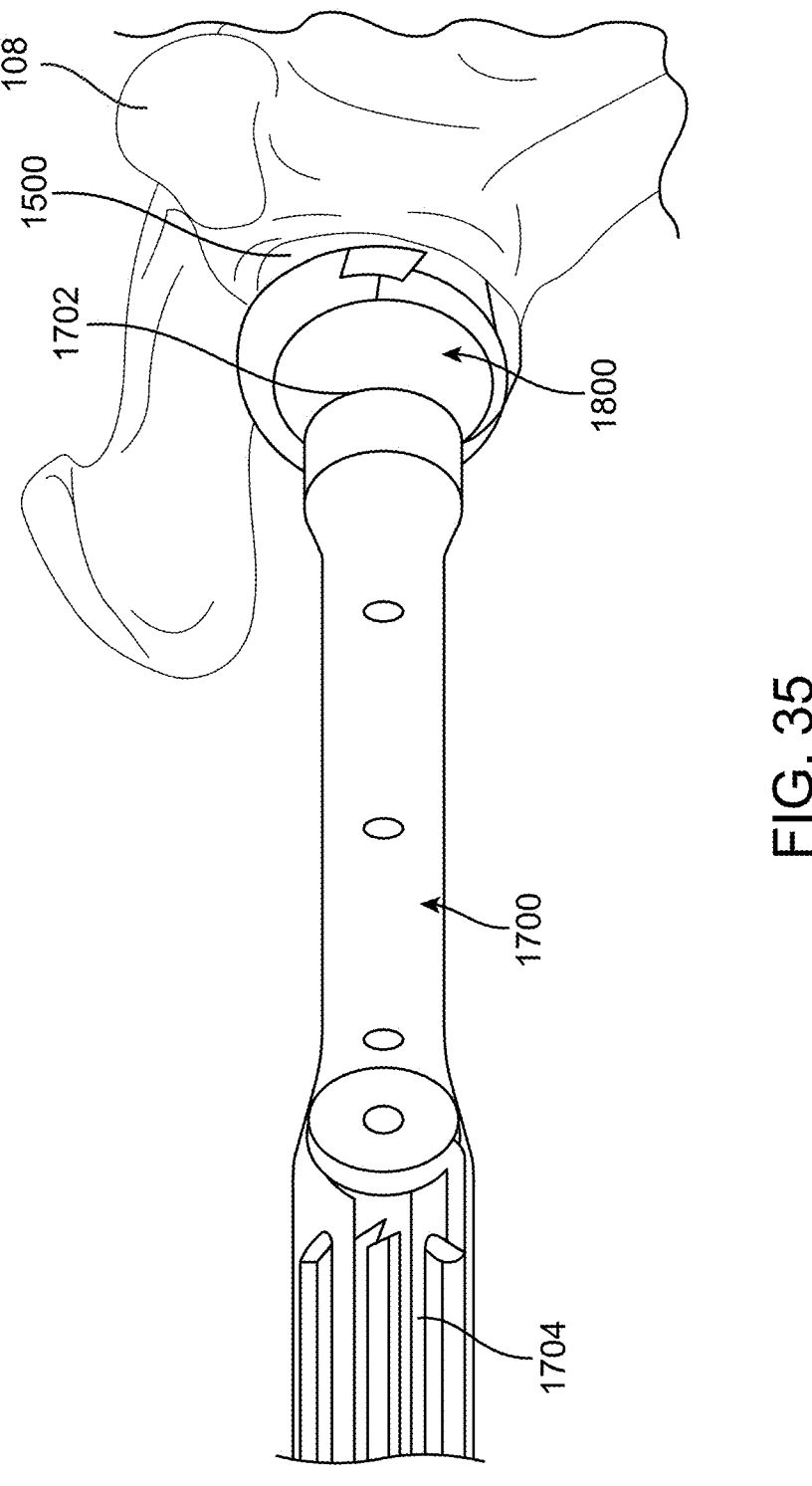
FIG. 35 is a perspective view of an exemplary glenosphere inserter interacting with patient anatomy, according to at least one embodiment.
Figure 36:
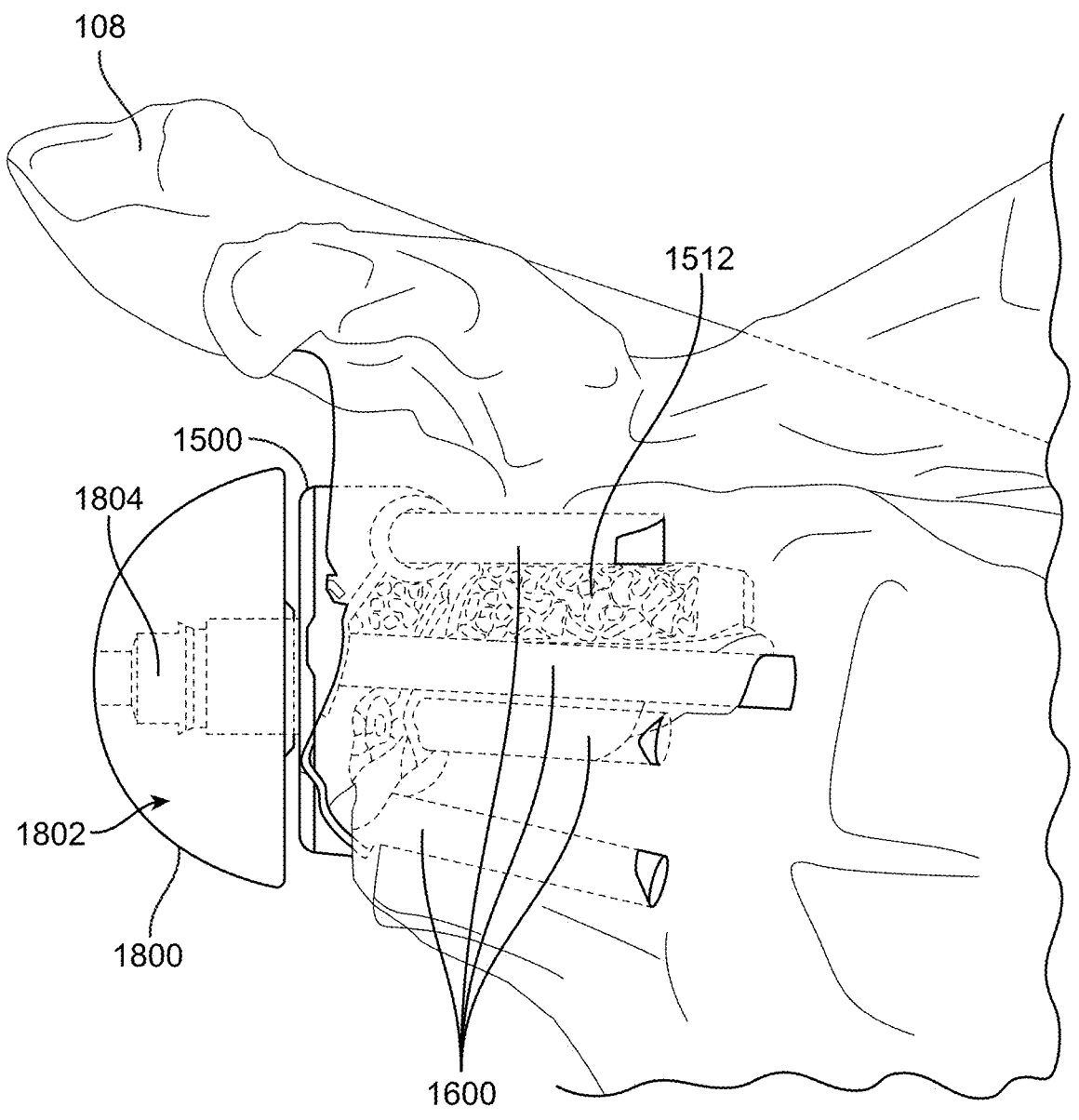
FIG. 36 is a side view of an exemplary glenoid system interacting with patient anatomy, according to at least one embodiment.
Figure 37:
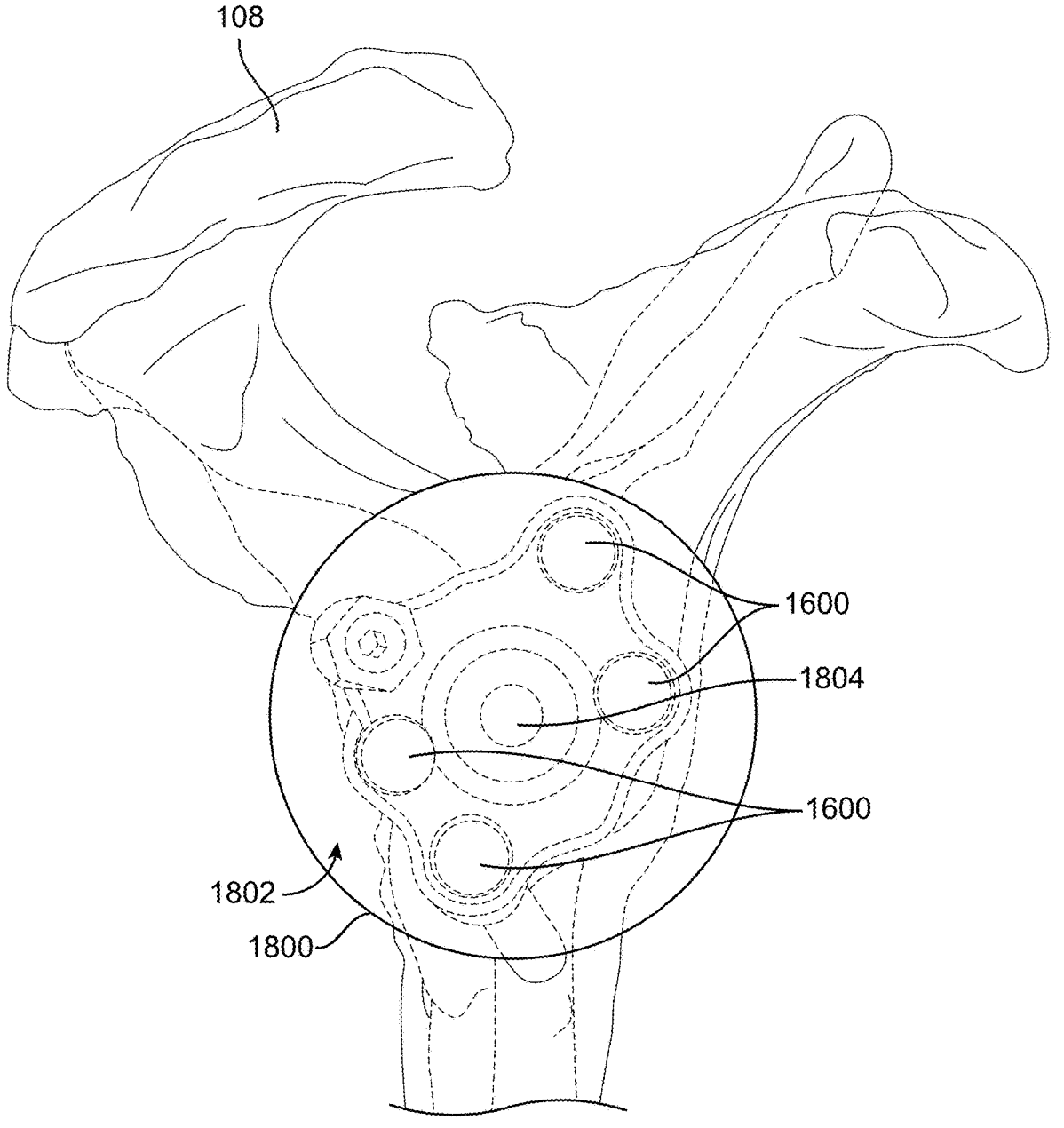
FIG. 37 is a front view of an exemplary glenoid system interacting with patient anatomy, according to at least one embodiment.
Figure 38:
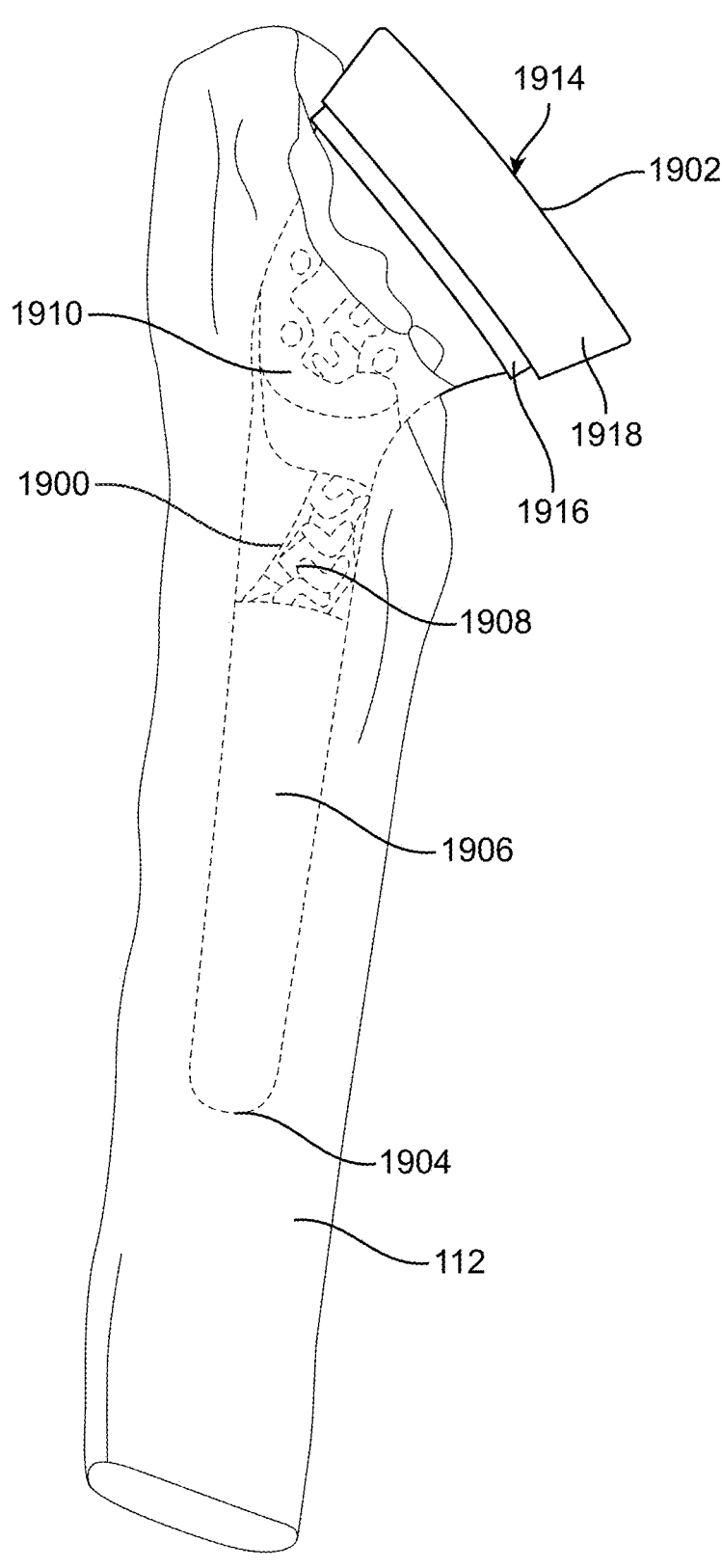
FIG. 38 is a side view of an exemplary humeral stem system interacting with patient anatomy, according to at least one embodiment.
Figure 39:
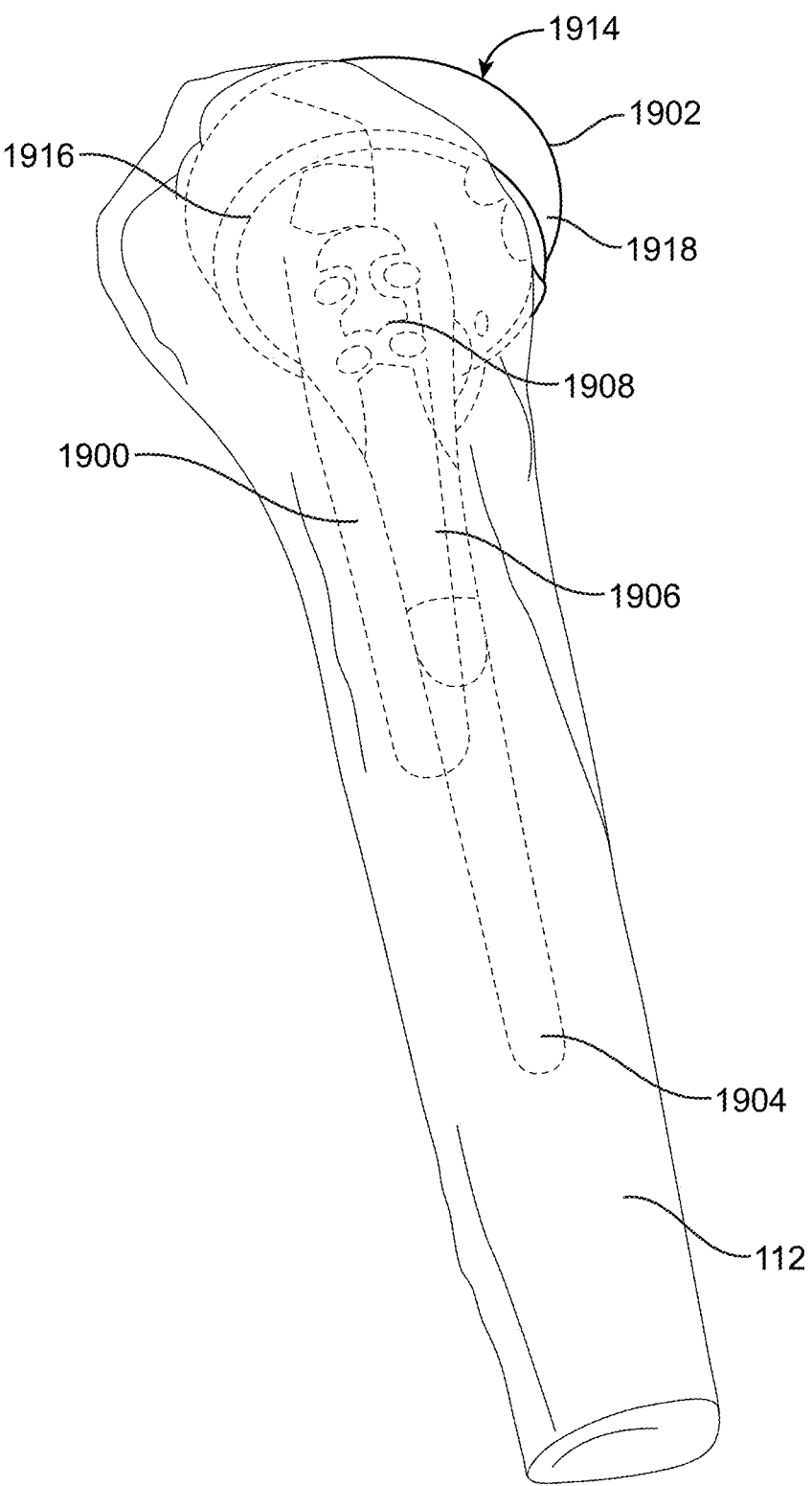
FIG. 39 is a perspective view of an exemplary humeral stem system interacting with patient anatomy, according to at least one embodiment.
Figure 40:
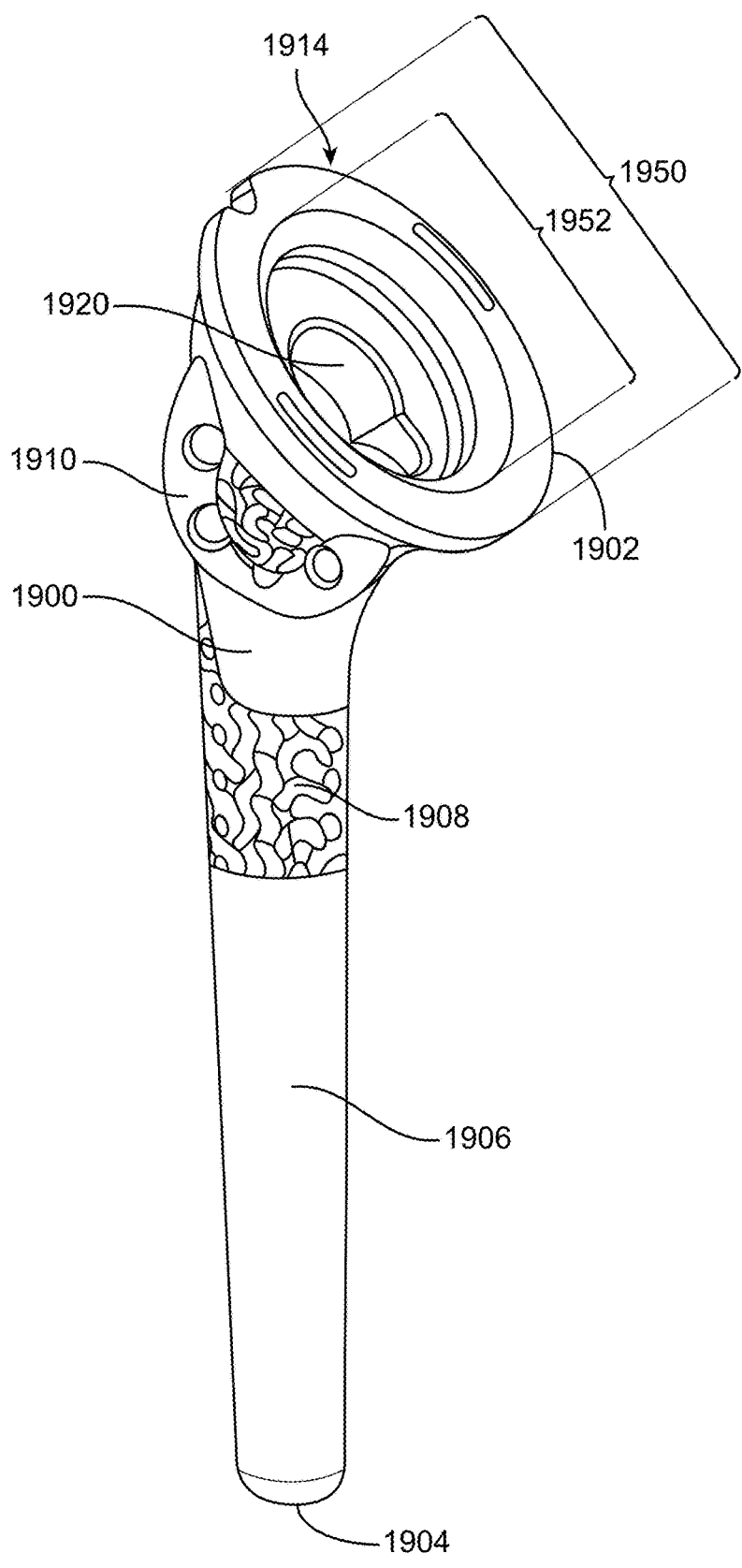
FIG. 40 is a perspective view of an exemplary humeral stem system, according to at least one embodiment.

To insert the glenosphere 1800, trial or final, the glenosphere may be removably inserted into a glenosphere inserter 1700 (see FIG. 35). The glenosphere inserter 1700 may comprise a first end 1702 configured to insert the glenosphere 1800 and a second end 1704 configured to be used as a handle. Once the surgeon has inserted the glenosphere 1800 onto the baseplate 1500 via the glenosphere inserter 1700, the glenosphere inserter 1700 may be removed from the surgery site. The glenosphere inserter 1700 can comprise surgically appropriate materials, such as metals or polymers. The glenosphere inserter 1700 may comprise a material that is suitable for use with common sterilization chemicals used in orthopedic surgeries, such that the material does not degrade after exposure to these chemicals. Further, the material may further be compatible with sterilization procedures such as autoclaves, such that the glenosphere inserter can be sterilized and used in multiple procedures. In alternate embodiments, the glenosphere inserter (or any of the instruments discussed herein) may be disposable.

The glenosphere 1800 may be configured to additionally mate with a humeral stem 1900. In embodiments, the humeral stem 1900 may comprise a first end 1902, a second end 1904, a shaft 1906, a humeral stem spout 1910, and a humeral stem opening 1914. In at least one embodiment, the second end 1904 extends into the glenoid cavity 104. In some embodiments, the humeral stem 1900 can comprise a third end (not depicted) that extends into the glenoid cavity similar to the second end 1904.

The first end 1902 comprises a tray 1916, a liner 1918, and the humeral stem opening 1914. The first end 1902 can be connected to the shaft 1906 via the humeral stem spout 1910. The humeral stem spout 1910 is configured to angle the first end 1902, similar to how the head of the humerus is angled in a human.

The shaft 1906 can comprise porous regions 1908 and smooth regions (not shown). The number of porous regions 1908 and smooth regions can be optimized, such as for encouraging tissue and bone growth around the humeral stem 1900. In some embodiments, the porous regions 1908 may only be on the surface of the shaft 1906 and the interior of the shaft 1906 can comprise smooth regions. In other embodiments, the shaft 1906 can comprise smooth regions on the surface and porous regions 1908 can extend beneath the smooth regions, giving the shaft 1906 a partially hollow structure. The porous region 1908 can comprise TPMS architecture. The TPMS architecture of the porous region 1908 may comprise layers of the various lattices, optimized to suit a particular patient's anatomy and encourage desired bone and tissue growth around and into the shaft 1906. It is contemplated that other porous structured materials may also be suitable for the porous region 1908.

In some embodiments, the tray 1916 and the liner 1918 may be removably affixed to the humeral stem 1900 and attached to the humeral stem 1900 prior to installation. The humeral stem opening 1914 further comprises a first diameter 1950, a second diameter 1952, and an attachment feature 1920. The tray 1916 and the liner 1918 can be attached to the humeral stem 1900 via the attachment feature 1920. The first diameter 1950 can define the outer edge of the humeral opening. The second diameter 1952 can define the inner edge of the humeral opening, where the tray 1916 and the liner 1918 are received.

In various embodiments, the liner 1918 is configured to receive the glenosphere 1800, while the tray 1916 beneath the liner 1918 supports the glenosphere 1800. In at least one embodiment, the liner 1918 is further configured to glide along the surface of the glenosphere 1800. This sliding motion of the glenosphere surface 1802 against the liner 1918 can mimic the natural movement of the ball and socket joint of a shoulder. In some embodiments, the glenosphere 1800 and the baseplate 1500 may be further affixed with a security screw (not depicted). The security screw may attach the glenosphere to the baseplate 1500 at the taper 1520 or some other suitable location.

Figure 41:
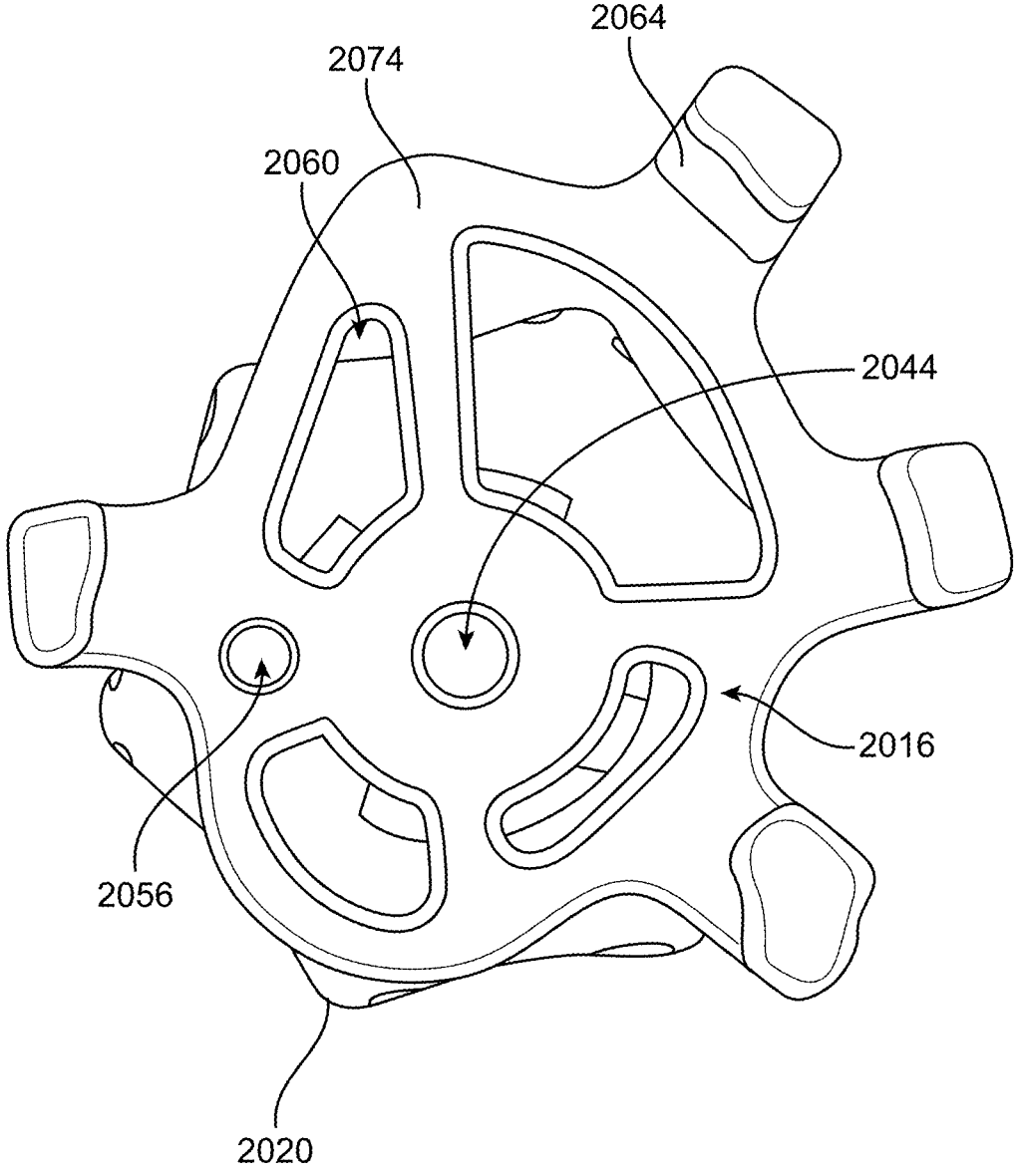
FIG. 41 is a front view of an exemplary pin guide, according to at least one embodiment.
Figure 42:
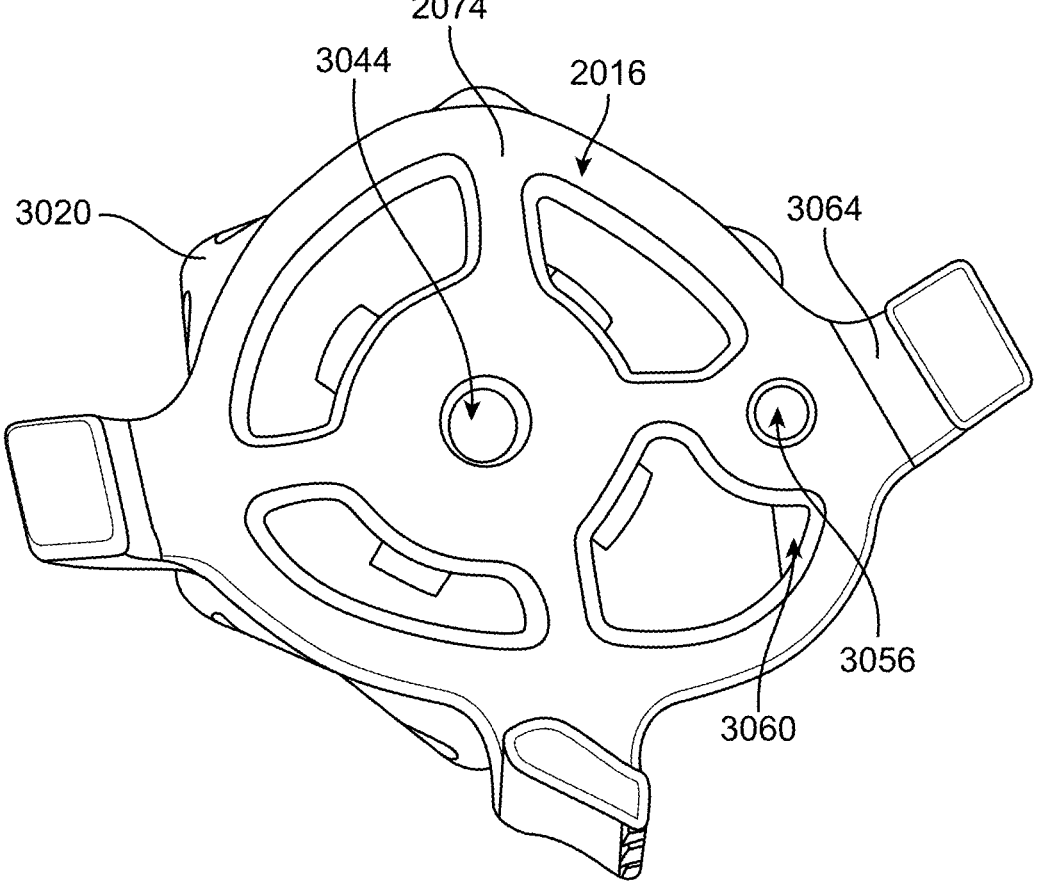
FIG. 42 is a front view of an exemplary pin guide, according to at least one embodiment.

Referring now to FIGS. 41 and 42, alternative embodiments 2000, 3000 of the pin guide 1000 (see, for example, FIG. 4) are shown. The alternative embodiments 2000, 3000 may be configured for use with a patient experiencing a higher, lower, or different level of damage to his/her scapula than the first exemplary patient. The pin guides 2000, 3000 may thus include features not present in the pin guide 1000, exclude features present in the pin guide 1000, or include features present in the pin guide 1000 in different shapes, sizes, orientations, locations, geometries, quantities, and/or compositions. In one embodiment, the pin guides 2000, 3000 appear substantially similar to the pin guide 1000.

For example, in one embodiment, the pin guides 2000, 3000 may include additional windows 2060, 3060 for improved visibility of an underlying bony surface (not shown). The shape and dimensions of the windows 2060, 3060 may be customized during design of a patient-specific face 2016, 3016 in response to the unique contours of the underlying bony surface. The number of windows 2060, 3060 may also be determined by the amount of material used for the patient-specific face 2016, 3016 to function. For example, the pin guide 2000, 3000 may be imparted with a greater number of windows owing for a desire for greater contact with the bony surface or a desire for higher structural integrity. The number of windows 2060, 3060 may also be modified in response to areas of the bony surface that the surgeon may prefer to visualize during use of the pin guides 2000, 3000. In one embodiment, the pin guides 2000, 3000 may comprise at least one, or at least two, or at least three, or at least four, or at least five windows 2060, depending on the design of the patient-specific face 2016, 3016. In one embodiment, such as those shown in FIGS. 41 and 42, the pin guide 2000, 3000 contains four windows.

Similarly, in one embodiment, the pin guides 2000, 3000 may include additional (or fewer) tabs 2064, 3064 for improved attachment to the scapula during use of the pin guides 2000, 3000. The tabs 2064 may be placed to allow for increased contact with the scapula such that the pin guides 2000, 3000 remain unmoving during use. For example, in one embodiment, the pin guides 2000, 3000 may include four tabs, as shown in FIG. 41. In one embodiment, the pin guides 2000, 3000 may comprise at least one, or at least two, or at least three, or at least four, or at least five tabs 2064, 3064, depending on the configuration of the pin guides 2000, 3000 and the scapula. In another embodiment, tabs are not present owing to high precision and conformity of the patient-specific face 2016, 3016 to the bony surface.

Figure 43:
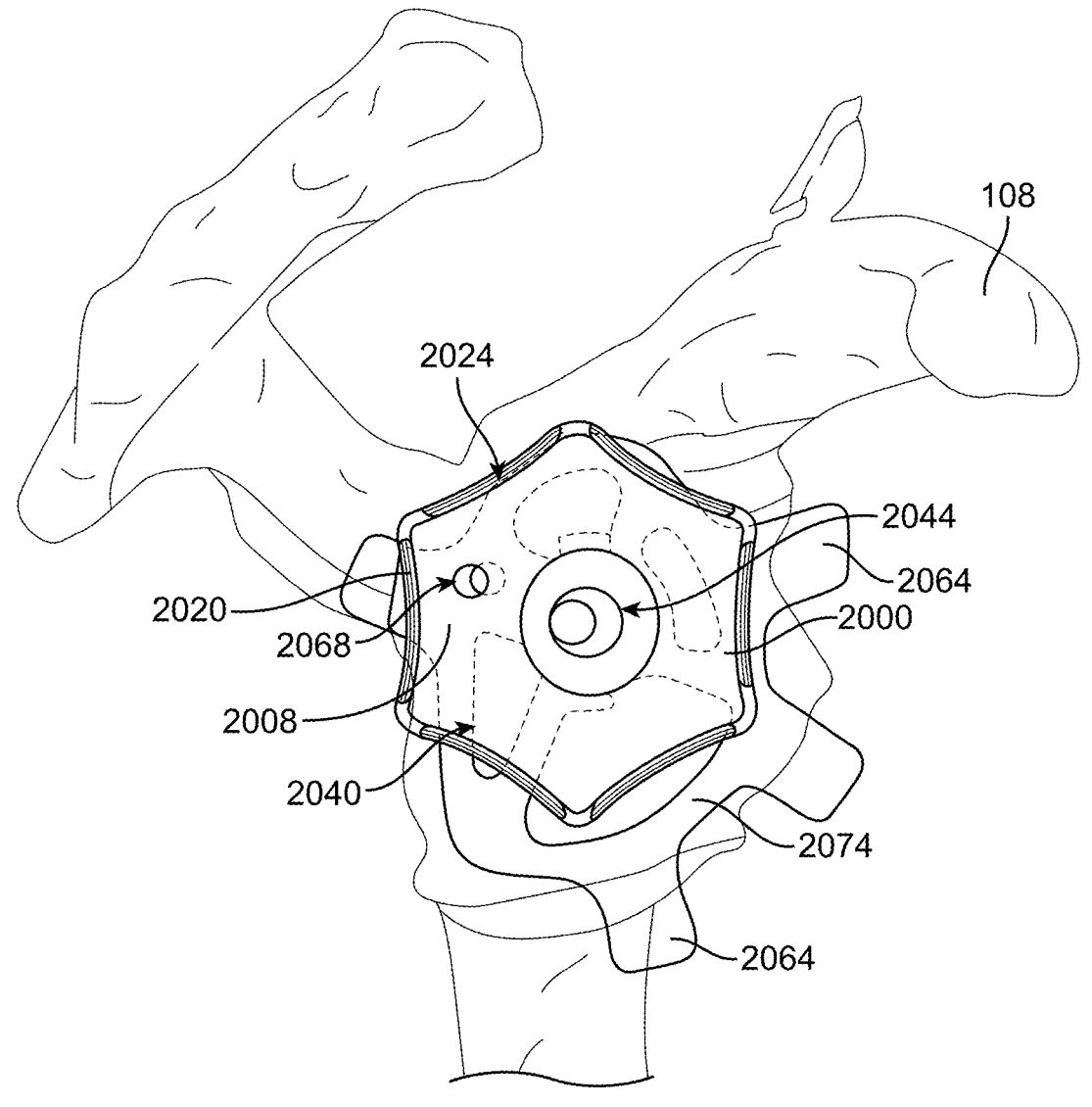
FIG. 43 is a back view of an exemplary pin guide interacting with patient anatomy, according to at least one embodiment.
Figure 44:
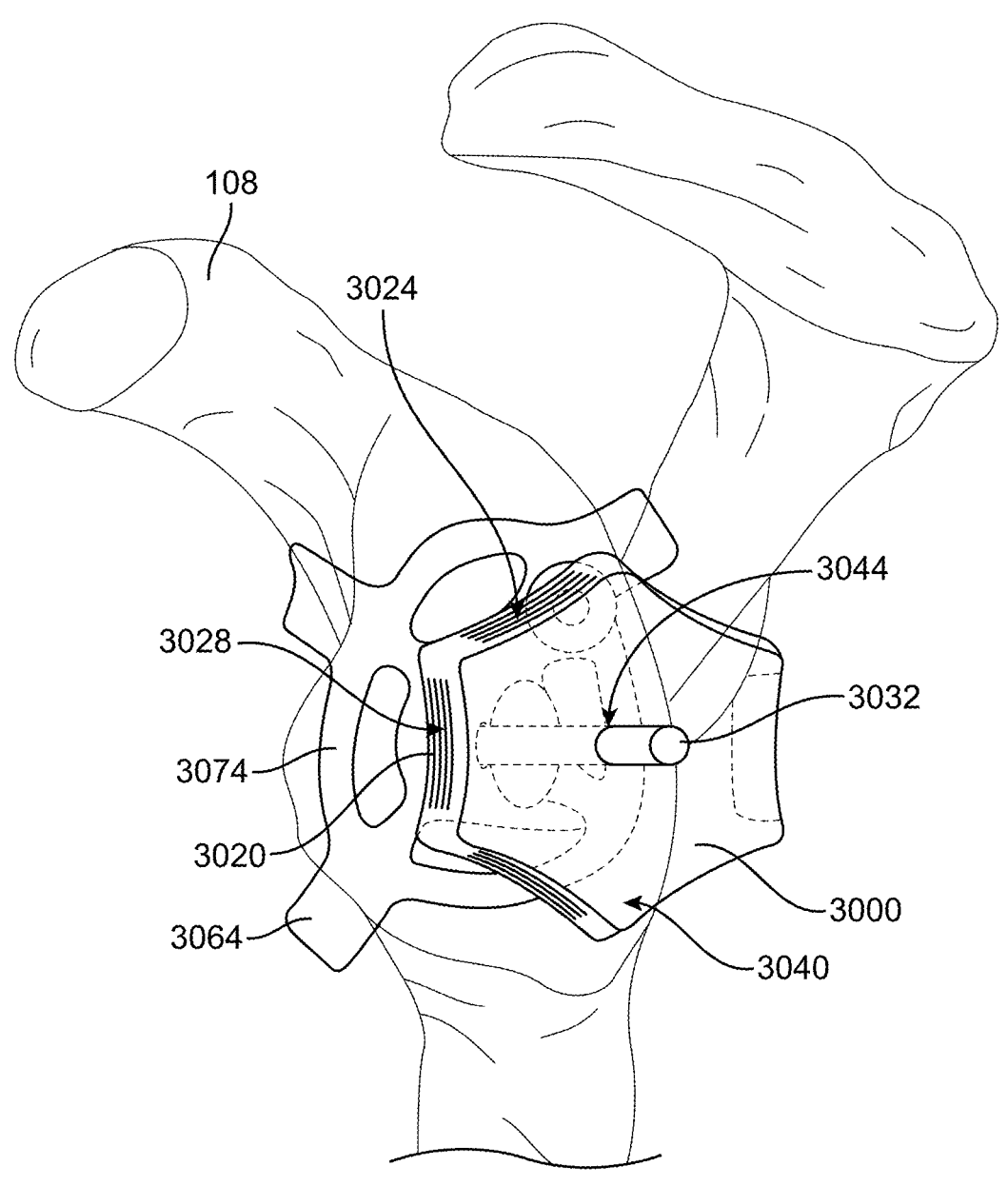
FIG. 44 is a back view of an exemplary pin guide interacting with patient anatomy, according to at least one embodiment.

FIGS. 43 and 44 display the attachment points of the tabs 2064, 3064 on the scapula when the pin guide 2000, 3000 is being used by the surgeon to facilitate insertion of the central pin 2032, 3032. The location of each tab of the tabs 2064, 3064 may be unique depending on the optimal attachment points on the scapula. In one embodiment, for example, the tabs 2064, 3064 are concentrated to one side, as shown in FIG. 43. In another embodiment, the tabs 2064, 3064 are spread apart, as shown in FIG. 44.

Consistent with the variable angulation of the baseplate post, the central pin 2032, 3032 may be inserted into the pin guide 2000, 3000 and subsequently the bony surface 2004, 3004 in a direction non-perpendicular to the sagittal plane (not shown). As such, angulation of the shaft 2012, 3012 of the pin guides 2000, 3000 with respect to the patient-specific face 2016, 3016 may be any number between 0 and 360 degrees. For example, in some embodiments, the angulation of the shaft 2012, 3012 can be between 45 and 65 degrees. In other embodiments, the angulation of the shaft 2012, 3012 can be between 115 and 135 degrees.

In one embodiment, the pin guide 2000 can be directed towards the bony surface 2004 at a substantially perpendicular angle to the sagittal plane such that tissue is not easily visible behind the handle 2008 of the pin guide 2000, as in FIG. 43. In another embodiment, the pin guide 3000 can be directed towards the bony surface 3004 at a substantially non-perpendicular angle to the sagittal plane such that tissue is easily visible through windows 3060 without obstruction by the handle 3008 of the pin guide 3000, as in FIG. 44.

Figure 45:
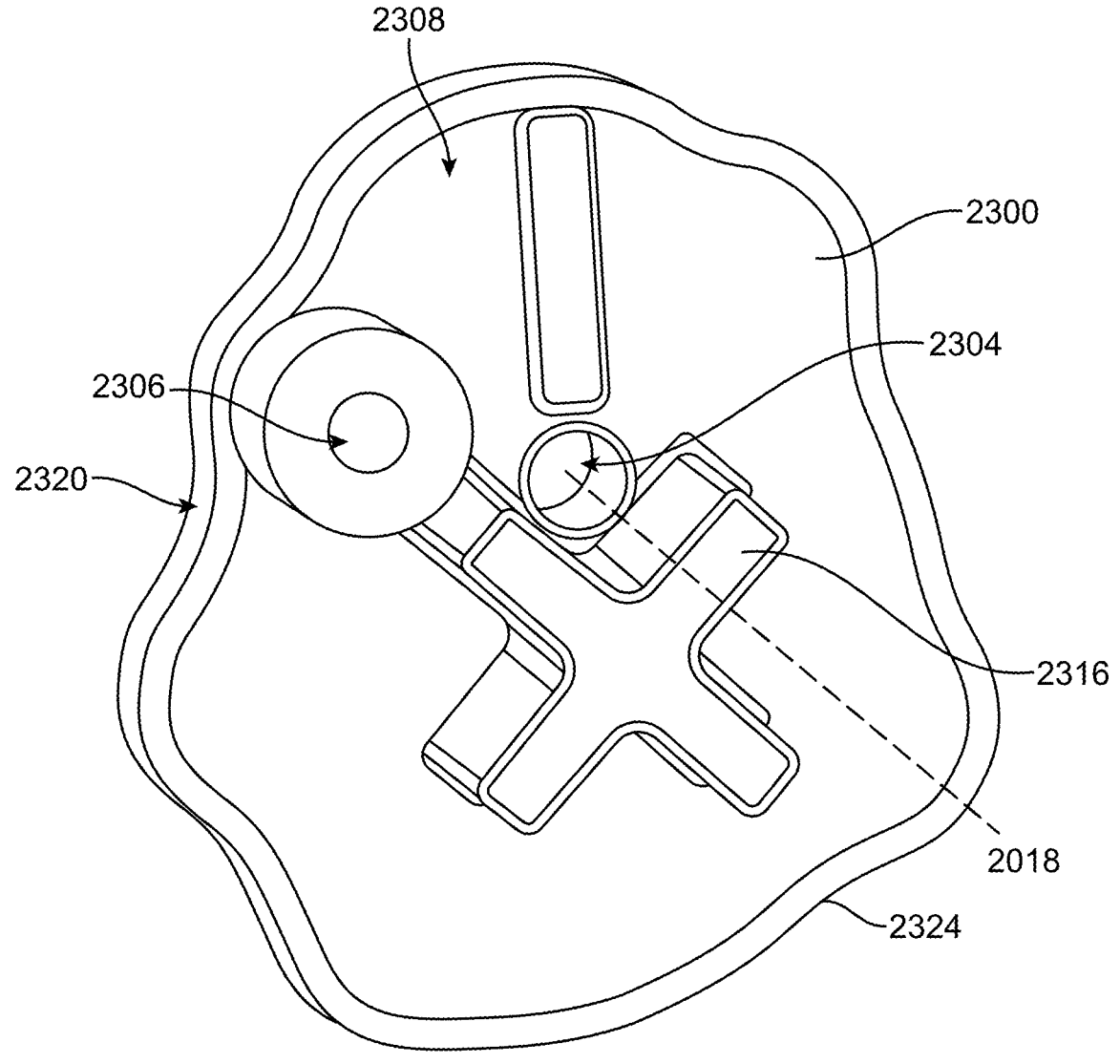
FIG. 45 is a perspective view of an exemplary baseplate trial, according to at least one embodiment.
Figure 46:
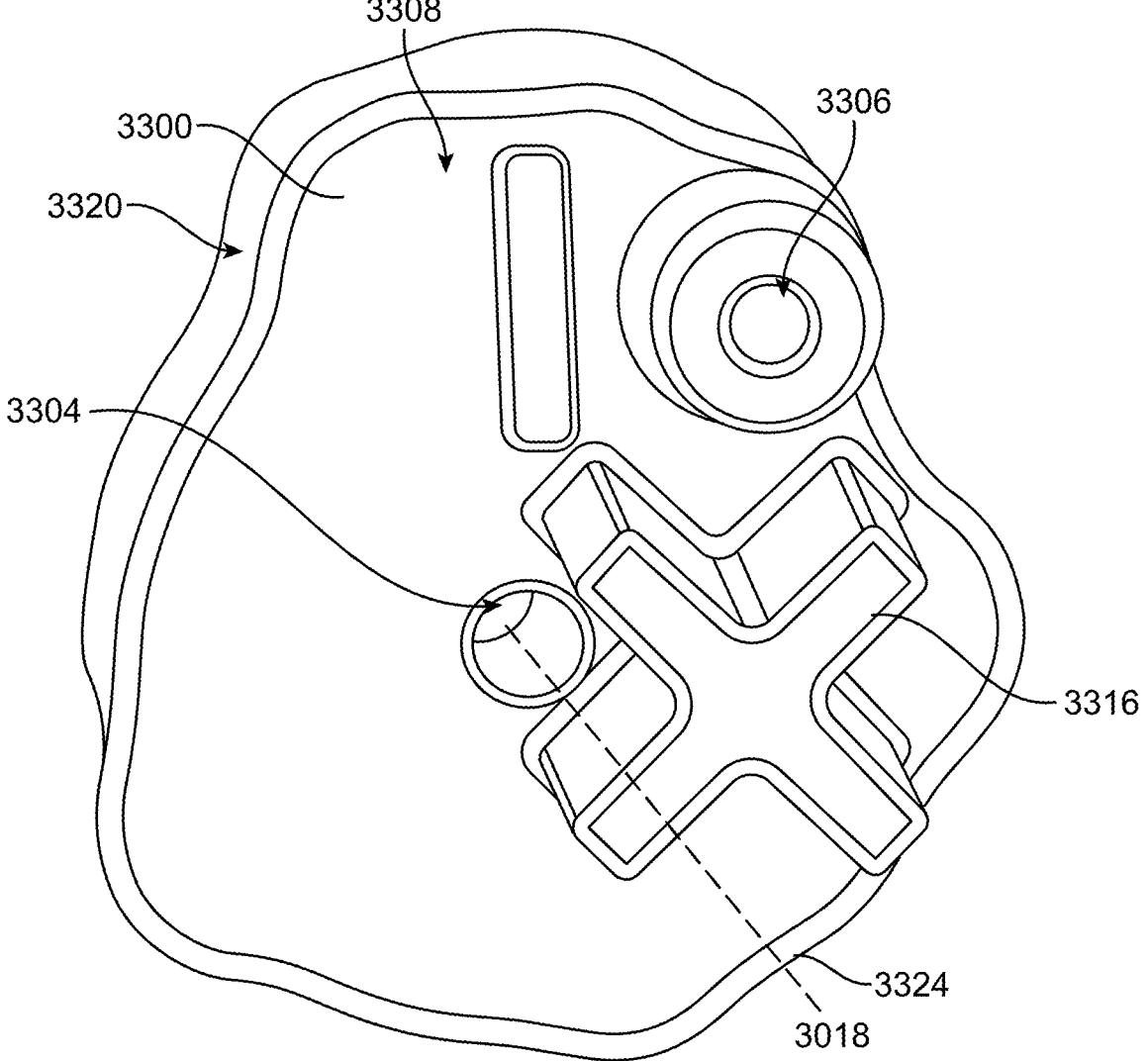
FIG. 46 is a perspective view of an exemplary baseplate trial, according to at least one embodiment.

Referring now to FIGS. 45 and 46, an alternative embodiment of the baseplate trial 2300, 3300 may include a modified location and orientation of the projection 2316, 3316 compared to the location and orientation of the projection 1316 on the baseplate trial 1300. The projections 2316, 3316 may be placed on the baseplate trial 2300, 3300 to optimize convenience and ergonomics for the surgeon. For example, the projection 2316, 3316 may be located above, below, or on either side of the central pin aperture 2304, 3304. In one embodiment, more than one projection 2316, 3316 is present to facilitate grip of the baseplate trial 1300 during use. In one such embodiment, the numerous projections are of varying shapes and sizes. In another embodiment, no projection is present on the front surface 2308, 3308 of the baseplate trial 2300, 3300.

Furthermore, in various embodiments, the outer perimeter 2324, 3324 of the baseplate trial 2300, 3300 is customized to adapt to the shape and size of the bony surface 2004, 3004 of the patient. As displayed in FIG. 45, in one embodiment, the outer perimeter 2324 may feature protrusions, recessions, and inflection points consistent with the outline of the bony surface 2004, 3004. For example, in one embodiment, a portion of the outer perimeter 2324, 3324 of the baseplate trial 2300, 3300 features a concave shape, which is configured to conform to a convexly shaped portion of the bony surface 2004, 3004. Non-limiting examples of other such configurations of the outer perimeter 2324, 3324 may include, but are not limited to, ridge-shaped portions of the outer perimeter 2324, 3324 configured for receipt by corresponding crease-shaped portions of the bony surface 2004, 3004; portions of the outer perimeter 2324, 3324 configured to be inserted into portions of the bony surface 2004, 3004; and other portions of various functions. In another embodiment displayed in FIG. 46, the outer perimeter 3324 may appear relatively smooth without substantial change in curvature.

Figure 47:
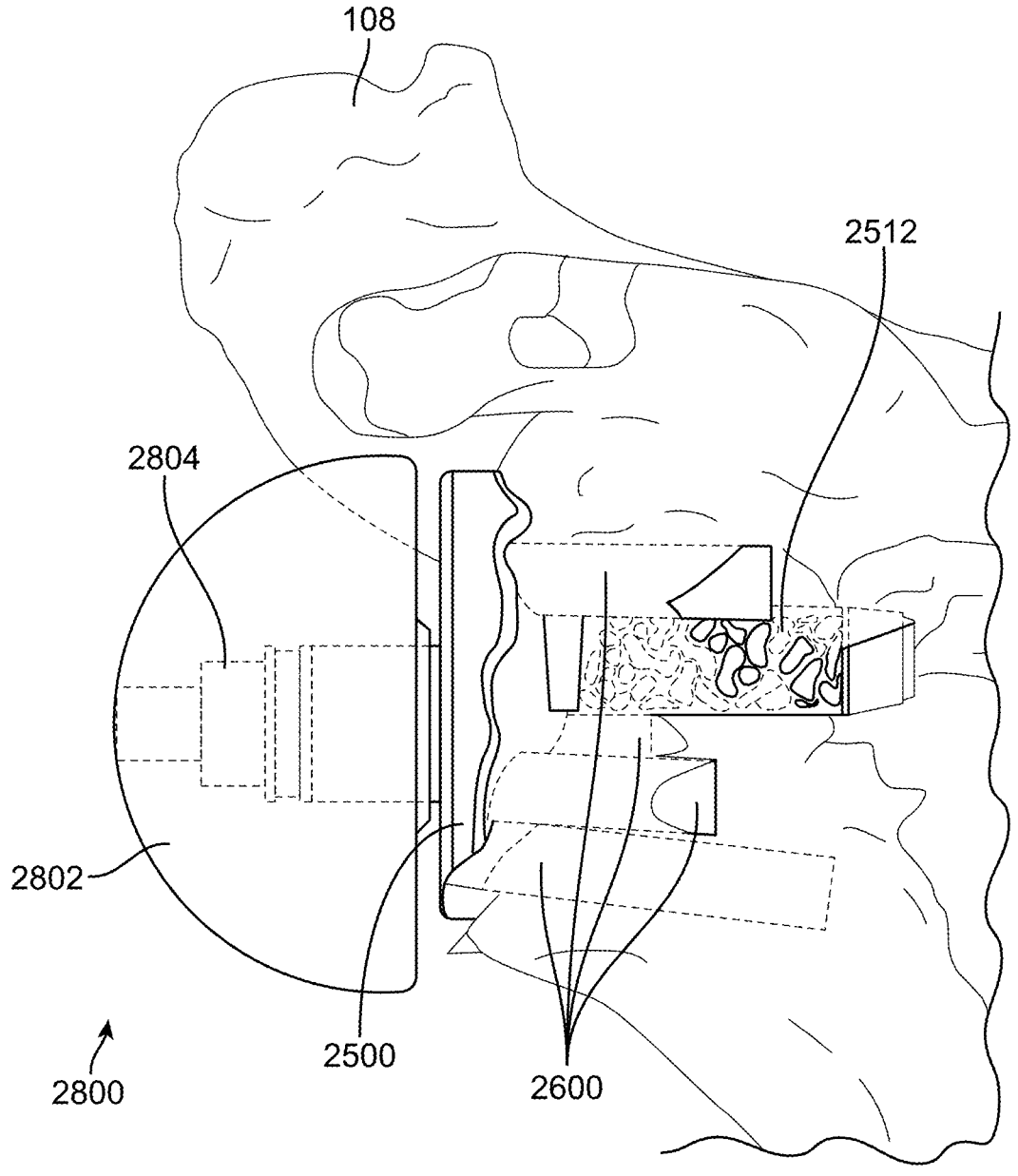
FIG. 47 is a side view of an exemplary glenoid system interacting with patient anatomy, according to at least one embodiment.
Figure 48:
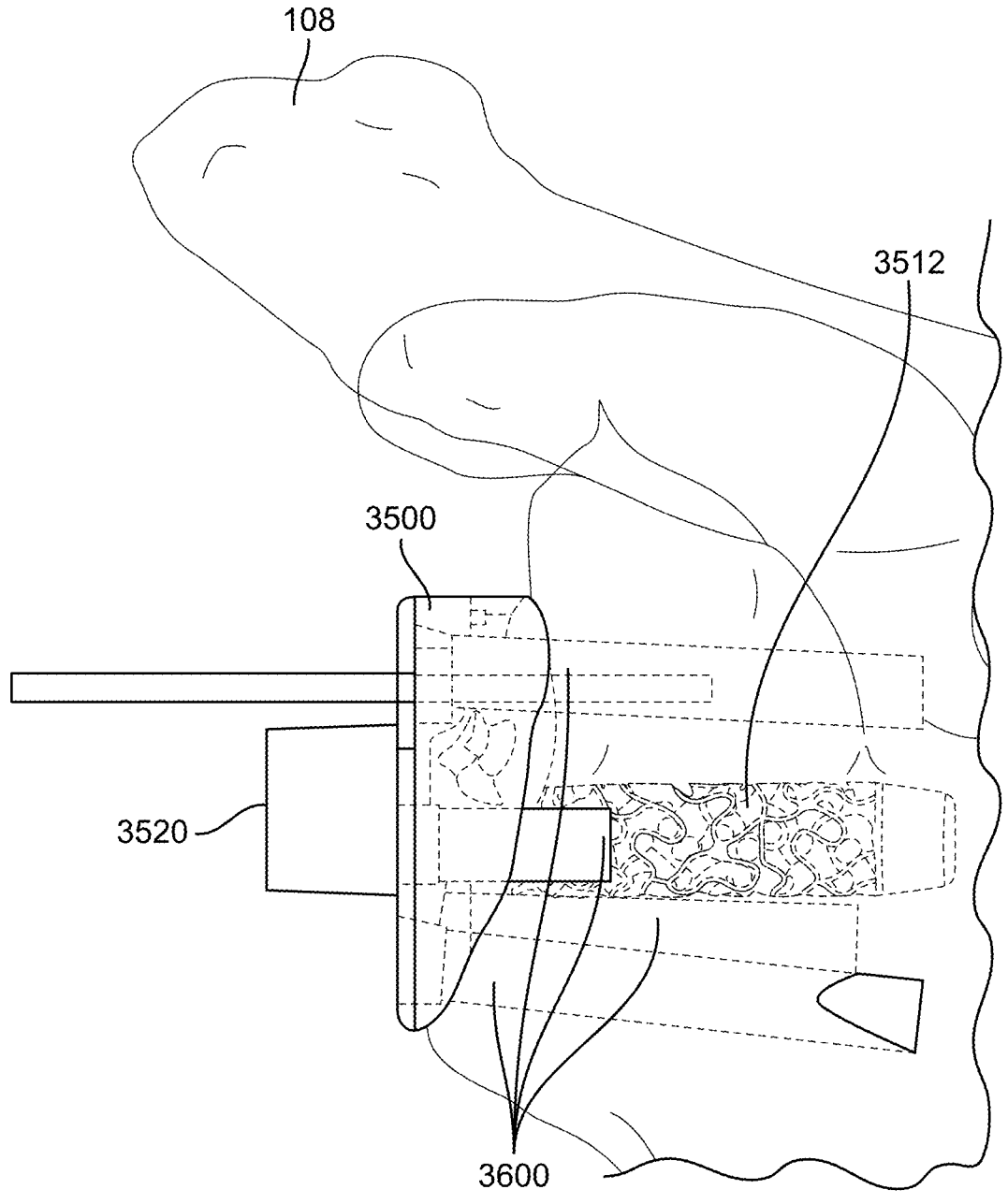
FIG. 48 is a side view of an exemplary glenoid system interacting with patient anatomy, according to at least one embodiment.

FIGS. 47 and 48 display a glenoid system for the exemplary second and third patient undergoing RSA. As previously described, the post 2512, 3512 may be inserted into the scapula at the bony surface 2004, 3004 askew to the sagittal plane (not shown). The peripheral fixation screws 2600, 3600 may be inserted into the scapula at the bony surface 2004, 3004 askew to the sagittal plane. The insertion angle of the peripheral fixation screws 2600, 3600 may additionally in one embodiment be substantially non-parallel to the post 2512, 3512. In one embodiment, the peripheral fixation screws 2600, 3600 are of various sizes and insertion distances (e.g., screw length) to optimize the fixation of the baseplate 2500, 3500. For example, the insertion distance of one or more of the peripheral fixation screws 2600, 3600 may be between 1 and 20 mm, or between 2.5 and 17.5 mm, or between 5 and 15 mm, or between 7.5 and 12.5 mm, or between 9 and 11 mm in any direction. In one embodiment, one or more of the peripheral fixation screws 2600, 3600 is inserted 10.75 mm into the bony surface 2004, 3004.

The taper 2520 may affix the glenosphere 2800 to the baseplate 2500 to provide full articulation of the patient's shoulder. A central axis of the glenosphere 2800 and the taper 2520 need not be parallel with the post 2512 nor the central pin axis (not shown). The trajectory of the peripheral fixation screws 2600, 3600, the post 2512, 3512, the taper 2520, and the central pin axis may thus all, in one embodiment, be substantially non-parallel to one another in accordance with the level of correction for the patient. In another embodiment, the trajectories of the peripheral fixation screws 2600, 3600, the post 2512, 3512, the taper 2520, and the central pin axis are or are almost parallel.

Further, the central axis of the glenosphere 2800 and the taper 2520 may not be colinear with a central axis of the post 2512. The post 2512, 3512 and the taper 3520 may thereby be positioned on the baseplate 2500, 3500 independent of one another. In one embodiment, the taper 2520, 3520 and the post 2512, 3512 are separated by a distance of between 0 and 20 mm, or between 3 and 18 mm, or between 5 and 15 mm, or between 7 and 13 mm, or between 9 and 11 mm. In one such embodiment, the taper 2520, 3520 and the post 2512, 3512 are offset by 10 mm. In one embodiment, the post 2512, 3512, the baseplate 2500, 3500, and the taper 3520 are modularly assembled prior to installation in the patient. In another embodiment, the post 2512, 3512, the baseplate 2500, 3500, and the taper 3520 are integrally formed prior to installation.

The post 2512, 3512 and side surfaces 2320, 3320 of the baseplates 2500, 3500 may feature porous surfaces 2508 (see FIG. 47) and/or smooth surfaces 3510 (see FIG. 48) in accordance with the patient-specific design of the baseplate 2500, 3500. In one embodiment, for example, the porous surfaces may comprise at least 0.1%, or at least 10%, or at least 20%, or at least 25%, or at least 50%, or at least 75%, or at least 90%, or 100% of the surfaces of the baseplate 2500, 3500. In another embodiment, there are no porous surfaces of the baseplate 2500, 3500. In another embodiment, for example, the smooth surfaces may comprise at least 0.1%, or at least 10%, or at least 20%, or at least 25%, or at least 50%, or at least 75%, or at least 90%, or 100% of the surfaces of the baseplate 2500, 3500. In yet another embodiment, there are no smooth regions of the baseplate 2500, 3500.

Figure 49:
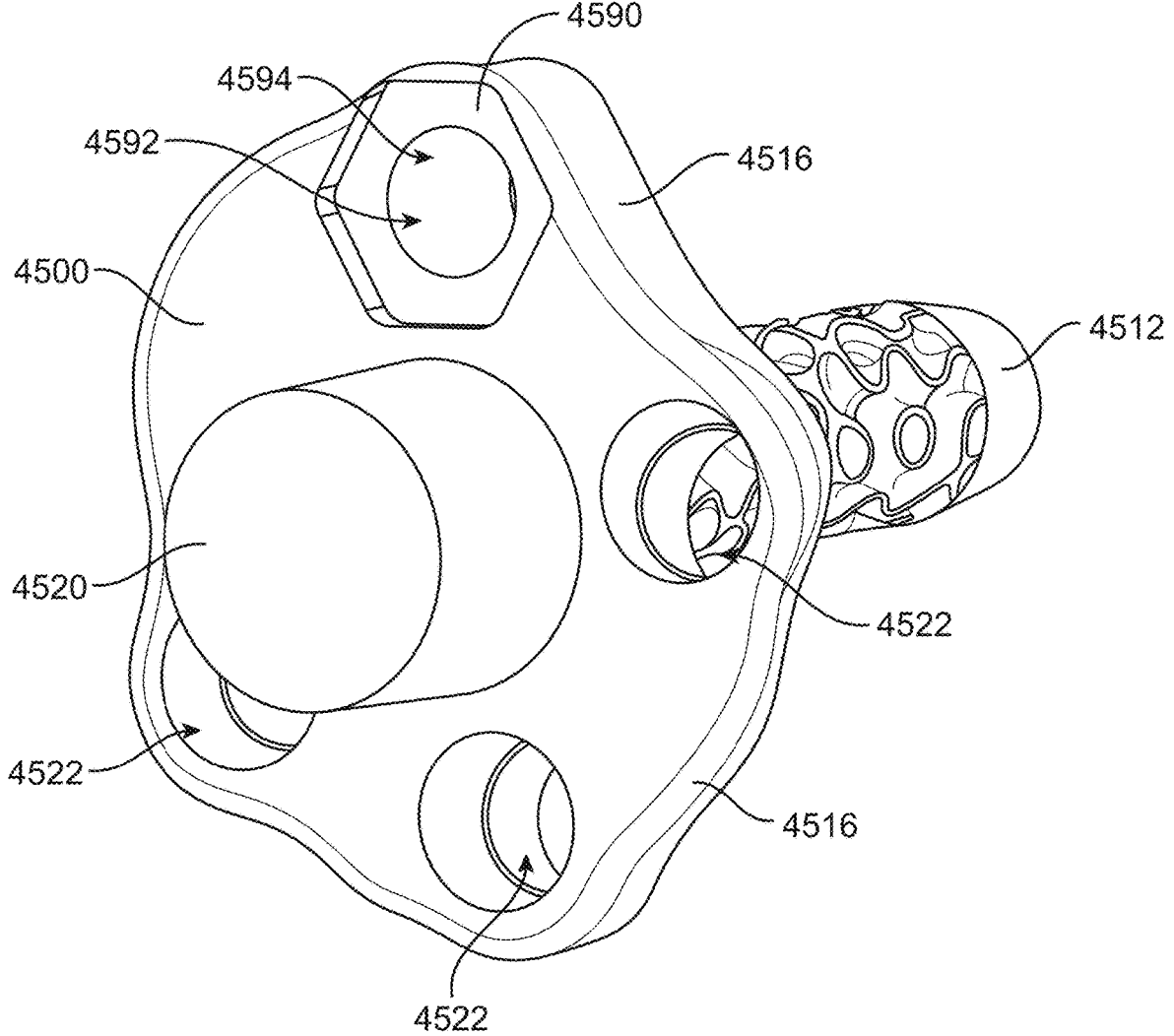
FIG. 49 is a first perspective view of an exemplary baseplate, according to at least one embodiment.
Figure 50:
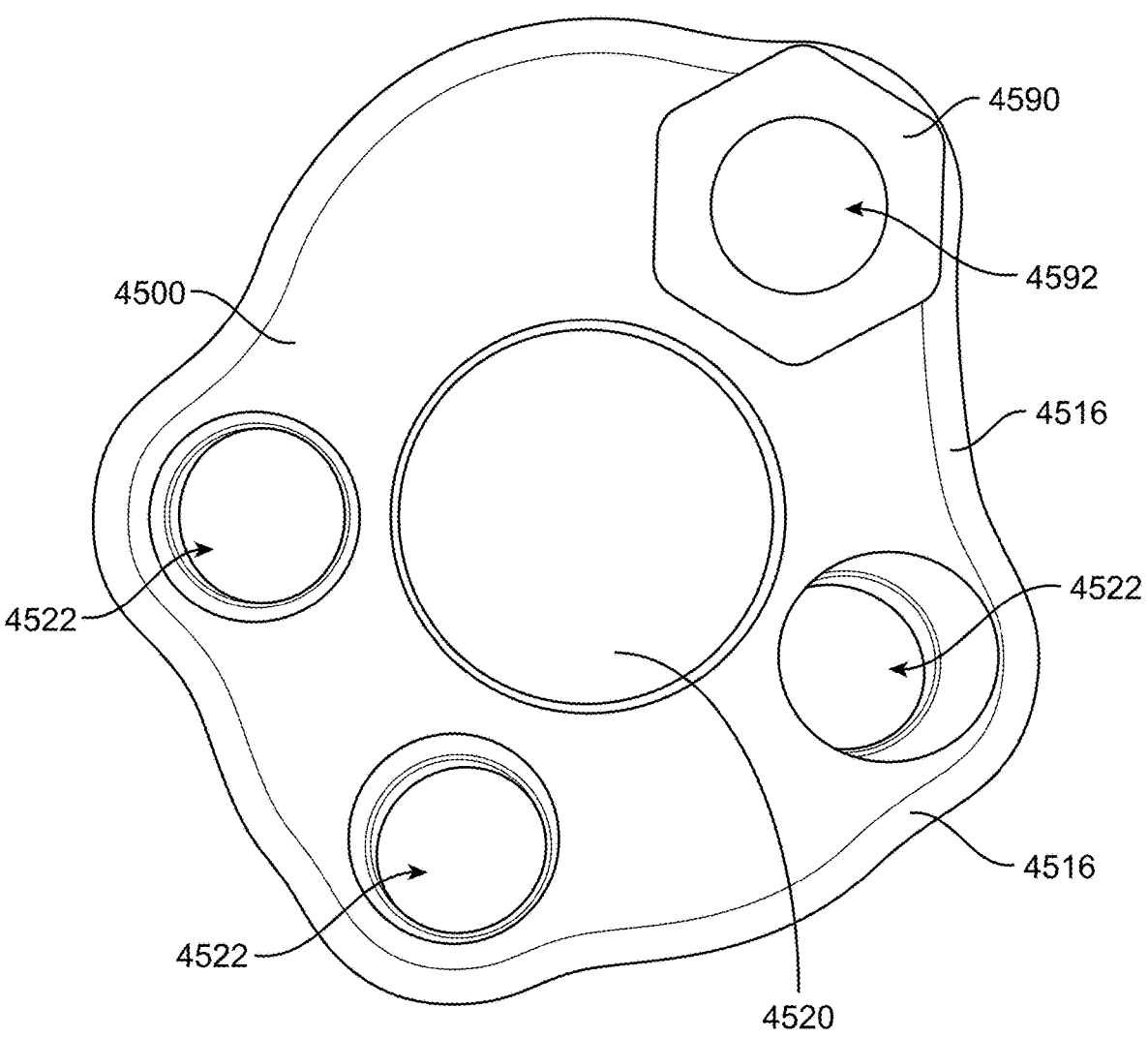
FIG. 50 is a back view of an exemplary baseplate, according to at least one embodiment.
Figure 51:
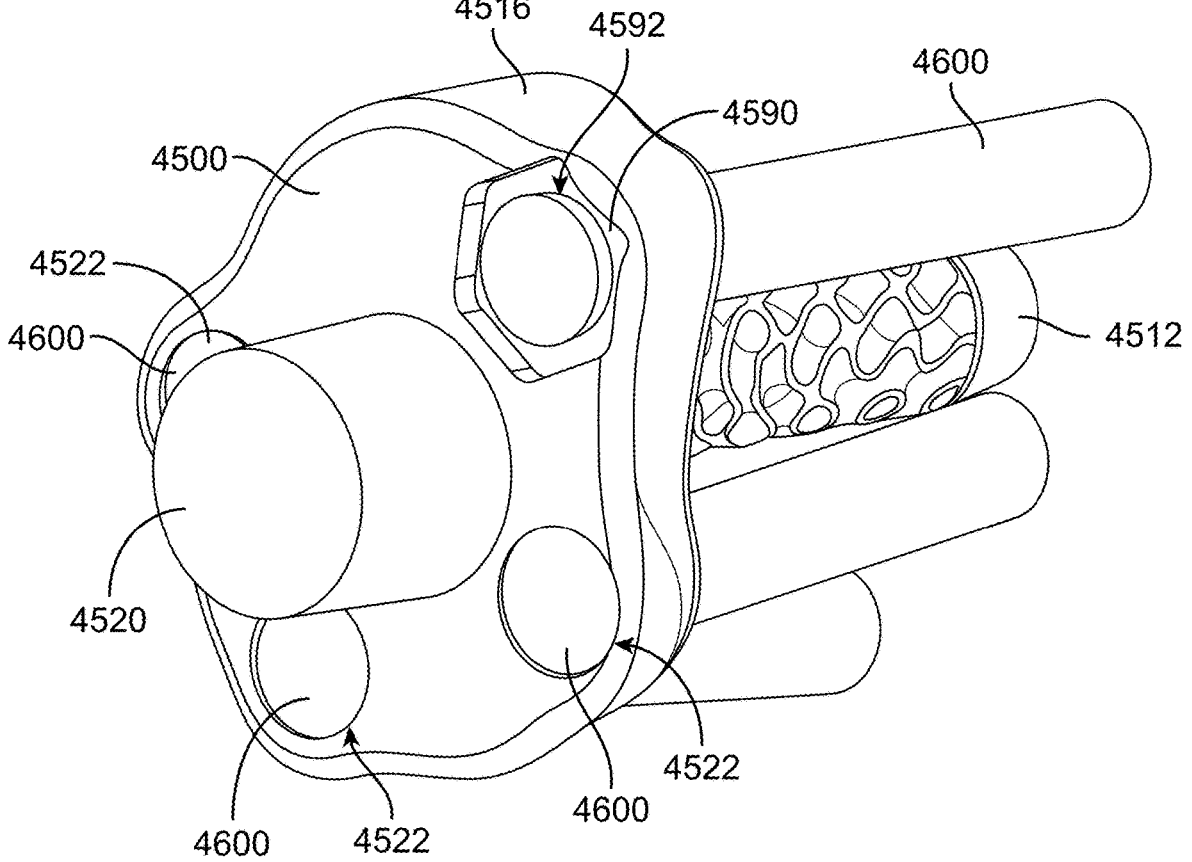
FIG. 51 is a first perspective view of an exemplary glenoid system, according to at least one embodiment.
Figure 52:
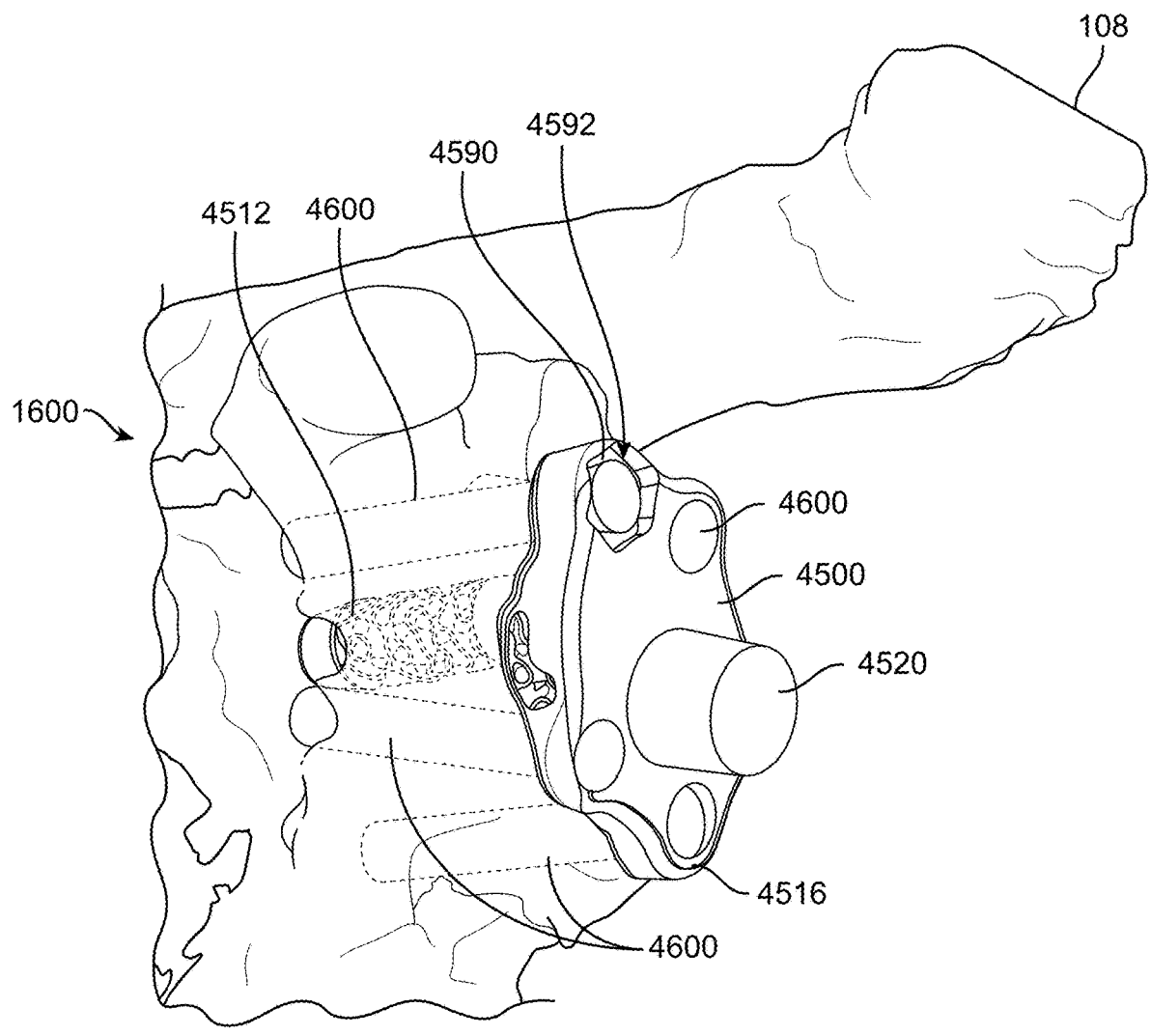
FIG. 52 is a perspective view of an exemplary glenoid system interacting with patient anatomy, according to at least one embodiment.

Referring now to FIG. 49, according to additional embodiments, a baseplate 4500 can comprise a central post 4512, a periphery 4516, a morse taper 4520, a series of peripheral fixation screw through-holes 4522, an anti-rotation element 4590, and a dual-purpose opening 4592 (see FIGS. 50-52). In various embodiments, the dual-purpose opening 4592 further comprises a series of internal threads 4594 configured to receive a peripheral fixation screw. The dual-purpose opening 4592 may be configured to receive both an anti-rotation pin (not depicted) and a peripheral fixation screw 4600. In an embodiment, the anti-rotation pin can extend through the dual-purpose opening 4592. The peripheral fixation screw 4600 may also be screwed into the dual-purpose opening 4592 (sometimes referred to herein as an "anti-rotation hole") after removal of the anti-rotation pin, serving as an addition affixation point of the baseplate 4500 to the bony surface.

In the exemplary embodiment depicted in FIGS. 51 and 52, the anti-rotation element 4590 is a generally hexagonal cutout (sometimes referred to herein as "hex-shaped") in the lateral surface of the baseplate 4500. In other embodiments, the anti-rotation element 4590 can be a square cutout, a rectangular cutout, a pentagonal cutout, an octagonal cutout, or some other polygonal cutout. In further embodiments, the anti-rotation element 4590 can be a series of holes in the lateral surface of the baseplate 4500 configured to receive a series of pins. As will be understood, the anti-rotation element 4590 may be any suitable mechanism for preventing rotation and should not be limited to those examples provided herein.

The dual-purpose opening 4592 may extend through the baseplate 4500 from the lateral surface to the medial surface. In the exemplary embodiment, the dual-purpose opening 4592 is arranged at the center of the anti-rotation element 4590. In other embodiments, the dual-purpose opening 4592 can be arranged off-center within the anti-rotation element 4590. In embodiments where the anti-rotation element 4590 comprises the series of holes, the series of holes may generally surround the dual-purpose opening 4592.

Figure 53:
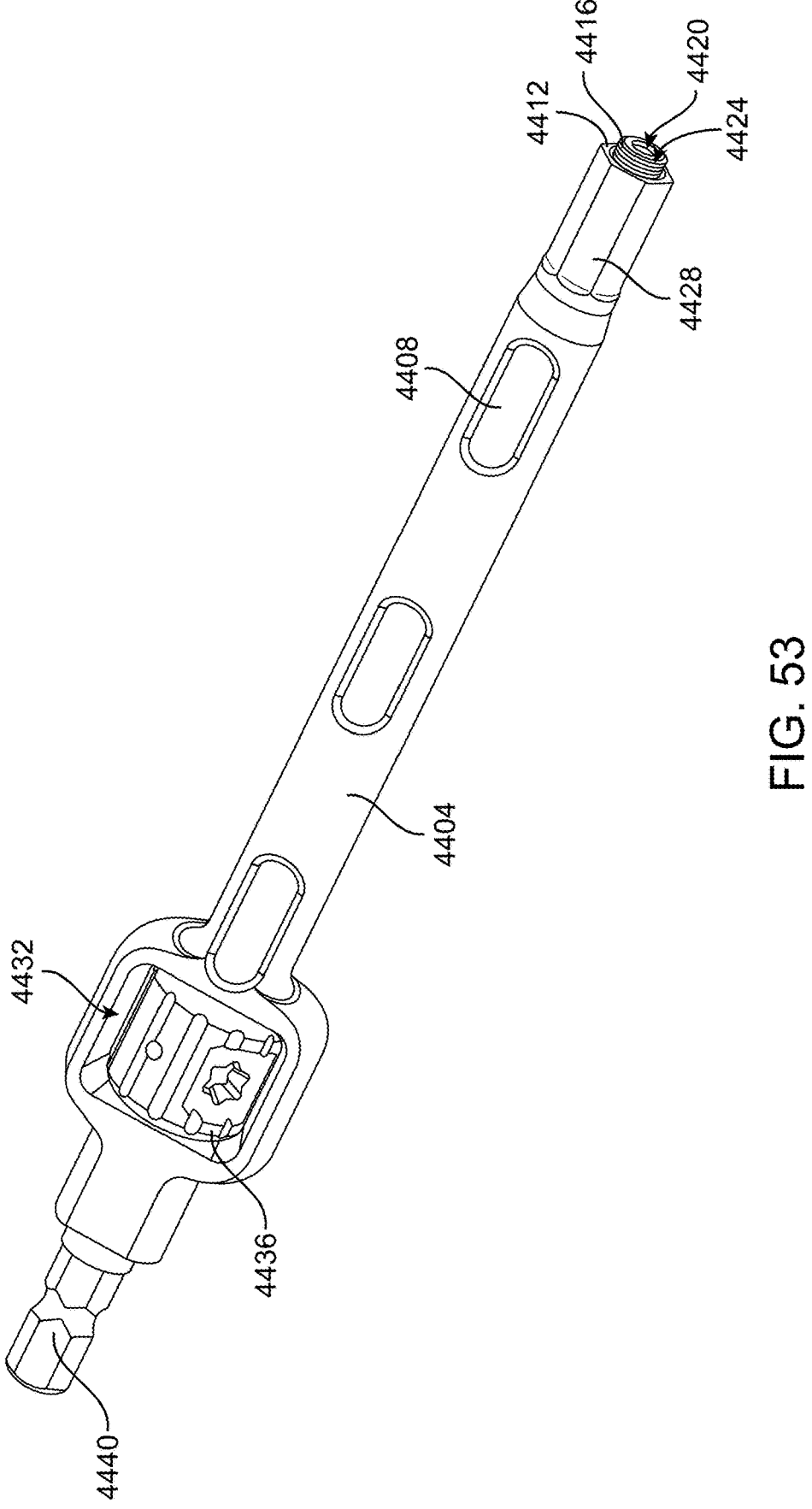
FIG. 53 is a perspective view of a cannulated inserter, according to at least one embodiment.

The anti-rotation element 4590 may be configured to mate with at least a portion of a cannulated inserter 4400 (sometimes referred to herein as an "inserter tool"), as depicted in FIG. 53. The cannulated inserter 4400 may comprise an external shaft 4404, an internal screw 4408, a proximal end 4412, a distal end 4440, and a rotary wheel 4436. In some embodiments, the cannulated inserter 4400 can further comprise a wheel housing 4432. In the embodiment shown, the external shaft 4404 may define an internal channel 4424, configured to house the internal screw 4408, such that the internal screw 4408 can rotate within the internal channel 4424 of the external shaft 4404. The internal screw 4408 defines a pin channel 4420, configured to receive an anti-rotation pin.

Figure 54:
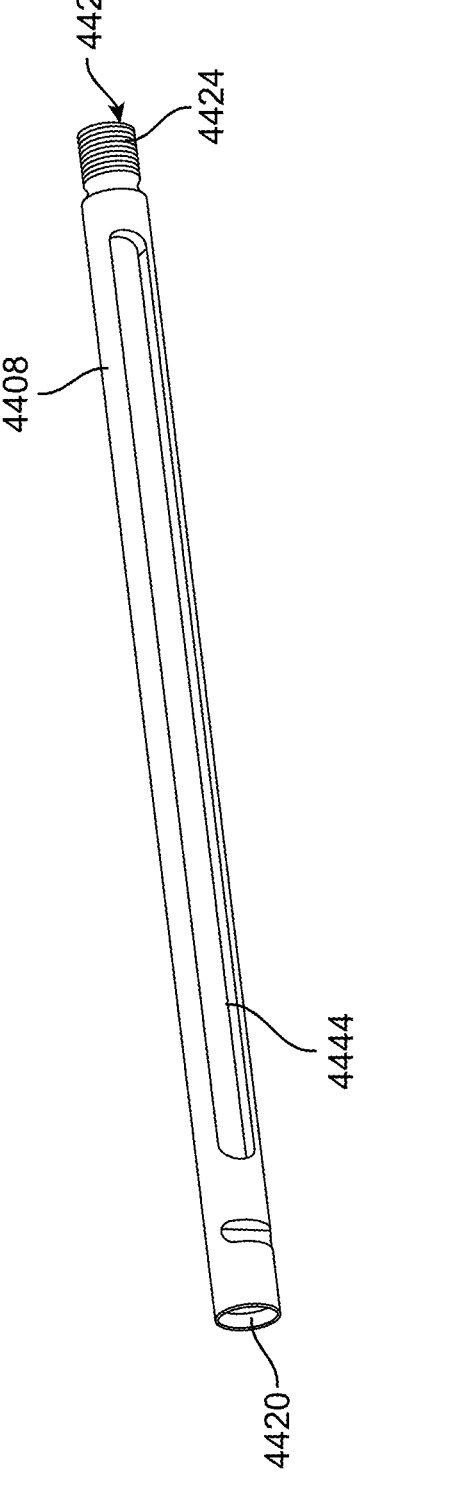
FIG. 54 is a perspective view of an internal screw of a cannulated inserter, according to at least one embodiment.

In the exemplary embodiment depicted in FIGS. 53 and 54, the proximal end 4412 comprises a hexagonal anti-rotation profile 4428 configured to fit within (or selectively engage with) the hexagonal anti-rotation element 4590 of the baseplate 4500, described supra. In various embodiments, when the anti-rotation profile 4428 is fit within the anti-rotation element 4590, the external shaft 4404 is prevented from rotating. In embodiments where the anti-rotation element 4590 is a different configuration (e.g., not hexagonal), the anti-rotation profile 4428 can be configured accordingly. For example, in an embodiment where the anti-rotation element 4590 is a square cutout, the anti-rotation profile 4428 of the proximal end 4412 will similarly be square. In another embodiment where the anti-rotation element 4590 is an octagonal cutout, the anti-rotation profile 4428 of the proximal end 4412 will similarly be octagonal. In yet another embodiment, where the anti-rotation element 4590 is a series of holes in the lateral face of the baseplate 4500, the proximal end 4412 can comprise a series of pins (not depicted) configured to fit within the series of holes. In such an embodiment, the anti-rotation profile 4428 can be any desired shape, such a circular, square, hexagonal, octagonal, or any other polygonal shape, because the series of pins prevent rotation of the external shaft 4404.

The internal screw 4408 can extend through the external shaft 4404 such that an attachment end 4416 can emerge from the proximal end 4412 of the cannulated inserter 4400. The attachment end 4416 of the internal screw 4408 can comprise a series of threads configured to be screwed into the internal threads 4594 of the dual-purpose opening 4592 of the baseplate 4500. It is contemplated that other means of temporary attachment can be utilized to secure the attachment end 4416 to the dual-purpose opening 4592, such as press fit, snap fit, a series of tabs, or other mechanical attachments. In one non-limiting example, the proximal end 4412 may be externally threaded and the dual-purpose opening 4592 may include internal threading, such that selective engagement of the proximal end 4412 and the dual-purpose opening 4592 reversibly threads, locks, or otherwise mates, the cannulated inserter 4400 with the baseplate 4500. Thus, the attachment end 4416 can comprise any mechanical attachment that temporarily secures the cannulated inserter 4400 to the baseplate 4500 and the anti-rotation pin.

In an exemplary use, the cannulated inserter 4400 can stabilize the baseplate during installation, and in combination with a post or another feature, can prevent rotation of the baseplate while one or more peripheral fixation screws are installed. First, in one embodiment, the anti-rotation profile 4428 can be fit within the anti-rotation element 4590 cutout of the baseplate 4500. In this configuration, the threads of the internal screw 4408 of the cannulated inserter 4400 are in a position to be screwed into the internal threads 4594 of the dual-purpose opening 4592. The rotary wheel 4436 can be turned in a first or a second direction to rotate the internal screw 4408, screwing the threads of the internal channel 4424 of the cannulated inserter 4400 into the internal threads 4594 of the dual-purpose opening 4592. The anti-rotation element 4590 may prevent the external shaft 4404 of the cannulated inserter 4400 from rotating, and the threads of the internal channel 4424 can mate with the dual-purpose opening 4592 to reversibly lock the cannulated inserter 4400 with the baseplate.

The combination of the cannulated inserter 4400 and the baseplate can be placed over an installed anti-rotation pin (not depicted) such that the anti-rotation pin is received into the pin channel 4420. The cannulated inserter 4400 is thus secured to the baseplate 4500 for the duration of the insertion of any peripheral fixation screws 4600 into the peripheral fixation screw through-holes 4522.

After one or more peripheral fixation screws 4600 have be inserted through the peripheral fixation screw through-holes 4522 to secure the baseplate 4500 to the surgical site, the cannulated inserter 4400 can then be removed. The rotary wheel 4436 can be turned to unscrew the internal screw 4408 from the dual-purpose opening 4592. Once the internal screw 4408 is removed from the dual-purpose opening 4592, the cannulated inserter 4400 can be removed from the surgical site. The anti-rotation pin can then be removed from surgical site according to the systems and methods described supra (the anti-rotation pin can be removed before or after the cannulated inserter 4400 is detached from the baseplate). In some embodiments, a peripheral fixation screw 4600 can be screwed into the dual-purpose opening 4592 to further secure the baseplate 4500 to the surgical site.

Any one or more of the aforementioned tools and/or implant systems may be assembled or collected prior to surgery for distribution to a surgeon performing the RSA procedure. For example, an RSA kit may include a tray or the like, with at least one or more of the exemplary pin guide, the central pin, the anti-rotation pin, the baseplate trial, the screw guide, the baseplate, the peripheral fixation screws, the glenosphere and/or components of the humeral stem system including but not limited to the humeral stem, the spacer tray, and the liner. In one embodiment, such a kit also includes three-dimensional renditions of patient anatomy (such as the scapula and/or humerus) to assist in simulation of the RSA procedure by the surgeon. Any one or more of the aforementioned components may be customized prior to distribution to the surgeon or may be further modified upon use in the procedure and based on interaction with patient anatomy. As will be understood, components in a kit discussed herein may be sterilized or unsterilized or a kit may include a combination of sterilized and unsterilized components.

In one embodiment, the kit includes additional components representative of a modular design of components of the implant assembly. For example, in one embodiment, the kit may include the taper and the patient-specific post as separate items, which may be press-fit on or otherwise fixed to the baseplate prior to or during surgery.

Referring now to FIG. 55, an exemplary, non-limiting, method 5000 for performing an RSA procedure using the tools in the aforementioned exemplary kit is shown. The method 5000 may include a step 5002 of placing a patient-specific face of a pin guide on a bony surface, wherein tabs of the pin guide contact the bony surface of the patient. In one embodiment, the tabs contact the bony surface at one or more positions to ensure the stability and precision of the pin guide on the bony surface. In another embodiment, the use of tabs to ensure proper placement is not needed.

One of ordinary skill in the art would recognize that in one embodiment, the bony surface may optionally be modified by the surgeon in any suitable way, such as via removal or resection of soft tissue, cartilage, or bone, in response to an ill fit of the pins. In another embodiment, the bony surface need not be modified after placement of the pin guide. In one such embodiment, modification of the bony surface prior to pin guide placement sufficiently prepares the surface for the RSA procedure. In at least one embodiment, placement of the pin guide and resection of the bony surface may be performed iteratively until a proper fit of the pin guide is achieved.

The method 5000 may then include a step 5004 of inserting a central pin and an anti-rotation pin through apertures of the pin guide and installing the pins in the bony surface. In at least one embodiment, the central pin and the anti-rotation pin provide markers on the bony surface for future steps in the procedure. Installation of the central pin and the anti-rotation may produce orifices in the bony surface that remain open once the pins are later removed.

The method 5000 may further include a step 5006 of placing a patient-specific surface of a baseplate trial on the bony surface by sliding designated apertures in the baseplate trial over the central pin and the anti-rotation pin. One of ordinary skill in the art would recognize that in one embodiment, the bony surface may optionally be modified by the surgeon in any suitable way, such as via removal or resection of soft tissue, cartilage, or bone, in response to an ill fit of the baseplate trial. In at least one embodiment, placement of the baseplate trial and modification of the bony surface may be performed iteratively until a proper fit of the baseplate trial is achieved.

The method 5000 may next include a step 5008 of drilling into the bony surface at the location of the central pin aperture (e.g., after removing the baseplate trial). In one embodiment, the orifice created by the insertion of the central pin into the bony surface does not remove sufficient tissue for the later installation of the post, requiring a drill that is larger in diameter than a diameter of the central pin. In one such embodiment, the diameter of the drill is substantially the same as a diameter of the later-installed baseplate post. In another such embodiment, the diameter of the drill is slightly larger or smaller in diameter than the diameter of the later-installed baseplate post.

The method 5000 may then include a step 5010 of installing a patient-specific baseplate containing a patient-specific post into the bony surface by sliding a designated aperture in the baseplate over the anti-rotation pin and inserting the patient-specific post into the bone or bones of the patient.

The method 5000 may additionally include a step 5012 of installing peripheral fixation screws through apertures in the baseplate to ensure fixation of the baseplate to the bony surface. A length, diameter, and quantity of the peripheral fixation screws may be customized per patient.

In some embodiments, the surgical plan, system, or kit may further include a representative guide 6200, as depicted in FIGS. 56 and 57. The medical team may reference the representative guide 6200 throughout the course of the installation of the patient-specific baseplate. The representative guide 6200 may be configured to support the medical team in visualizing the angle and depth of each of the peripheral screws to be installed in said patient-specific baseplate. For example, a surgeon or surgical robot may use the information in the representative guide 6200 to visualize an angle of a drill and adjust an arm to such an angle to drill according to the representative guide. As will be understood, in at least one embodiment, the representative guide 6200 may be sterilized and may include any other information.

In at least one embodiment, the representative guide 6000 comprises a representative scapula 6202, a representative baseplate 6212, representative peripheral screws 6204, depth indicators 6216, and a representative central post or central post aperture 6220. The representative scapula 6202 may be a model of the patient's scapula (e.g., based on CT scans or other patient-specific information or imaging). The representative baseplate 6212, the representative peripheral screws 6204, and the representative central post or central post aperture 6220 may be modeled after the patient-specific device(s) to be installed. The representative guide 6200 can be integrally formed, or comprise multiple components configured to fit together.

In at least one embodiment, the depth indicators 6216 represent the depth of an aperture for a particular peripheral screw in the patient-specific surgical plan, measured in millimeters (although any measurement may be used). In the exemplary embodiment, the depth indicators 6216 indicate the apertures for each of the representative peripheral screws 6204 are 18 millimeters, 30 millimeters, 42 millimeters, and 34 millimeters, respectively. In other embodiments, the depth indicators 6216 may indicate other aperture depths, as may be determined by the patient-specific surgical plan. Further, there may be more than four depth indicators 6216 because the patient specific surgical plan may require more than four peripheral screws 6204. In other embodiments, there may be fewer than four depth indicators 6216 because the patient specific surgical plan may require less than four peripheral screws 6204.

The representative peripheral screws 6204 represent the peripheral screws to be installed for the patient-specific baseplate. The exemplary embodiment depicts four representative peripheral screws 6204. In other embodiments, there may be more than four representative peripheral screws 6204 because the patient-specific plan may require more than four peripheral screws 6204. In yet further embodiments, there may be fewer than four representative peripheral screws 6204, because the patient-specific plan may require less than four peripheral screws.

The representative guide 6200 may be manufactured by 3D printing or similar processes. In the exemplary embodiment depicted in FIG. 57, the representative peripheral screws 6204 and the depth indicators 6216 may comprise or consist essentially of an opaque material and/or colored material, while the remaining components of the representative guide 6200 may comprise a translucent or transparent material. Accordingly, the angle and depth of a peripheral screw shaft 6208 within the representative scapula 6202 may advantageously be observed by a medical team prior to implantation in the true patient anatomy.

The patient-specific post may be coupled to the patient-specific baseplate prior to surgery, may be integrally formed with the baseplate, or may be coupled upon insertion into the bony surface with the patient-specific baseplate. In one embodiment, the patient-specific post and the patient-specific baseplate feature regions of varying porosity to facilitate bone growth when installed. The patient-specific post may be inserted into the bony surface at any angle with respect to the bony surface, a surface of the baseplate interacting with the bony surface, and a Friedman's Line projecting away from the bony surface. The patient-specific post may further be located on any portion of a surface of the patient-specific baseplate irrespective of the location of a taper coupled to the patient-specific baseplate.

In some embodiments, a surgical plan may include more than one anti-rotation pin. This may be desirable in surgical plans involving complex geometries on the exposed surface of the modified glenoid cavity or for general added stability of a baseplate or other components. In such embodiments, the additional anti-rotation pins can be inserted into the surgery site with a screw guide, as described supra. Various system/kit components may thus include additional guide pin holes to accommodate the additional anti-rotation pins. In at least one embodiment, during the installation of the baseplate, the baseplate is arranged so that each of the additional anti-rotations pins is inserted through an additional guide pin hole. At various points throughout the installation of the baseplate, one or more of the anti-rotation pins may be removed, rotated, and/or replaced according to the details of the surgical plan.

Some embodiments discussed herein relate to use of a central post on a baseplate. However, it should be understood that the components, devices, systems, and kits herein may utilize a central fixation member other than a post or a type of post not explicitly shown and described herein. For example, in one embodiment, a baseplate can comprise a central screw opening instead of a post, where the central screw opening is configured to receive a central screw. In such an embodiment, a patient's glenoid cavity may be additionally modified (or modified in a way that is different than for a central post as described herein) to receive a central screw, such as through additional removal of tissue and/or bone, after which an anti-rotation pin (or pins) can be inserted as described supra. Once the modified glenoid cavity is prepared to receive the baseplate and the central screw, the base plate can be guided over the installed anti-rotation pin until the baseplate is press fit against the surface of the modified glenoid cavity. Then, the central screw can be inserted into through the central screw opening and into the glenoid cavity according to any of the methods discussed herein.

In some surgical plans, peripheral fixation screws may not be suitable to affix a baseplate to the modified glenoid cavity. In these scenarios, the baseplate can comprise one or a series of peripheral fixation spikes or broaches arranged in much the same way as the peripheral fixation screws would be in surgical plans where peripheral fixation screws could be utilized. The peripheral fixation spikes can vary in length according to the surgical plan. For example, in some surgical plans, the peripheral spikes may be 3 centimeters in long. In other surgical plans, the peripheral spikes may be 6 centimeters long. The peripheral spikes can comprise the same material as the baseplate, be integrally formed, or be made from a different material. It is contemplated that the peripheral spikes can comprise alternate materials suitable for in vivo applications, such as titanium or other metals or polymers.

In embodiments where the baseplate comprises peripheral spikes, the glenoid cavity may require additional preparation to ensure proper affixation of the baseplate. For example, additional bone or tissue may be removed, or additional guide holes may be carved or drilled into the glenoid cavity. Additionally, the surgical plan may include more than one additional anti-rotation pin to secure and stabilize the baseplate as the peripheral spikes are inserted. Once the modified glenoid cavity is prepared and the anti-rotation pins have been inserted, the baseplate can be installed into the modified glenoid cavity by inserting, pressing, tapping, hammering, or otherwise affixing the spikes into the surgical site.

As will be understood from discussions herein, traditional materials such as titanium or metal alloys may be used for at least some of the components discussed herein. In some embodiments, polymeric materials that are suitable for long term in vivo use may also be utilized for some or all of the implant. In at least one embodiment, the pin guide and baseplate trial are constructed from a polymeric material and may be disposable (e.g., single use). Biocompatible or bioactive coatings may be applied to the surface of the chosen material for the baseplate, pin guide, baseplate trial, or other components to promote osseointegration and/or increase the biological response to the implantation. In various embodiments, a combination of the materials may be included in a single component (e.g., a pin guide with multiple materials, a baseplate with two or more different integrally formed 3D-printed materials, or two or more different materials not integrally formed).

In particular embodiments, the systems, devices, and instruments discussed herein may be utilized in a revision surgery, where a first implant is removed, and a second implant is installed. Such surgical plans may include removal and replace of a baseplate, a humeral stem, or both the baseplate and the humeral stem.

One skilled in the art will understand that processes discussed herein can include machine learning processes and other advanced artificial intelligence processes. For example, the system and processes of the present disclosure can perform diagnostics, image analysis, generate tasks or action items, provide customized recommendations according to user settings and preferences, generate 3D device models, generate surgical plans, generate computer-aided design (CAD) files, generate operating instructions for a surgical robot, generate personalized implant designs, generate notifications, and similar processes. Further, in at least one embodiment, the systems and processes discussed herein may provide an input to an additional process (e.g., surgery performed by a robot) or may be part of another process. In some embodiments, the system may use additional inputs and/or feedback loops to an iterative training process for a personalized implant generation process based on a plurality of parameters and adjustable metric values. Examples of such processes can be found in U.S. patent application Ser. No. 18/454,580, filed Aug. 23, 2023, and entitled "PATIENT-SPECIFIC MEDICAL DEVICES AND ADDITIVE MANUFACTURING PROCESSES FOR PRODUCING THE SAME", incorporated by reference herein in its entirety.

In some embodiments, the system can include a process for generating customized surgical plans that are populated for approval by a medical provider, surgeon, or similar healthcare professional. In various embodiments, the customized surgical plans can include one or more operating instructions to be transmitted to, installed on, or otherwise executed by a surgical robot or similar device. In some embodiments, the surgical robot can be autonomous or semi-autonomous.

As an example, implants, instruments, surgical plans, techniques, or information related to implants, instruments, surgical plans, or techniques, may be downloaded, saved, or otherwise captured within a file for use with a surgical robot, navigation system, or in another surgical setting. In at least one embodiment, the surgical plan may be transmitted to a surgical robot, navigation system, or other operating room system or device via a wireless transmission system (e.g., cellular, wifi, or other data transfer mechanism). Some non-limiting examples of file types that may be generated and/or transmitted include, but are not limited to: DICOM, STL, OBJ, TIFF, BMP, JPEG, AMF, 3MF, PLY, FBX, STEP/IGES, NIfTI, PDF, DOCX, CSV, .PRT, .ASM, .SLDPRT, .SLDASM, .PLAN, .NWD, .NWF, VRML, MIMICS, .DWG, etc.

In one non-limiting embodiment, the surgical robot can include a controller, a processor, a memory unit, a surgery module, a vision system (and/or other navigation systems), a sensor module, and a communication module. In various embodiments, the surgical robot may include a processor designed to execute patient-specific instructions to the surgery module to perform various actions associated with a surgical procedure. In some embodiments, the controller is designed to communicate with the processor and the memory unit to execute instructions to control one or more aspects of the surgery module. In some embodiments, the controller can be provided in the form of a virtual reality (VR) and/or augmented reality (AR) headset or similar controller. In some embodiments, the surgery module can include one or more articulating arms, one or more surgical devices (e.g., scalpel, retractor, drill, saw, suture instrument, suction, electrocautery, etc.), attachment(s) for accessories, or a combination thereof. In some embodiments, the surgical robot can also include a vision system used to track the movement of one or more aspects of the surgery module, a patient, a surgeon, the surgical environment, etc. As will be understood, the surgical robot may include or be in communication with other navigation systems, including, but not limited to, radar or sensor-based navigation (e.g., Bluetooth or BLE) and such instructions discussed herein may include instructions on navigation via one or more navigation systems. In various embodiments the surgical robot can utilize the sensor module to receive feedback signals related to the surgical operations or other actions performed by the surgical robot, patient, surgeon, or environment to compensate for changes during surgery or to otherwise facilitate execution of a surgical plan. In some embodiments, the sensor module is operatively coupled to the controller of the surgical robot. The communication module can be used to send instructions, feedback, signals, or other data between one or more aspects of the surgical robot, the surgeon, a computing system, or a combination thereof. In some embodiments, the communication module can be designed to generate notifications, transmit updated imaging, initiate safety alerts, send signals to particular surgical devices to indicate an implant is properly (or improperly) aligned, or similar data related to various actions or tasks being executed by the surgical robot, the surgeon, the medical team, or other aspects of the system or processes described herein.

In various embodiments, exemplary systems may receive information or feedback from a surgical robot or navigation system and update a machine learning process, one or more emphasis guidelines, weighting factors, or like processes or parameters to create a feedback loop to improve an existing surgical plan or a future surgical plan.

As will be understood from discussions herein, such a revision surgery may include removal of a first baseplate and/or humeral stem and related components. The revision surgery, in at least one embodiment, may proceed with modification of the glenoid cavity followed by the implant installation steps discussed herein.

CONCLUSION

While the particular embodiments described herein relate to shoulder replacement-based applications, it will be recognized and appreciated that the systems and processes described herein may be applicable to other joint implant-based applications. It will be appreciated by one skilled in the art that this embodiment is only a non-limiting example used to illustrate that the system and processes are designed to install a shoulder implant that has patient specific-geometry and a patient specific surgical plan.

Additional aspects, features, and processes of the claimed systems, devices, and processes will be readily discernible from the description herein, by those of ordinary skill in the art. Many embodiments and adaptations of the disclosure other than those herein described, as well as many variations, modifications, and equivalent arrangements and processes, will be apparent from or reasonably suggested by the disclosure and the description thereof, without departing from the substance or scope of the claims. Furthermore, any sequence(s) and/or temporal order of steps of various processes described and claimed herein are those considered to be the best mode contemplated for carrying out the claimed systems. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed systems. In addition, some steps may be carried out simultaneously, contemporaneously, or in synchronization with other steps.

Aspects, features, and benefits of the claimed devices and processes for using the same will become apparent from the information disclosed in the other applications as incorporated by reference. Variations and modifications to the disclosed systems and processes may be affected without departing from the spirit and scope of the novel concepts of the disclosure.

It will, nevertheless, be understood that no limitation of the scope of the disclosure is intended by the information disclosed in the applications incorporated by reference; any alterations and further modifications of the described or illustrated embodiments, and any further applications of the principles of the disclosure as illustrated therein are contemplated as would normally occur to one skilled in the art to which the disclosure relates. The description of the disclosed embodiments has been for illustration and description and is not intended to be exhaustive or to limit the devices and processes for using the same to the precise forms disclosed. Many modifications and variations are possible in light of the above teaching.

The embodiments were chosen and described to explain the principles of the devices and processes for using the same and their practical application to enable others skilled in the art to utilize the devices and processes for using the same and various embodiments and with various modifications as are suited to the particular use contemplated. Alternative embodiments will become apparent to those skilled in the art to which the present devices and processes for using the same pertain without departing from their spirit and scope. Accordingly, the scope of the present devices and processes for using the same is defined by the appended claims rather than the description and the embodiments described therein.

We claim:

1. A reverse shoulder arthroplasty implant system comprising:

a glenoid system for interfacing with anatomy of a patient, wherein the anatomy defines a Friedman's Line extending from a center of the patient's glenoid cavity to a medial end of the patient's scapula, the glenoid system comprising:

a baseplate comprising a baseplate body, the baseplate body comprising:

a patient-specific baseplate face comprising a periphery and positioned opposite a second baseplate face, the patient-specific baseplate face arranged and shaped to conformally engage with a bony surface of the anatomy at a baseplate face angle, wherein a baseplate plane bisects the baseplate body at two representative points of the periphery, and the baseplate angle is between about 25° to 88° with respect to the baseplate plane and the Friedman's Line;

a central post extending from the patient-specific baseplate face at a post angle and a post position, the post angle between about 2° to 80° with respect to the Friedman's Line;

a taper extending from the second baseplate face at a taper angle and a taper position, the taper angle between about 2° to 80° with respect to the Friedman's Line; and one or more patient-specific regions comprising a textured surface; and a guide instrument comprising:

a guide body comprising:

a patient-specific guide face arranged and shaped to conformally engage with the bony surface at a guide face angle; and a guide opening positioned on the patient-specific guide face at a guide opening position and a guide opening angle; and a handle connected to the guide face by a shaft, wherein a guide element is inserted through the handle to the guide opening; and a trial instrument comprising:

a trial body comprising a patient-specific trial face and a second trial face positioned opposite the patient-specific trial face, the patient-specific trial face arranged and shaped to conformally engage with the bony surface at a trial face angle; and a trial opening extending between the patient-specific trial face and the second trial face, the trial opening oriented at a trial opening position and a trial opening angle, wherein:

the baseplate face angle, the guide face angle, and the trial face angle are substantially similar angles with respect to the Friedman's Line;

the post angle, the guide opening angle, and the trial opening angle are substantially similar and are each measured with respect to the Friedman's Line;

the post position, the guide opening position, and the trial opening position are substantially similar in relation to the bony surface;

the post angle and the taper angle are different with respect to the Friedman's Line; and the post position and the taper position are offset by at least 1 mm.

2. The reverse shoulder arthroplasty implant system of claim 1, wherein:

the Friedman's Line represents an x-axis;

a y-axis extends 90° from the Friedman's Line in a vertical direction; and a z-axis extends 90° degrees from the Friedman's Line in a horizontal direction.

3. The reverse shoulder arthroplasty implant system of claim 2, wherein the two representative points comprise a first point on the periphery furthest from a center of the patient-specific baseplate face and a second point on the periphery closest to the center of the patient-specific baseplate face.

4. The reverse shoulder arthroplasty implant system of claim 3, wherein the baseplate face angle is not parallel to the x-axis.

5. The reverse shoulder arthroplasty implant system of claim 4, wherein the baseplate face angle is not perpendicular to the x-axis.

6. The reverse shoulder arthroplasty implant system of claim 3, wherein the baseplate face angle is between about 30° and 80°.

7. The reverse shoulder arthroplasty implant system of claim 6, wherein the post angle is not parallel and not perpendicular to the x-axis.

8. The reverse shoulder arthroplasty implant system of claim 6, wherein the post angle is between about 10° and 45°.

9. The reverse shoulder arthroplasty implant system of claim 8, wherein the taper angle is not parallel and not perpendicular to the x-axis.

10. The reverse shoulder arthroplasty implant system of claim 8, wherein the taper angle is between about 10° and 45°.

11. The reverse shoulder arthroplasty implant system of claim 1, wherein the baseplate body comprises a patient-specific thickness that varies between 3-100 mm.

12. The reverse shoulder arthroplasty implant system of claim 1, wherein at least one peripheral through-hole extends between the patient-specific baseplate face and the second baseplate face.

13. The reverse shoulder arthroplasty implant system of claim 12, wherein the at least one peripheral through-hole is designed to receive a peripheral fixation element.

14. A reverse shoulder arthroplasty implant system comprising:
a glenoid system for interfacing with anatomy of a patient, wherein the anatomy defines a Friedman's Line extending from a center of the patient's glenoid cavity to a medial end of the patient's scapula, the glenoid system comprising:
a baseplate comprising a baseplate body, the baseplate body comprising:
a patient-specific baseplate face comprising a periphery and positioned opposite a second baseplate face, the patient-specific baseplate face arranged and shaped to conformally engage with a bony surface of the anatomy;
a patient-specific thickness that varies between 3-100 mm;
a central post extending from the patient-specific baseplate face at a post angle and a post position, the post angle between about 2° to 80° with respect to the Friedman's Line;
a taper extending from the second baseplate face at a taper angle and a taper position, the taper angle between about 2° to 80° with respect to the Friedman's Line; and
one or more patient-specific regions comprising a textured surface; and a guide instrument comprising:
a guide body comprising:
a patient-specific guide face arranged and shaped to conformally engage with the bony surface; and
a guide opening positioned on the patient-specific guide face at a guide opening position and a guide opening angle; and
a handle connected to the guide face by a shaft, wherein a guide element is inserted through the handle to the guide opening; and
a trial instrument comprising:
a trial body comprising a patient-specific trial face and a second trial face positioned opposite the patient-specific trial face, the patient-specific trial face arranged and shaped to conformally engage with the bony surface; and
a trial opening extending between the patient-specific trial face and the second trial face, the trial opening oriented at a trial opening position and a trial opening angle, wherein:
the post angle, the guide opening angle, and the trial opening angle are substantially similar and are each measured with respect to the Friedman's Line;
the post position, the guide opening position, and the trial opening position are substantially similar in relation to the bony surface;
the post angle and the taper angle are different with respect to the Friedman's Line; and
the post position and the taper position are offset by at least 1 mm.

15. The reverse shoulder arthroplasty implant system of claim 14, wherein:
the Friedman's Line represents an x-axis;
a y-axis extends 90° from the Friedman's Line in a vertical direction; and
a z-axis extends 90° degrees from the Friedman's Line in a horizontal direction.

16. The reverse shoulder arthroplasty implant system of claim 15, wherein the post angle is not parallel and not perpendicular to the x-axis.

17. The reverse shoulder arthroplasty implant system of claim 15, wherein the post angle is between about 10° and 45°.

18. The reverse shoulder arthroplasty implant system of claim 17, wherein the taper angle is not parallel and not perpendicular to the x-axis.

19. The reverse shoulder arthroplasty implant system of claim 17, wherein the taper angle is between about 10° and 45°.

20. A reverse shoulder arthroplasty implant system comprising:
a glenoid system for interfacing with anatomy of a patient, wherein the anatomy defines a Friedman's Line extending from a center of the patient's glenoid cavity to a medial end of the patient's scapula, the glenoid system comprising:
a baseplate comprising a baseplate body, the baseplate body comprising:
a patient-specific baseplate face comprising a periphery and positioned opposite a second baseplate face, the patient-specific baseplate face arranged and shaped to conformally engage with a bony surface of the anatomy;
a central post extending from the patient-specific baseplate face at a post angle and a post position, the post angle between about 2° to 80° with respect to the Friedman's Line;

a taper extending from the second baseplate face at a taper angle and a taper position, the taper angle between about 2° to 80° with respect to the Friedman's Line; and one or more patient-specific regions comprising a textured surface; and a guide instrument comprising:

a guide body comprising:

a patient-specific guide face arranged and shaped to conformally engage with the bony surface; and a guide opening positioned on the patient-specific guide face at a guide opening position and a guide opening angle; and a handle connected to the guide face by a shaft, wherein a guide element is inserted through the handle to the guide opening; and a trial instrument comprising:

a trial body comprising a patient-specific trial face and a second trial face positioned opposite the patient-specific trial face, the patient-specific trial face arranged and shaped to conformally engage with the bony surface; and a trial opening extending between the patient-specific trial face and the second trial face, the trial opening oriented at a trial opening position and a trial opening angle, wherein:

the post angle, the guide opening angle, and the trial opening angle are substantially similar and are each measured with respect to the Friedman's Line;

the post position, the guide opening position, and the trial opening position are substantially similar in relation to the bony surface;

the post angle and the taper angle are different with respect to the Friedman's Line; and the post position and the taper position are offset by at least 1 mm.

* * * * *